United States Patent
Wagner

[11] Patent Number: 6,035,246
[45] Date of Patent: Mar. 7, 2000

[54] METHOD FOR IDENTIFYING KNOWN MATERIALS WITHIN A MIXTURE OF UNKNOWNS

[75] Inventor: John S. Wagner, Albuquerque, N.Mex.

[73] Assignee: Sandia Corporation, Albuquerque, N.Mex.

[21] Appl. No.: 08/773,748

[22] Filed: May 15, 1997

Related U.S. Application Data

[63] Continuation of application No. 08/334,505, Nov. 4, 1994, abandoned.

[51] Int. Cl.[7] ............................................... G06F 19/00
[52] U.S. Cl. ............... 700/266; 250/339.05; 250/339.11; 250/339.12; 356/320; 422/82.05
[58] Field of Search .................... 250/339.05, 339.11, 250/339.12, 373; 356/317, 318, 320; 364/497, 498; 395/13, 20, 21, 23; 422/82.05; 436/171; 700/266; 706/15, 45

[56] References Cited

U.S. PATENT DOCUMENTS

| | | | |
|---|---|---|---|
| 4,994,671 | 2/1991 | Safinya et al. | 250/339.05 X |
| 5,070,245 | 12/1991 | Rantala et al. | 250/343 |
| 5,272,345 | 12/1993 | Durham et al. | 250/373 |
| 5,369,578 | 11/1994 | Roscoe et al. | 364/422 |
| 5,435,309 | 7/1995 | Thomas et al. | 128/633 |
| 5,508,203 | 4/1996 | Fuller et al. | 436/149 |
| 5,512,490 | 4/1996 | Walt et al. | 436/171 |

*Primary Examiner*—Edward R. Cosimano
*Attorney, Agent, or Firm*—Gregory A. Cone

[57] ABSTRACT

One or both of two methods and systems are used to determine concentration of a known material in an unknown mixture on the basis of the measured interaction of electromagnetic waves upon the mixture. One technique is to utilize a multivariate analysis patch technique to develop a library of optimized patches of spectral signatures of known materials containing only those pixels most descriptive of the known materials by an evolutionary algorithm. Identity and concentration of the known materials within the unknown mixture is then determined by minimizing the residuals between the measurements from the library of optimized patches and the measurements from the same pixels from the unknown mixture. Another technique is to train a neural network by the genetic algorithm to determine the identity and concentration of known materials in the unknown mixture. The two techniques may be combined into an expert system providing cross checks for accuracy.

68 Claims, 26 Drawing Sheets

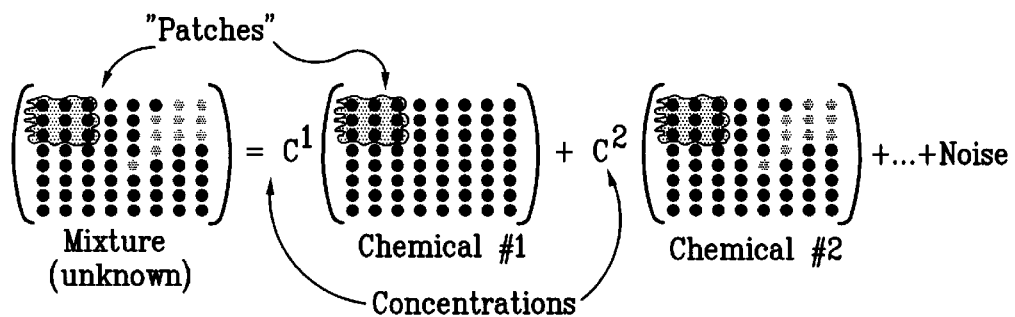
FIG. 3
$$\sigma^2(C) = \overset{100}{\overbrace{\delta m_i^2 \left(\frac{\partial C}{\partial m_i}\right)^2}} + \overset{120}{\overbrace{\delta m_i \delta s_i \frac{\partial C}{\partial m_i} \frac{\partial C}{\partial s_i}}} + \overset{130}{\overbrace{\delta s_i^2 \left(\frac{\partial C}{\partial s_i}\right)^2}}$$
FIG. 4
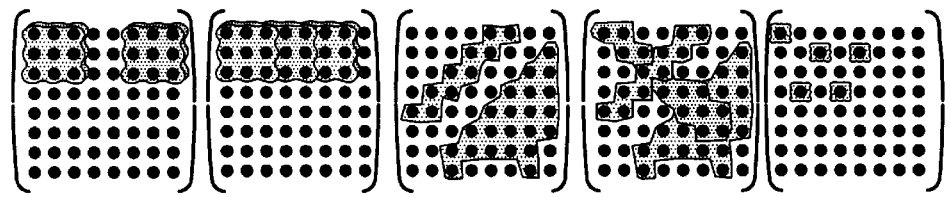
FIG. 5

Brainscan Level 2

Brainscan Level 3

METHOD FOR IDENTIFYING KNOWN MATERIALS WITHIN A MIXTURE OF UNKNOWNS

This is a continuation of U.S. Ser. No. 08/334,505 filed Nov. 4, 1994, now abandoned.

This invention was made with Government support under Contract DE-AC04-94AL85000 awarded by the U.S. Department of Energy. The Government has certain rights in this invention.

BACKGROUND OF THE INVENTION

This invention relates to methods and systems for identifying known materials or artifacts from within an unknown mixture. More particularly it can relate to system, and methods for identifying chemicals or biological constituents within a mixture of known and unknown substances; it can also relate to systems and methods for identifying shapes or patterns from a noise filled background. Still more particularly, it relates to an expert system which analyses the interaction of a first set of wavelengths of electromagnetic radiation on an unknown mixture in relation to a database of responses to that radiation of known constituents to provide concentrations of the known constituents in the mixture. Still more particularly, the expert system has two components to analyse the information received from the mixture describing the interaction of the radiation, a first subsystem utilizing a multivariate multidimensional patch algorithm trained by an evolutionary algorithm to provide the concentrations and a second subsystem utilizing a neural network also trained by an evolutionary algorithm to provide the concentration information.

Searching for the presence or absence of a known material within an unknown mixture is a classic problem with a variety of methods of solution. Most college students who took physical chemistry classes will remember the linear process-of-elimination techniques used in the laboratory to determine the unknown chemical from the sample presented to them for analysis. With the advent of the availability of increasingly powerful and inexpensive computing power, certain computer implemented processes for analyzing the problem have been brought to bear. These include various numerical analysis techniques (i.e. multivariate analysis, monte carlo techniques, etc.), genetic algorithms, and neural networks. Unfortunately, the nature of the problem presented herein is so computationally intense that solutions using these computer implemented processes are still beyond of the capability of readily available computers. What is needed is a new approach based upon but significantly more powerful than the presently known computer-implemented techniques to provide a fast and accurate solution to the problem.

SUMMARY OF THE INVENTION

This invention is an expert system which employs either or both of two computer-implemented processes to analyze data taken which describes the responses of an unknown mixture to multiple wavelengths of electromagnetic radiation to determine the amount of a particular known constituent in the unknown mixture. Both processes employ a new type of genetic algorithm, hereinafter called an evolutionary algorithm, to train and optimize either a numerical analysis process or a neural network to identify the known constituent.

The evolutionary algorithm is more powerful and flexible than its antecedents. It reworks the standard mating and mutation techniques to achieve, very efficiently and rapidly, an optimized solution set (genetic sequence). For the numerical analysis, a new multidimensional multivariate analysis method has been created which, when combined with the evolutionary algorithm, can achieve heretofore unattainable solutions to complex identification problems. For the neural network, the flexibility the network has been increased in order that it can be efficiently optimized by the evolutionary algorithm.

In the numerical analysis techniques the evolutionary algorithm trains and optimizes the technique using a first set of wavelengths of electromagnetic radiation to interact with a known sample. The responses of the known sample are recorded at a second set of wavelengths. An optimized solution set is then created for each known constituent for which a search is desired. The unknown mixture is then irradiated with the same first set of wavelengths and data are recorded at the second set of wavelengths. The optimized solution sets for the various known constituents are then run on the data from the unknown mixture to determine the amount, if any, of each of the knowns.

In the neural network analysis, the neural network is trained for a given set of one or more known constituents where the concentrations of the members of the set change from generation to generation, but the members of the set remain the same. After some number of generations, the now-trained neural net has had its neurons and interconnection weights reconfigured by the evolutionary algorithm to provide a very fast and efficient measure of the concentrations of any of the members of the training set that are present in the unknown.

The expert system combines these two subsystems to provide two different pathways to the desired concentration information from the unknown mixture with very useful cross checking information as to the accuracy of the information.

BRIEF DESCRIPTION OF THE DRAWINGS

FIG. 3 is a diagram showing how the summation of a number of fluorescence return patches for known chemicals multiplied by their concentrations plus noise add up to the fluorescence return from the unknown mixture.

FIG. 4 is a diagram showing the various constituents of the uncertainty of a concentration estimate.

FIG. 5 is a diagram showing several different patch strategies with a variety of allowed pixel groupings.

FIG. 6A is group of three arbitrary chemicals whose gaussian-shaped spectral signatures are placed on a diagonal without noise.

FIG. 6B adds a contaminant whose concentration is 100 times higher to the graph of FIG. 6A.

FIG. 6C shows the results of running a one-dimensional multivariate analysis of the data from FIG. 6B at varying degrees of noise.

FIG. 6D shows the results of running a two-dimensional multivariate analysis for three patches of the data from FIG. 6C at varying degrees of noise.

FIG. 6E is a pixel plot of the three patches used in the analysis for FIG. 6D.

FIG. 10A shows fitness level as a function of the generation for the average (darker shaded) and best (lighter shaded) sequences in each generation.

FIG. 10B shows the average patch size history over 500 generations.

FIG. 10C shows the patch locations on the pixel array for the average genetic sequence.

FIG. 10D shows the patch locations on the pixel array for a "best fitness" genetic sequence after 500 generations.

FIG. 10E is a plot of the training set with the magnitude returns associated with the pixels being represented by the shading.

FIG. 10F is a plot of the fitnesses of all 100 genetic sequences in the 500th generation with the raw fitness appearing as dots at the top edge of the plot and the weighted fitnesses appearing as asterisks.

FIG. 12A is a plot of the training set used for this generation.

FIG. 12B is a plot of the average and best fitness scores for the genetic sequences in each of the 50 generations.

FIG. 12C is a plot of the raw and weighted fitnesses of the 100 genetic sequences at the 50th generation.

FIG. 12D is a plot of the weights associated with the pixel inputs in the top layer of the net at generation 50.

FIG. 12E is a plot of the weights associated with each of the inputs to each of the neurons in the second layer of the net.

FIG. 12F is a plot of the weights associated with each of the inputs to each of the neurons in the bottom layer of the net.

DETAILED DESCRIPTION OF THE INVENTION

This detailed description of the invention will begin with a discussion of one preferred embodiment involving recognition of chemicals within a distant plume on the basis of UV fluorescence when irradiated with a multispectral uv laser pulse. This was the first application developed for this invention. Following this will be a discussion of other uses of the invention and a concluding section with a detailed discussion of the mathematics involved in this invention.

First Preferred Embodiment

One purpose of this invention is to estimate the individual chemical concentrations in a multicomponent mixture using a premeasured chemical catalog of calibrated spectral signatures. It should be able to reject noise and optical contaminants such as scattered light, and be able to reject unknown or uninteresting chemicals.

Figure 1A:
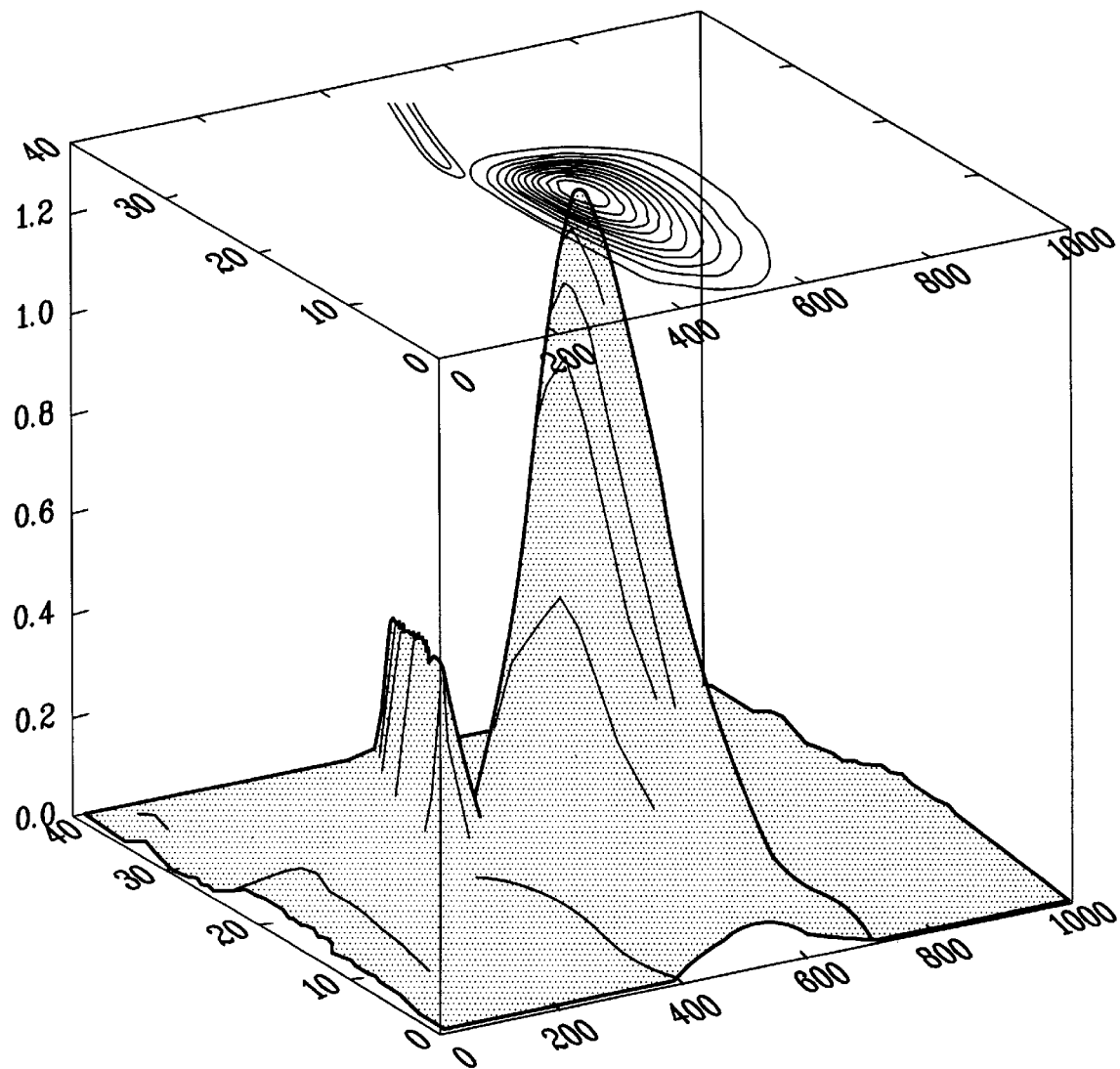
FIGS. 1A and 1B are three dimensional graphs of the uv fluorescence spectra of acetone and benzene respectively with horizontal scales of 41 excitation wavelengths and 1024 fluorescence (return) wavelengths and a vertical scale for magnitude of the returns.
Figure 1B:
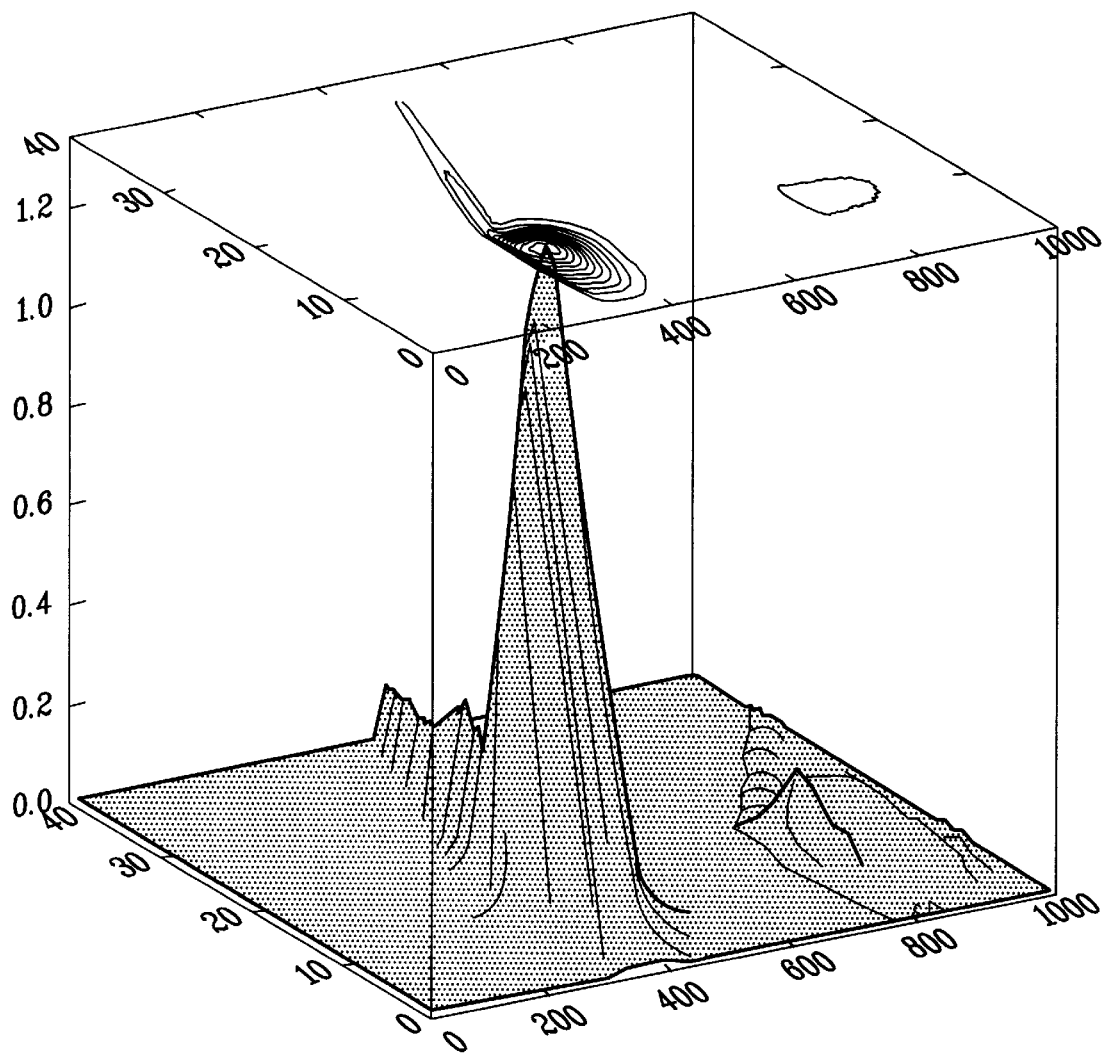

A multispectral laser remote sensing system generates a range-resolved 2-D spectral signature of a remote object or plume. The 2-D spectra can be visualized as a surface: the surface height representing return signal intensity, with the excitation wavelength from the laser source along one axis and emission (or fluorescence) wavelength from the interrogated object along the other axis. Two typical uv spectra taken by a uv fluorometer are shown in FIGS. 1A and 1B, for acetone and benzene respectively. Note that, at least in the ultraviolet, spectral features can be broad and featureless: this is not necessarily so in the visible and infrared. The system of this invention can use both broad and featureless as well as sharply defined spectra.

When the object or plume is made up of many components, the returning 2-D mixture signal is assumed to be a linear superposition of the contributions from each component. The signal contribution from each component depends on its unique spectral shape amplified by its relative concentration.

Historically, algorithms designed to estimate concentrations of components in mixtures used a chemometric approach involving 1-D least-square minimizations (see "Numerical Recipes: The Art of Scientific Computing", W. H. Press et al., Cambridge University Press, 1986, p. 509)

and in some cases normal-component analysis (see "Factor Analysis in Chemistry", E. R. Malinowsky and D. G. Howery, Krieger Publishing Co., 1989, p. 141). These techniques do tend to work well for many applications. Nonetheless these conventional methods do not utilize all the available information in spectra, such as the correlation of one pixel's intensity with another. A pixel here is defined as a unique point representing the intersection one of the wavelength bands from the first set of wavelengths from the laser source and one of the wavelength bands in the second set of wavelengths for the returns from the irradiated mixture. As an aside, it should be noted that while for this preferred embodiment the first wavelengths will differ from the second wavelengths, for measurements involving elastic backscattering effects this may not necessarily be the case.

Figure 2:
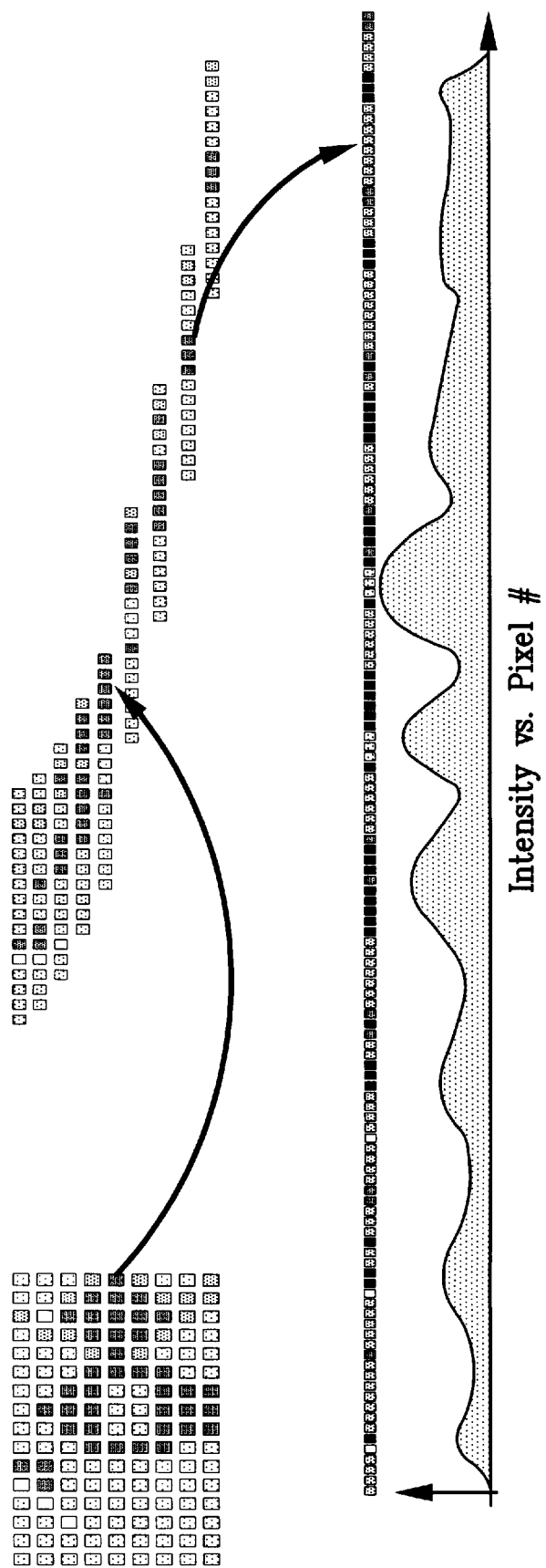
FIG. 2 is a chart showing the decomposition of a two dimensional patch into a one dimensional string, with the attendant loss of important information associated with the grouping with neighboring pixels.
Figure 6A:
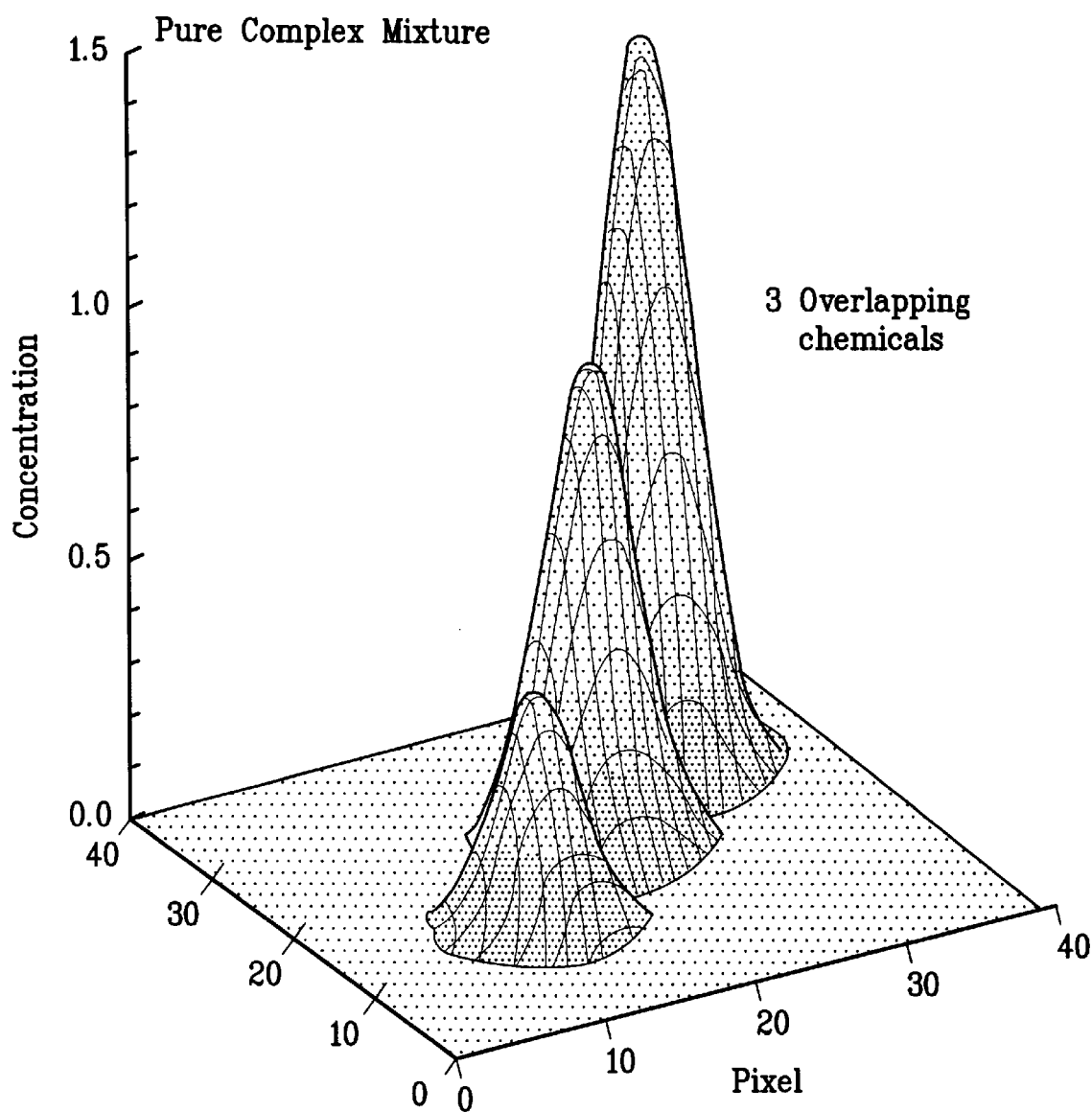
FIGS. 6A–6E are a series of graphs comparing the use of one dimensional and two dimensional multivariate algorithms.
Figure 6B:
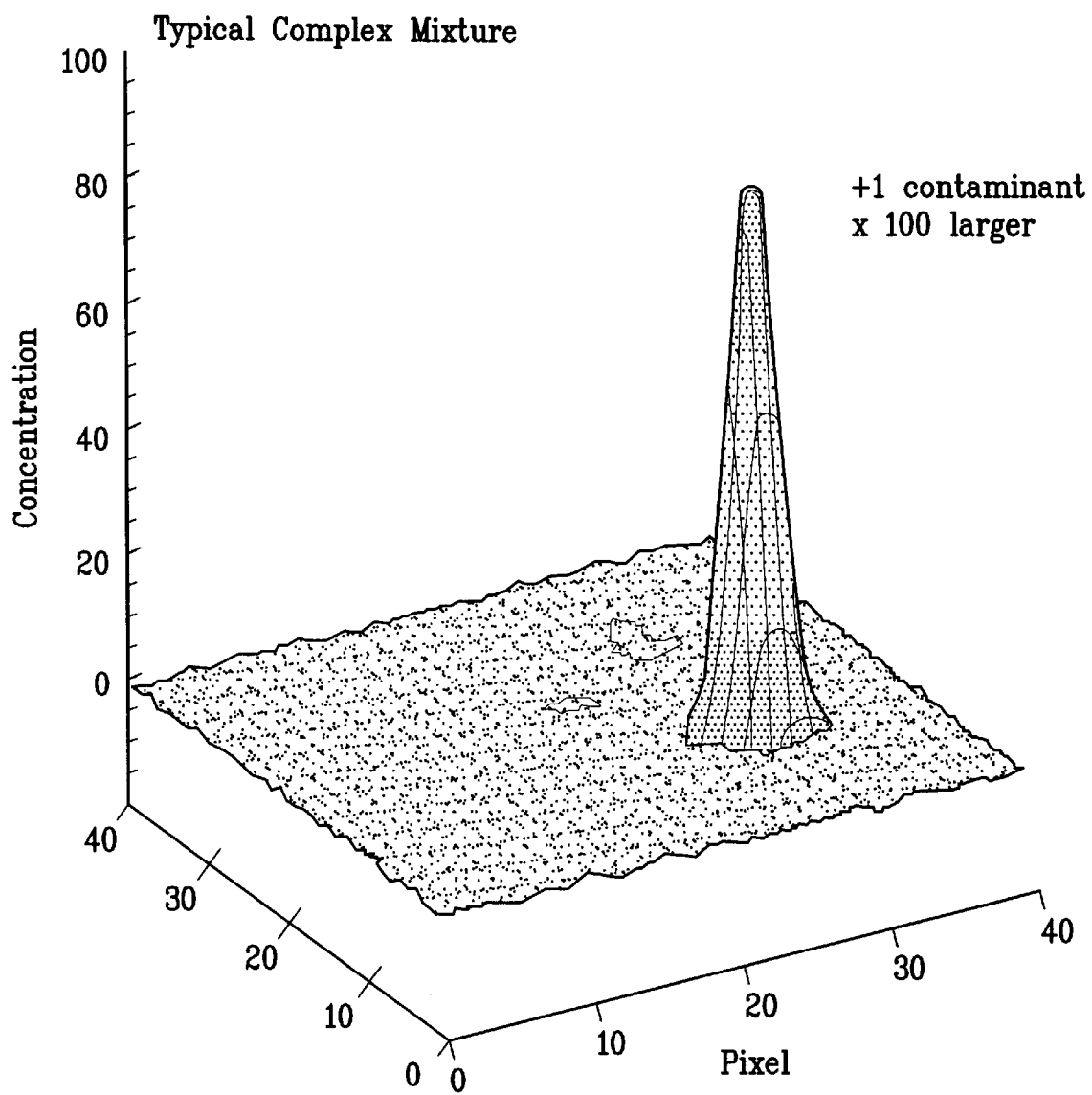
Figure 6C:
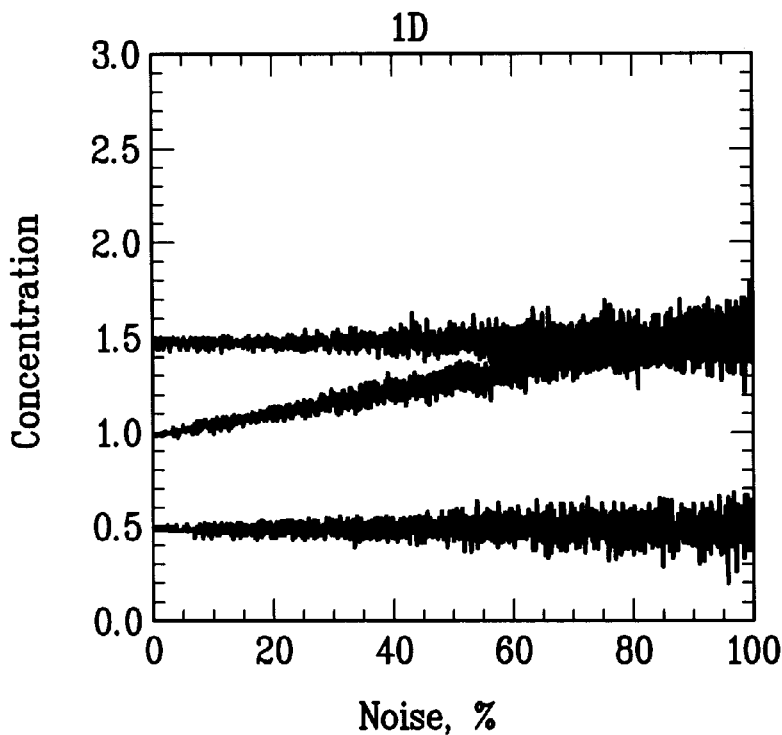
Figure 6D:
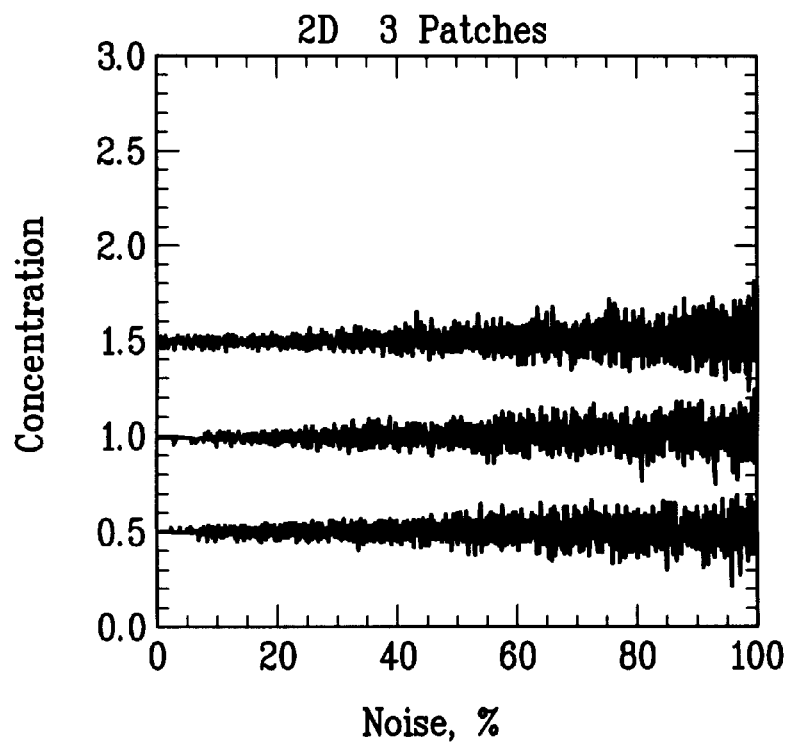
Figure 6E:
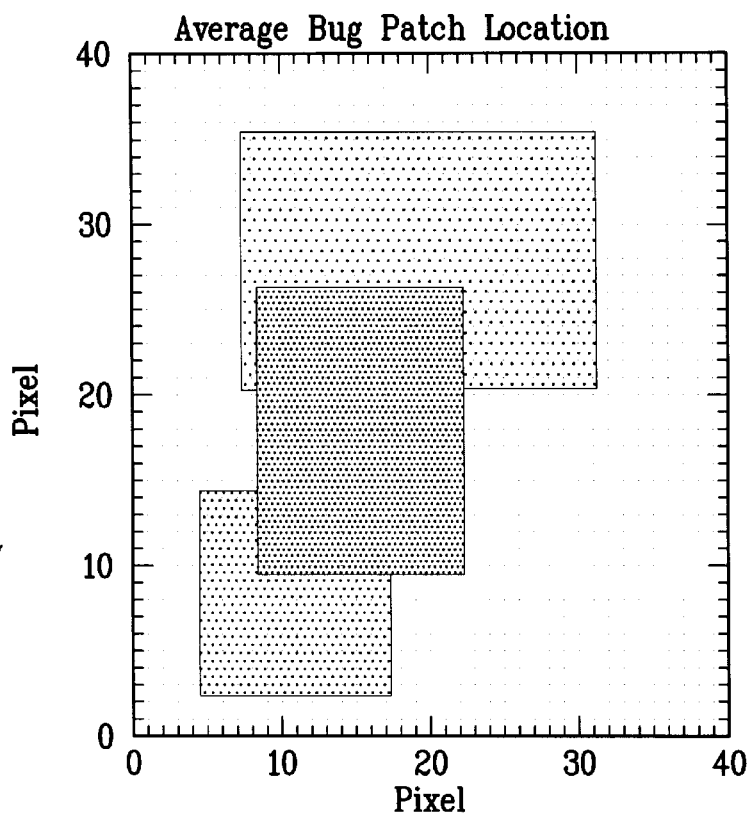

For example when using a conventional 1-D method, the pixels of the mixture can be arbitrarily scrambled without changing the resulting concentration estimates, as long as the identical pixels in the database catalog are scrambled in the same way. In 2-D (and in higher dimensions) the spectra can be converted into a 1-D problem by stringing the pixels out, as shown in FIG. 2. In higher dimensions, such as in 2-D, the pixel-to-pixel correlations are even more structured to the human eye, and more complex in the sense that pixels along diagonals, and well-separated pixels can be correlated with each other.

In order to take advantage of the additional information available in spectral signatures I have developed new techniques of analyzing spectral signatures, including new ways of adaptively extracting minute chemical concentrations in complex multicomponent mixtures. The chemical recognition and analysis research has concentrated on multivariate methods, neural nets and genetic optimization. Other techniques can be productive as well, for example massively parallel implementations, accurate uncertainty estimates on concentrations, and intelligent techniques to search for chemicals when the database catalog becomes very large (-hundreds). These techniques have important uses that go well beyond laser remote sensing that will be discussed further below.

The Multivariate Approach

A core algorithm in the chemical recognition method and system is the multivariate 'patch' algorithm. This algorithm computes the chemical concentrations and estimates the uncertainty of those concentrations. Conceptually the multivariate method is like a least squares fit, where the fitted parameters (the concentrations) are chosen to minimize the residuals between the measured unknown mixture and the fitted solution. The 'patch' algorithm extends this approach in the sense that it minimizes the residuals on pixel sets which collectively contain the most important features in a particular chemical spectrum. Since neighboring pixels often contain valuable correlated information, this approach enables better concentration estimation and better noise rejection. The algorithm incorporates conventional 1-D chemometrics as a limiting case. Visually these correlated sets of pixels appear as patches when overlaid onto a 2-D spectrum, hence the name. This is illustrated in FIG. 3, where the mixture is on the left, and is equal to a sum of chemical samples multiplied by their respective concentrations, and may be contaminated with noise. One patch occupies the same pixels in the mixture and in the chemical components.

Mathematically, the 'patch' algorithm computes the residuals between the mixture and a hypothetical solution, for all pixels in each patch, then minimizes this residual, or a function of this residual, for every patch independently. The user can chose to minimize the squared sum, the sum of the squared (as in least squares), or the summed absolute value (as in robust estimation) of the residuals in every patch. There are trade-offs associated with these choices. The system of equations is inverted by computing the pseudo-inverse of the patch-sum matrix using singular value decomposition. The concentrations are then computed when the pseudo inverse is multiplied by the mixture and component-sum matrix. The mathematical details are discussed in greater detail below.

After the concentrations are estimated, the algorithm then computes an uncertainty estimate. This uncertainty estimate is derived from the first three terms of the Taylor series expansion of the rate of change of concentration from both mixture 100, chemical database 130 and mixture-chemical (cross product) uncertainty 120. This is shown in FIG. 4. Conventional algorithms usually assume only the mixture has measurement uncertainty (term 100 in the figure), with the curious result that the uncertainty in the concentrations is computed from a covariance matrix that is independent of the mixture itself. In other words all mixtures would have the same uncertainty in the concentrations. The covariance matrix is the first term in the Taylor expansion, with the other new terms exhibiting the expected loss of confidence as the concentrations become relatively small or when there is a chemical missing from the database. I have also implemented a Monte Carlo uncertainty estimate, so that, if the mixture measurements do not obey a normal statistical distribution, I can still estimate concentration errors with a real system response.

Patches are lists of correlated pixels, but how are these lists chosen? This question of patching strategy is a complicated one. Patches can overlap, be sparse, or widely separated. In fact a patch does not have to made of contiguous pixels at all. Pixels outside of a patch are ignored. Although any reasonable patching strategy will yield very good results, for many problems the optimization of the patch algorithm is too labor intensive and too subjective. Some of the possibilities are shown in FIG. 5. The optimization of the patches will be discussed in the next section on genetic optimizations by the evolutionary algorithm of this invention.

As an example of the benefits of the flexibility of the patch algorithm, consider the following problem. A set of three gaussian-shaped 'computer synthesized' chemicals are created with their peaks on a diagonal, and the spectra of these three chemicals are stored in the multivariate algorithm's chemical database. The image is made up of 40x40 pixels. Mixtures are computer created by combining these three chemicals with concentrations 0.5, 1.0, and 1.5 respectively. Then a fourth chemical is added to the mixtures, off diagonal, with a very large concentration of 100.0. Both the conventional 1-D algorithm and the 'patch' algorithm are given this problem, with increasing (0% to 100%) random noise added. The results are shown in FIGS. 6A–6E. The 1-D algorithm is unable to reject the contaminate as noise is increased.

Figure 7A:
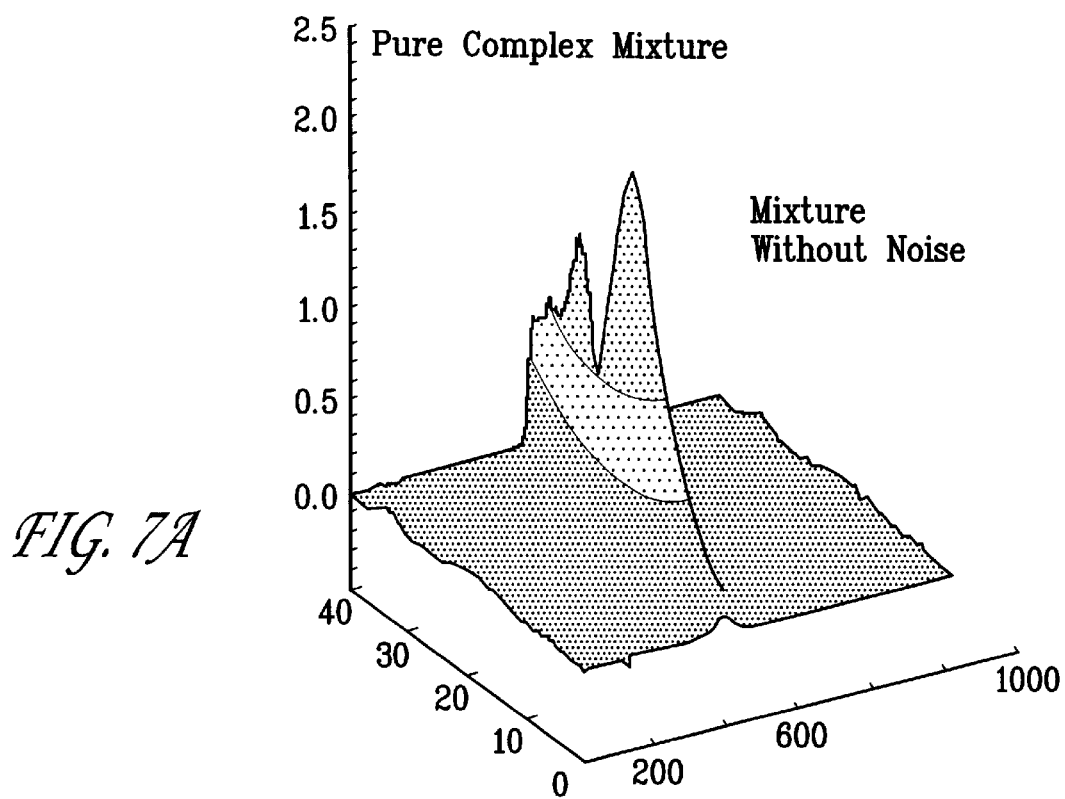
FIG. 7A is a graph showing the spectral response of a mixture of methanol, xylene and toluene without noise.
Figure 7B:
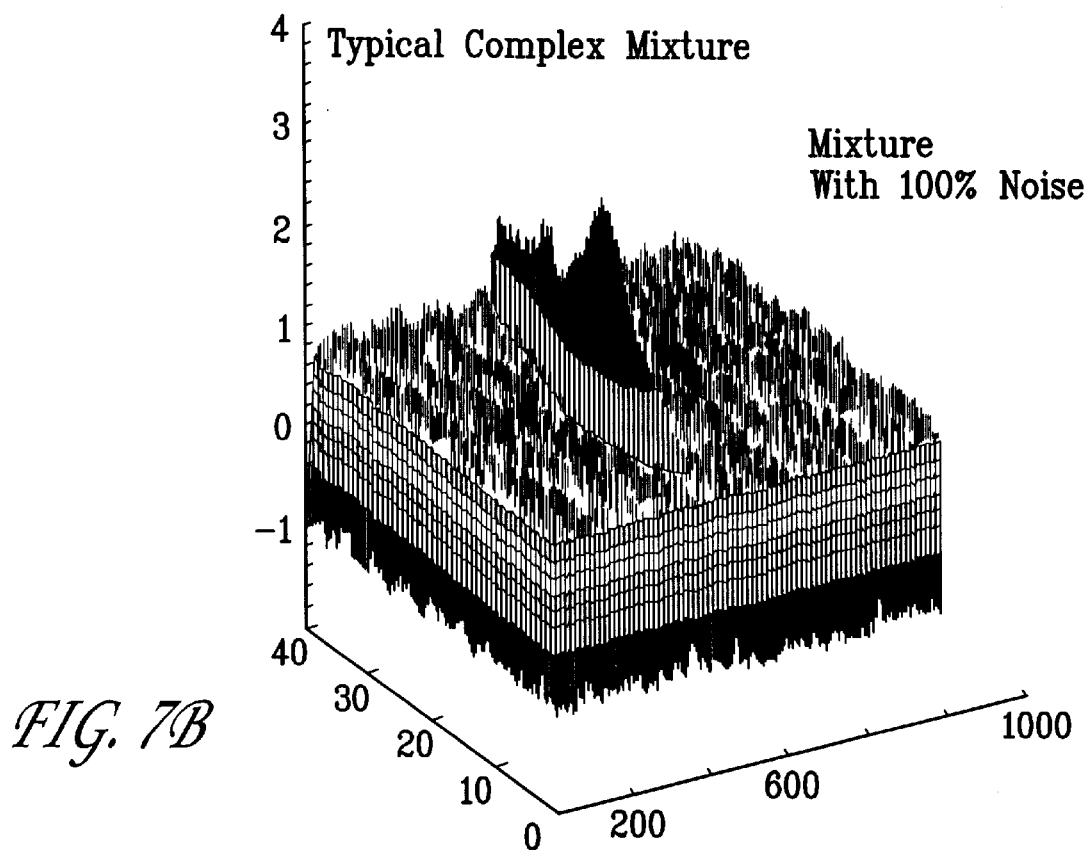
FIG. 7B is a graph which takes the information from FIG. 7A and adds up to 100% noise.
Figure 7C:
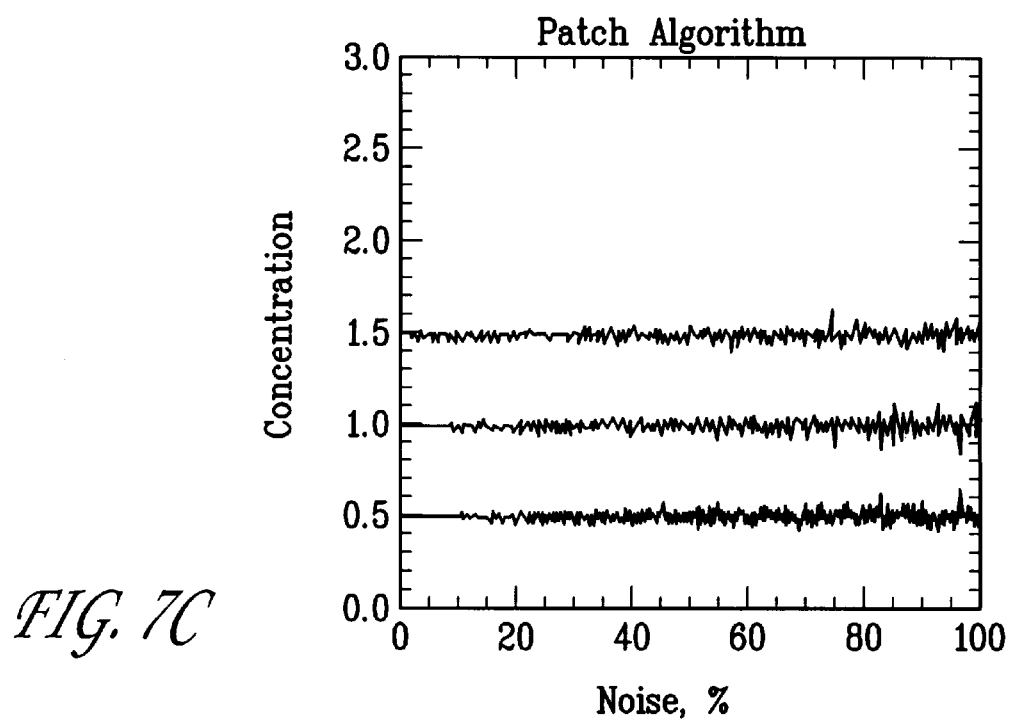
FIG. 7C is a plot of the output of the patch multivariate algorithm showing the successful identification of the three known constituents through the entire noise range.

To demonstrate the algorithm on 'real' data, FIGS. 7A, 7B, and 7C show the results of the 'patch' algorithm identifying methanol, xylene, and toluene with relative concentrations of 0.5, 1.0, and 1.5 respectively, as up to 100% noise is added. The spectrum for each chemical was taken with a uv fluorometer, and the mixtures were generated by the computer by adding the spectra according to the concentrations, and then adding additional random noise. The random noise was uniformly distributed from −1.0 to 1.0 multiplied by the percentage. The size of the images was 41×1024 pixels. No attempt was made to remove the scattered light from the raw data. The code achieves good concentration estimates (accurate to a few percent) even at 100% noise.

Genetic Optimization of the Patch Algorithm

Figure 8:
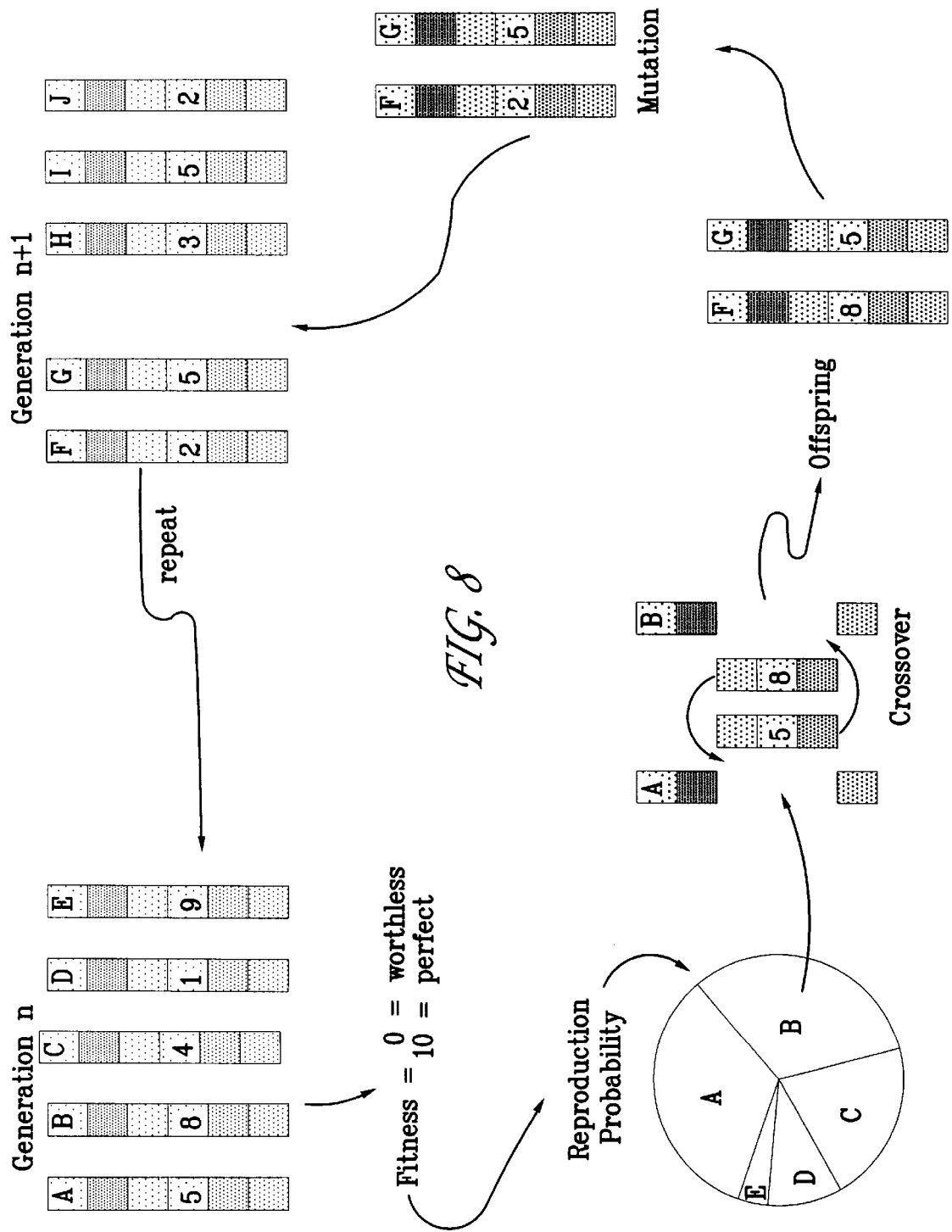
FIG. 8 is a diagram of the steps of the evolutionary algorithm as applied to the multivariate patch technique with the upper left corner showing a genetic sequence containing at least information regarding pixels within a patch, the next step showing reproduction (mating) probability as a function of the fitness of a genetic sequence(determined by its success in identifying a chemical), the next step showing segments of the sequences being exchanged between mating sequences with offspring with altered sequences appearing in the next generation, in the next step some of the offspring also receive mutations to random genes within the sequence with the new generation repeating the process.

To overcome the need for trial and error optimization of the 'patch' algorithm I have developed a novel Genetic Algorithm (GA) to optimize the lists of correlated pixels for any set of candidate chemicals. In a genetic algorithm a set of genetic-like sequences is created in which each sequence can completely describe a possible solution to a problem. Every genetic sequence, or 'bug', must compete with its peers on the problem, and the most fit are allowed to generate offspring for the next generation, with occasional mutation to introduce new genetic material into the population. Generation after generation the population relentlessly improves its fitness. Genetic algorithms are exceptionally good at search and optimization when applied to problems with very large multidimensional solution spaces. GA's, used carefully, are not easily trapped in local minima or maxima, a problem that can plague hill climbing methods or variations on Newton's method. A schematic diagram of a genetic algorithm is shown in FIG. 8. A good background article on genetic algorithms can be found in the July 1992 issue of Scientific American entitled "Genetic Algorithms" by John H. Holland, pp. 66–72.

Figure 9:
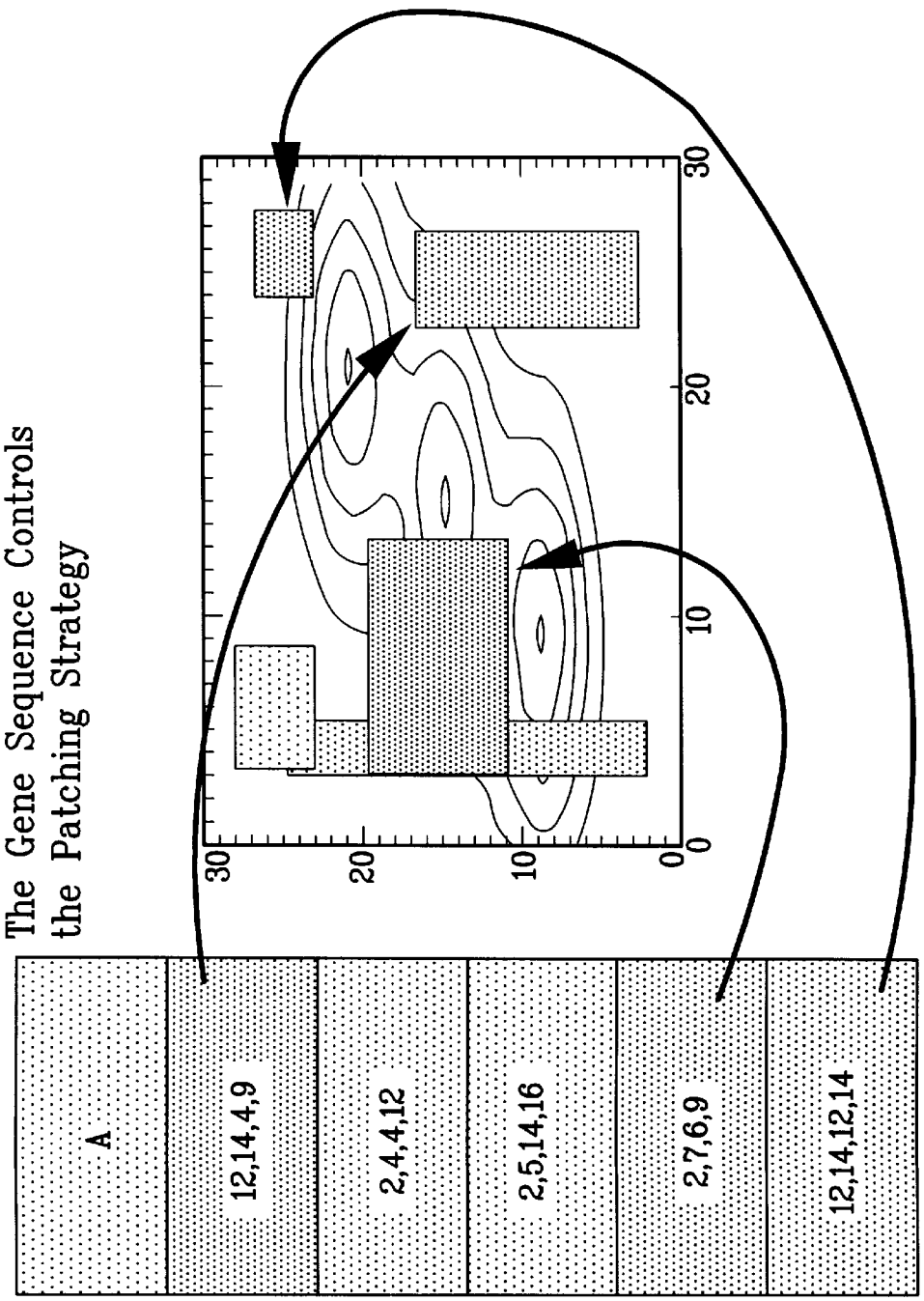
FIG. 9 is a diagram showing that portion of a gene sequence which controls the patching strategy by describing the patch boundaries.

Applied to the patch algorithm problem, the GA's genetic sequences are the patch-lists, which describe which pixels are in a given patch. The GA ferrets out which pixels contribute to the solution and organizes them optimally. FIG. 9 shows a GA controlling rectangular patches. I have also written GA's not restricted to rectangular patches, and are currently evaluating the trade-offs.

In the training sessions we have conducted so far, the genetically optimized code can frequently achieve an order of magnitude improvement in speed and accuracy, and frequently comes up with novel and better solutions to complex problems than those anticipated by the inventor. The speed increase comes from the fact that the genetically optimized 'patch' algorithm typically uses only a small fraction of the total pixels in the solution, greatly reducing the number of operations required.

Figure 10A:
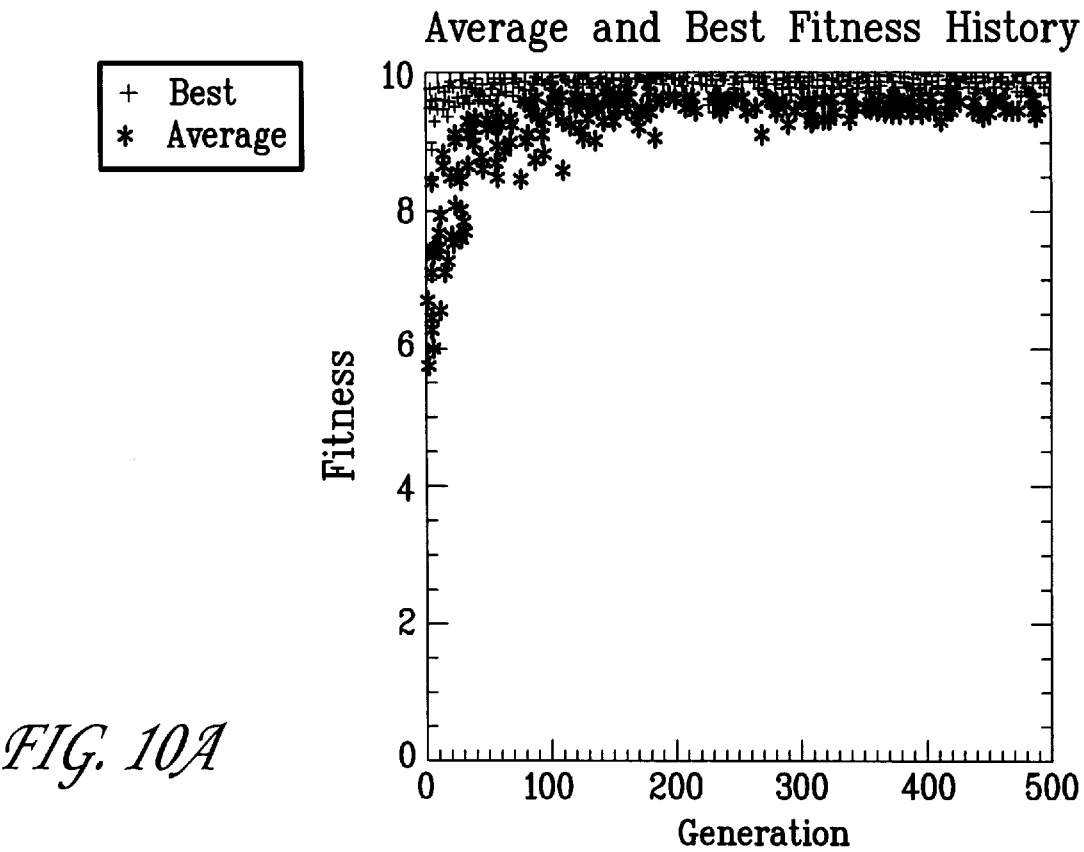
FIGS. 10A–10F are a series of plots showing the evolution of a series of 24 patches on toluene, xylene and methanol.
Figure 10B:
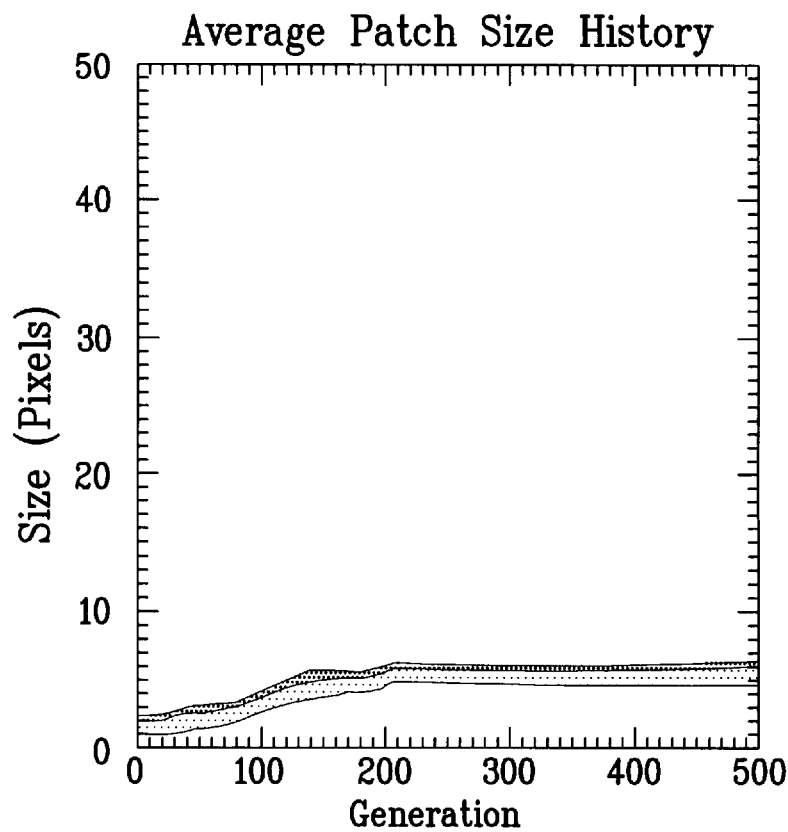
Figure 10C:
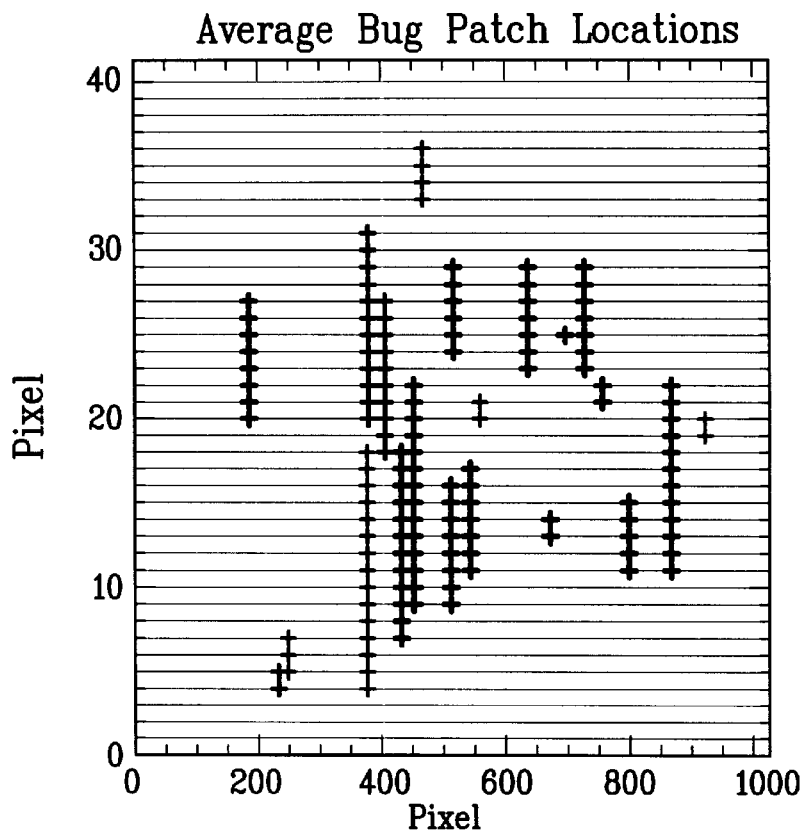
Figure 10D:
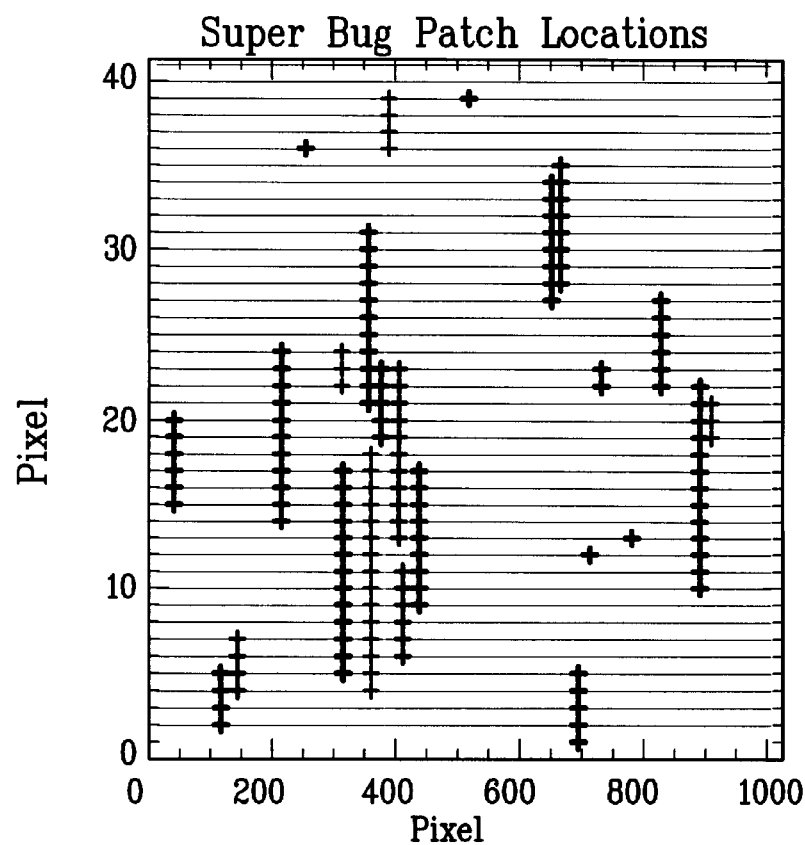
Figure 10E:
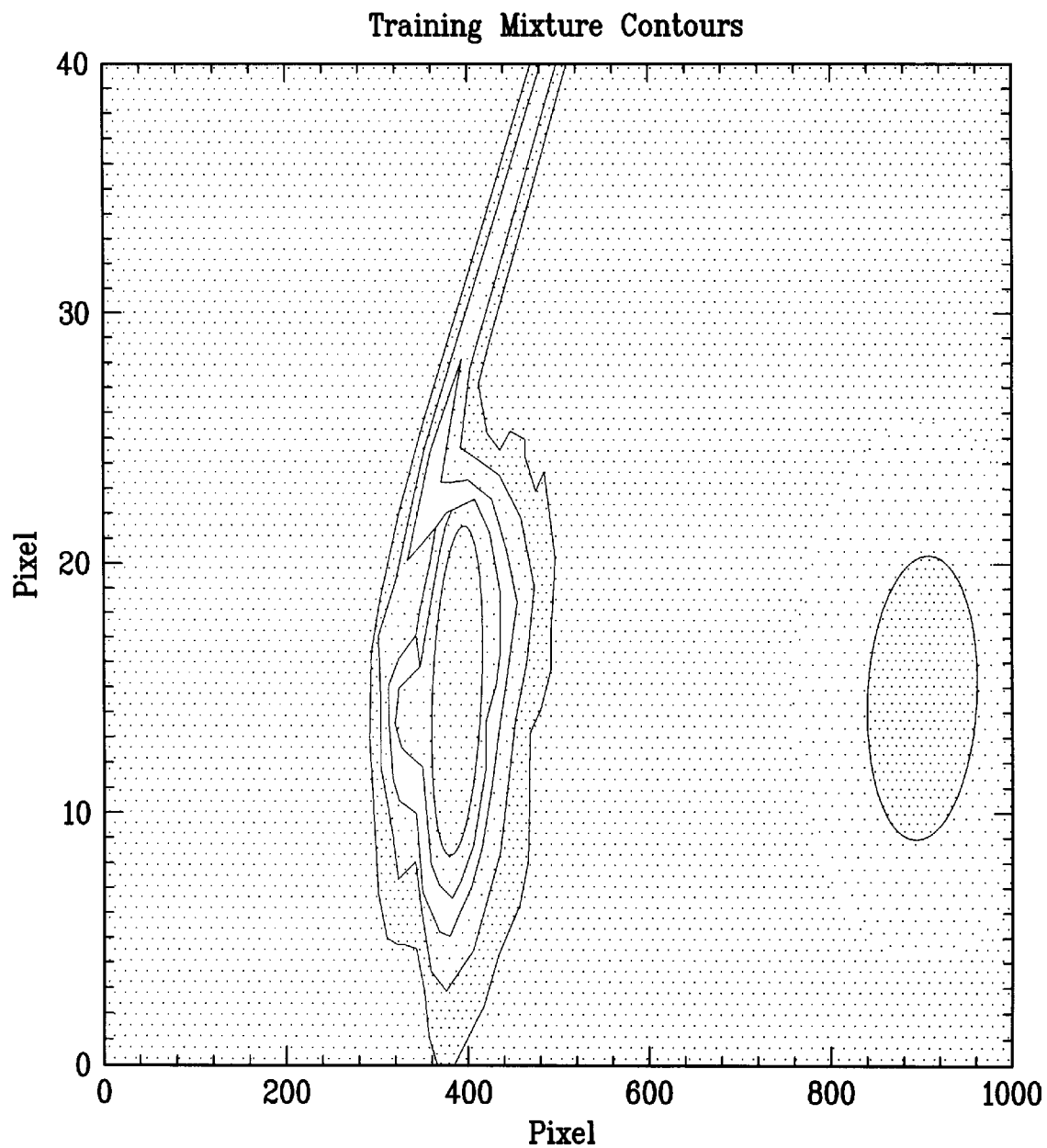
Figure 10F:
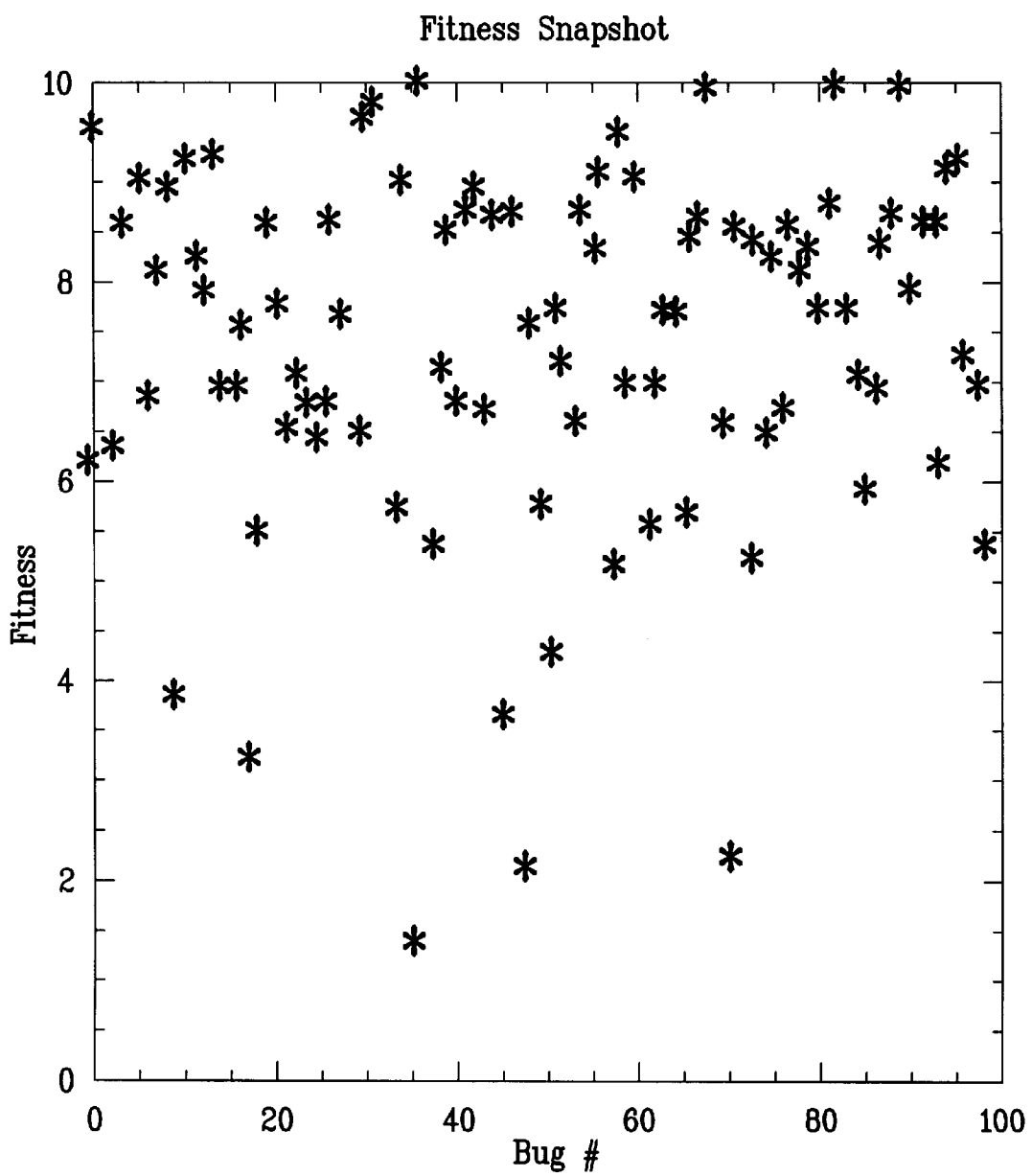

FIGS. 10A, 10B, 10C, 10D, 10D and 10F illustrate a GA optimizing 24 patches on toluene, xylene, and methanol. The upper left panel, FIG. 10A, is a historical plot over 500 generations of the average fitness (lower curve) and superbug fitness (upper curve). A superbug is the most fit bug in a generation. The fitness is defined so that a perfect bug gets a 10. The middle upper panel, FIG. 10B, is a history of the patch size. The fact that the curve flattens out is a good indication the GA had found the optimal solution after about 200 generations. The right upper panel, FIG. 10C, shows the location of the 24 patches corresponding to an 'average' bug. The patches are not really as distorted as the figure indicates. There is a severe aspect ratio distortion since there are 41 rows and 1024 columns of pixels. There are 100 bugs competing in each generation. The lower left panel, FIG. 10D, shows the superbug patches after 500 generations. Experience has taught that it is usually better to use the average solution rather than the super solution since the average is adapted to a wide range of conditions whereas the super solution is adept only on a special case. The lower middle panel, FIG. 10E, shows a snapshot of the training set: a linear combination of toluene, xylene, and methanol added together using random concentrations and 10% noise added as well. The right bottom panel, FIG. 10F, is a snapshot of the fitness of all 100 bugs taken at the end of the run. The actual raw fitness is indicated by the dots at the top of the panel. The asterisks are the weighted fitnesses. Weighted fitnesses are a tool used in GA's to force competition very early and very late in the run when all bugs are almost equally fit.

It is important to note that the GA is run only once for a given application. Once the patches are found that optimally solve for a given set of chemicals, that patch set can be used over and over. Also note that a variety of strategies can be used to train the GA. For example patches can be optimized to recognize certain chemicals while at the same ignoring others and so on. It is possible to train the GA using the real system response to optimize concentration estimates while rejecting systemic distortion, noise and contaminates. In other words, the actual operating parameters of the instruments used to take the measurements can themselves be optimized as well as the configuration of the data patches.

Restating some of the major points on the evolutionary algorithm, the algorithm begins as a statement of everything necessary to solve the identification/measurement problem. Each thing or "gene" within this statement or "genetic sequence" is assigned an allowable range of numbers. A generation of given number, say 100 or 1000, of genetic sequences or "bugs" is then compared against a data set for a known material or set of known materials, and the bugs with lowest residuals are assigned higher fitness numbers. Those bugs below a certain fitness level become extinct. Of the remaining bugs, those with the higher Witnesses are allowed to reproduce and do so by exchanging gene sequences. Also, mutations are introduced into each generation. Generation by generation the bugs evolve to a point where there are no longer improving to a significant degree. At this point the optimized solution sets are determined.

This evolutionary algorithm has certain characteristics which form a unique combination of capabilities otherwise unknown in the art. As opposed to the bit stream comparisons made in the Scientific American article, this algorithm assigns a number with a variable allowed range for each measured characteristic. For the example above, three pieces of data are associated with each pixel—radiating wavelength, return wavelength and intensity of return wavelength. For the purpose of this discussion, this creates a one-dimensional mixture array, with one value associated with each pixel in the array. When the pixels are considered in patches, the array becomes two-dimensional. If one were to record more information, i.e. strength of radiating wavelength, polarization of radiating and return wavelengths, rate of attenuation of return wavelengths, etc., one will build up an n-dimensional matrix with regard to the radiation interaction with the database of known constituents. The patch algorithm is designed to handle these higher dimensions, and the evolutionary algorithm is designed to optimize it. As discussed immediately above, for each of these pieces of information or genes there is number with a assigned allowable range. This allowable range determines how much genetic mutation is allowed for that gene. This range can vary depending upon how far along the evolution of the bug has progressed. A broader range allowing greater mutations is often desirable at the beginning of the evolution while a narrower range towards the end of the evolution is often better.

Specifically, the evolutionary algorithm modifies the patches by evolving their boundaries and included pixels with their associated return signal magnitudes on the basis of a particular fitness parameter. The best patches have the highest fitnesses and are included as members of the patch database of known chemicals. The actual patch database or library of patches for known materials is made up of normalized values for the magnitudes of the measurements associated with each chemical or constituent. Determination of the actual concentrations of the known materials from the returns from the unknown mixture requires carefully calibrated information about the transmitted signal intensities, the system response characteristics and other factors to be able to translate the raw return information into concentration information. The procedure is complicated but routine.

This algorithm also provides for the optimization of more than one fitness criteria. For example, it may be desirable to have one patch set optimized for speed of determination with another optimized for accuracy. The algorithm will split the population into two populations which are then separately optimized for speed and accuracy respectively.

Chemical Recognition Using Neural Nets

As the chemical database grows one will need to intelligently choose which chemicals in the database will be actually used in the quantitative analysis. Some chemicals of interest are mission determined, but an intelligent neural net scanning the input could automate this selection, note unusual occurrences, and provide a useful double check on concentration estimates. Neural nets are attractive in the sense that they can be very fast to evaluate. A feed forward neural net has an easy to follow structure, has favorable scaling with number of chemicals (linear) and can be evaluated in a straightforward series of multiplies and adds. Neural nets do not require an iterative solve or a matrix inversion as do multivariate methods. The disadvantage of a neural net is that it is difficult to construct (train), and does not provide a rigorous uncertainty estimate. These deficiencies may someday be relaxed as research in neural nets continues at a rapid pace. A neural net designed for chemical recognition is potentially quite different from neural nets used in pattern recognition, which are basically classifiers. In the chemical recognition problem similar spectra are superimposed, so instead of asking 'what letter is this?', one is asking 'how much of every letter?', is superimposed on top of every other in the image.

Figure 11:
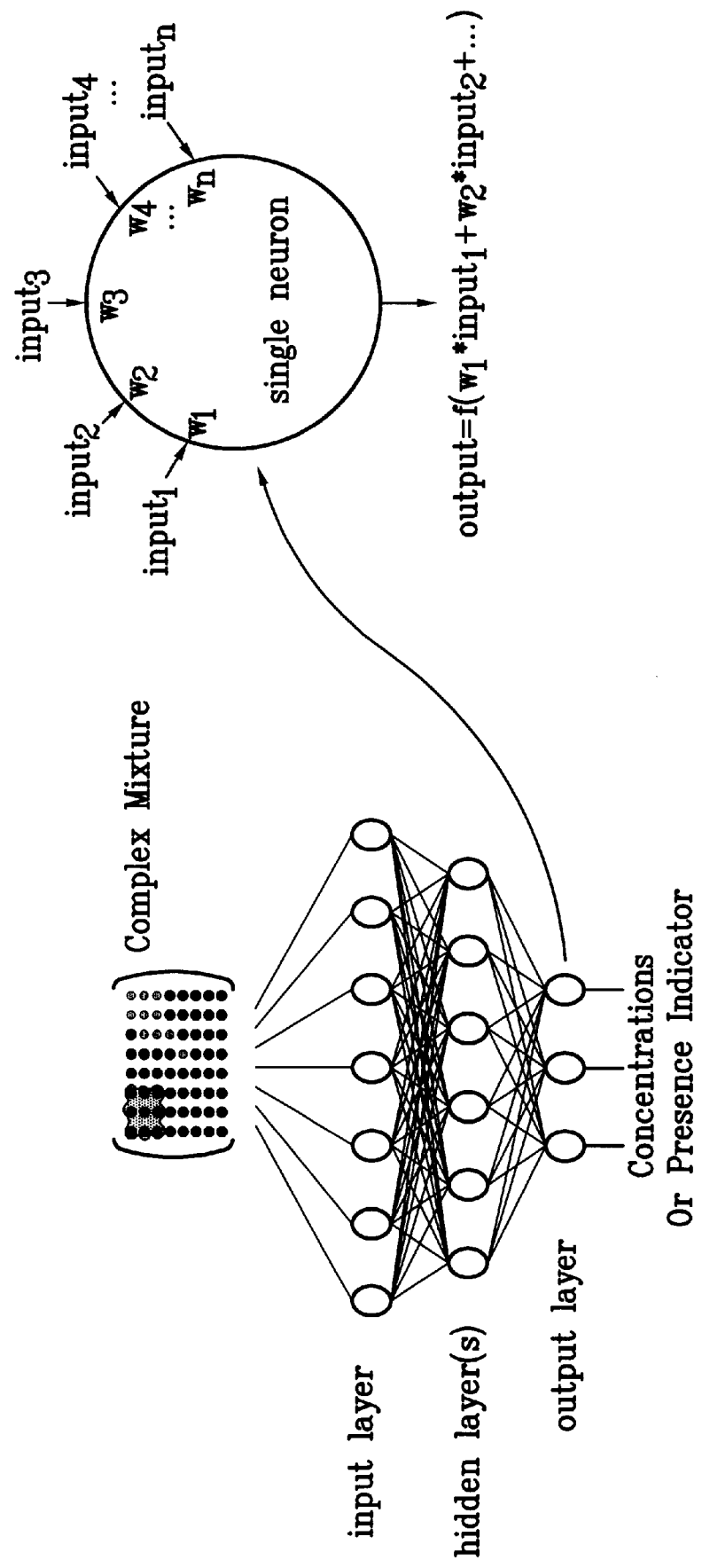
FIG. 11 is a diagram of a typical neural network used herein with each pixel of the complex mixture return being uniquely connected to one neuron in the input layer, the various interconnections between the neurons in the various layers and the single outputs from the neurons in bottom layer, with a detailed inset of one of the bottom layer neurons with the weights associated with the input connections to it and its single output as the summation of the inputs multiplied by their respective weights.

I have developed a new genetically trained neural net for chemical recognition, as shown in FIGS. 11 and 12. The most common training technique of neural nets is back propagation. The novel use of a genetic algorithm to train the net has advantages in that a GA can also design the net. There may well be speed and accuracy advantages compared to the conventional back propagation training method.

FIG. 11 illustrates a typical neural network for this application. It has inputs of the return data of the response of a complex unknown mixture to the input radiation. Each of the pixels from the apparatus receiving the return information is connected to one of the neurons in the top layer with a single input connection with each such input being multiplied by a weight. Each input layer neuron has a separate connection to each of the neurons in the next layer down, again with each connection having a weight multiplier associated with it at the receiving neuron. This intermediate or hidden layer could be only one layer or could be a stack of n layers. This intermediate stage of layers (or just a single intermediate layer) is similarly connected to an output layer of neurons. Each neuron in this layer has only a single output which, as in the outputs of the neurons in the layers above is a function of the sum of all the individual inputs to a particular neuron multiplied by the weights associated with each of the individual inputs. A final layer, not shown, computes the concentrations or presence of various known chemicals.

Figure 12A:
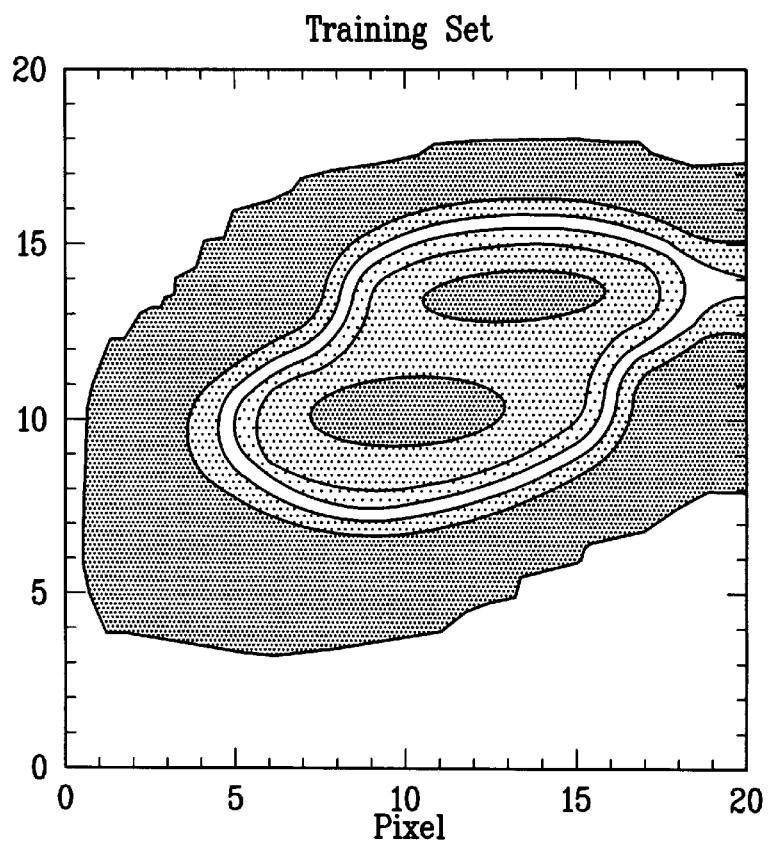
FIGS. 12A–12F are a series of plots which show the evolution of a four layer neural network at the time of the 50th generation.
Figure 12B:
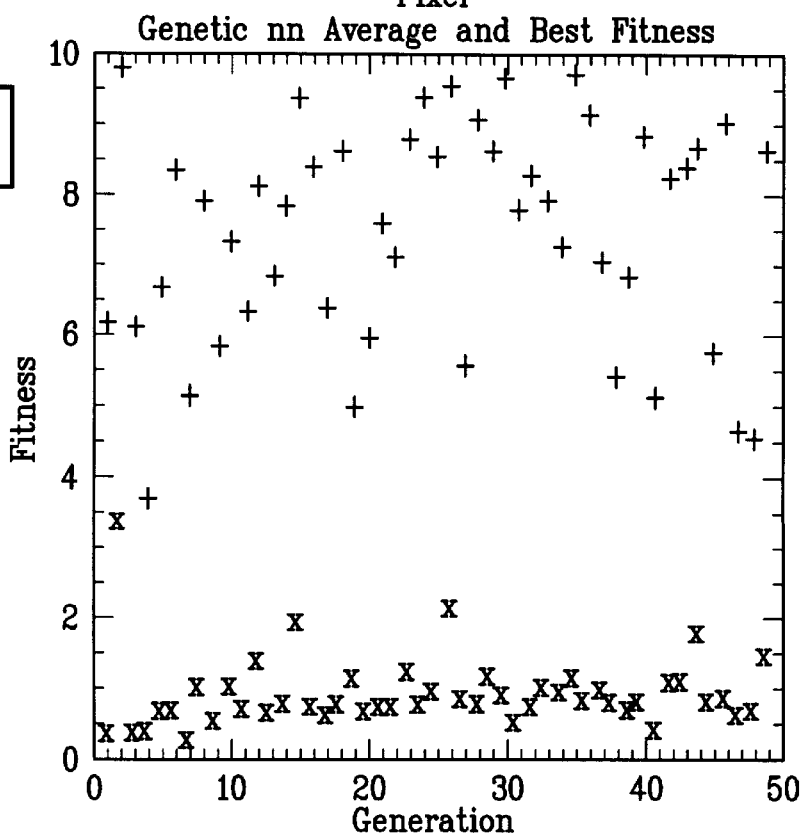
Figure 12C:
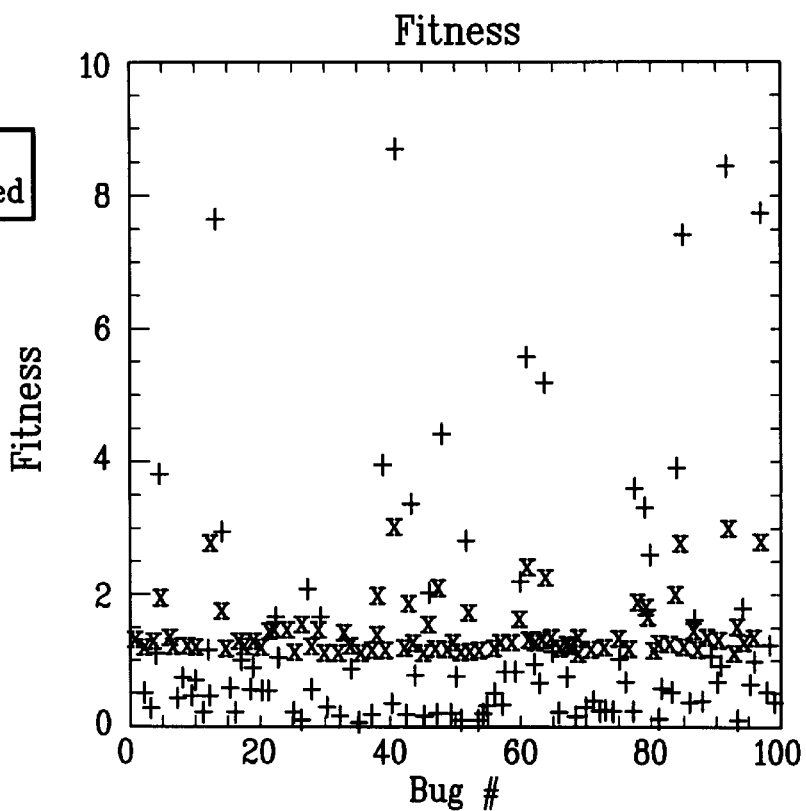
Figure 12D:
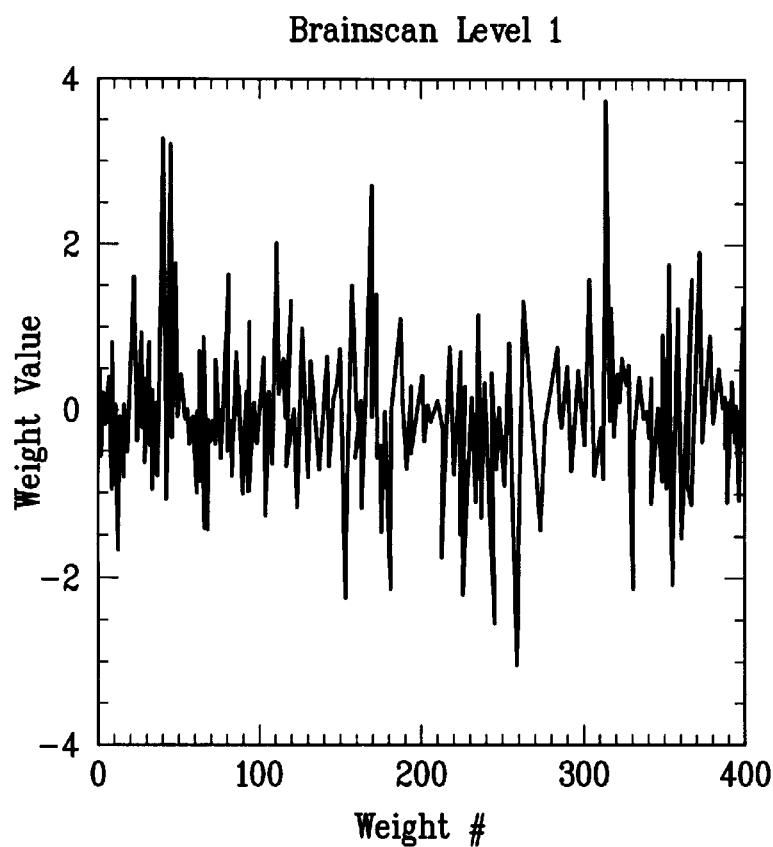
Figure 12E:
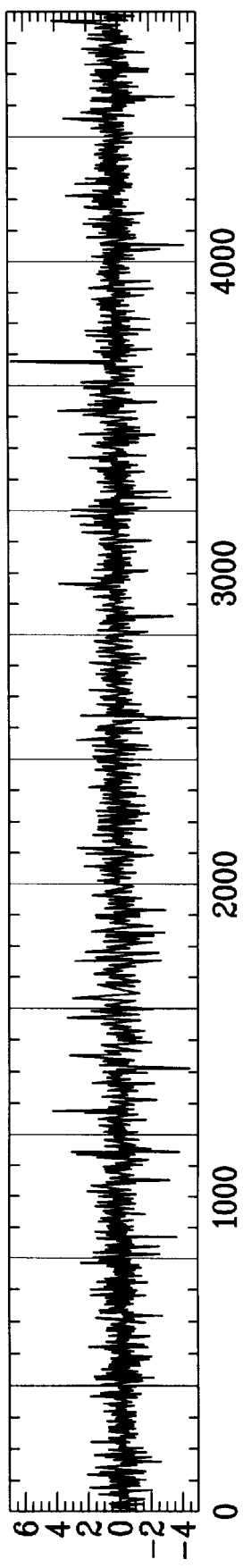
Figure 12F:
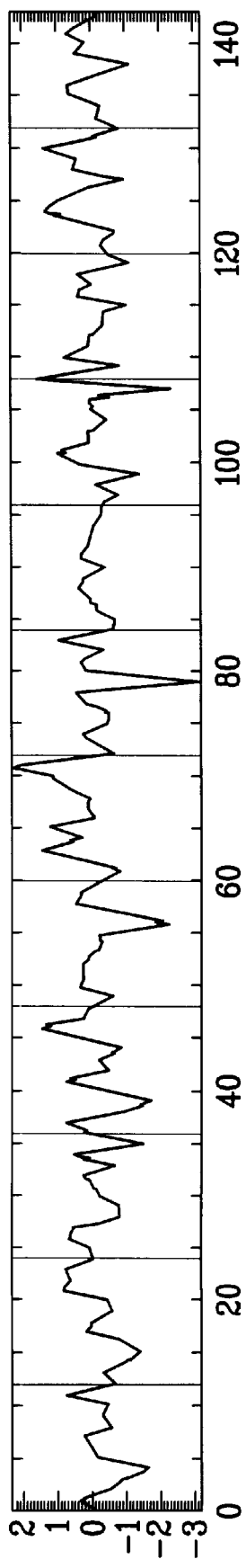
Figure 13A:
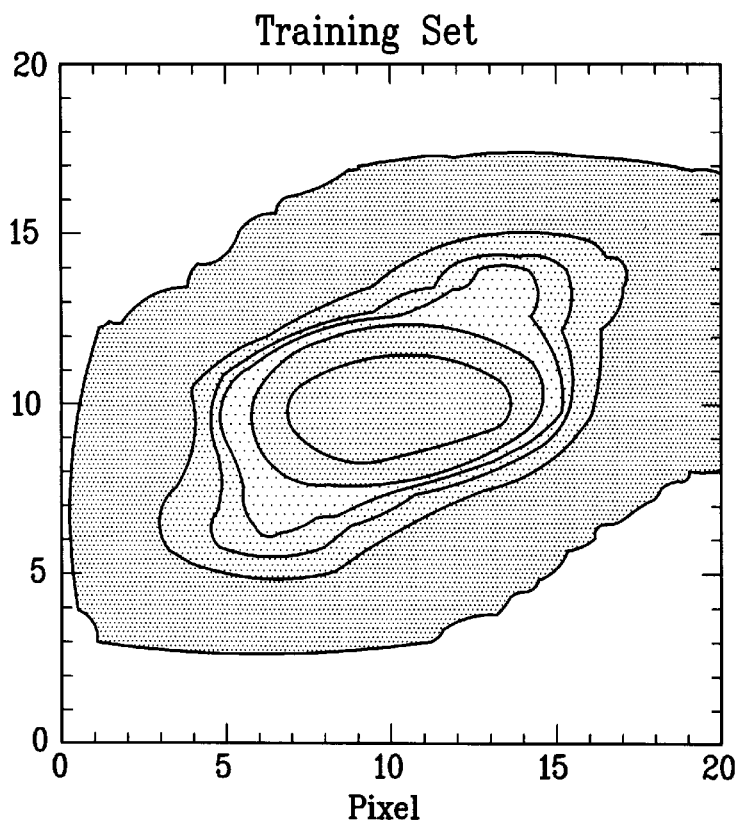
FIGS. 13A–13F correspond to the plots of FIGS. 12A–12F but the data come from the neural network genetic sequences at the 3000th generation.
Figure 13B:
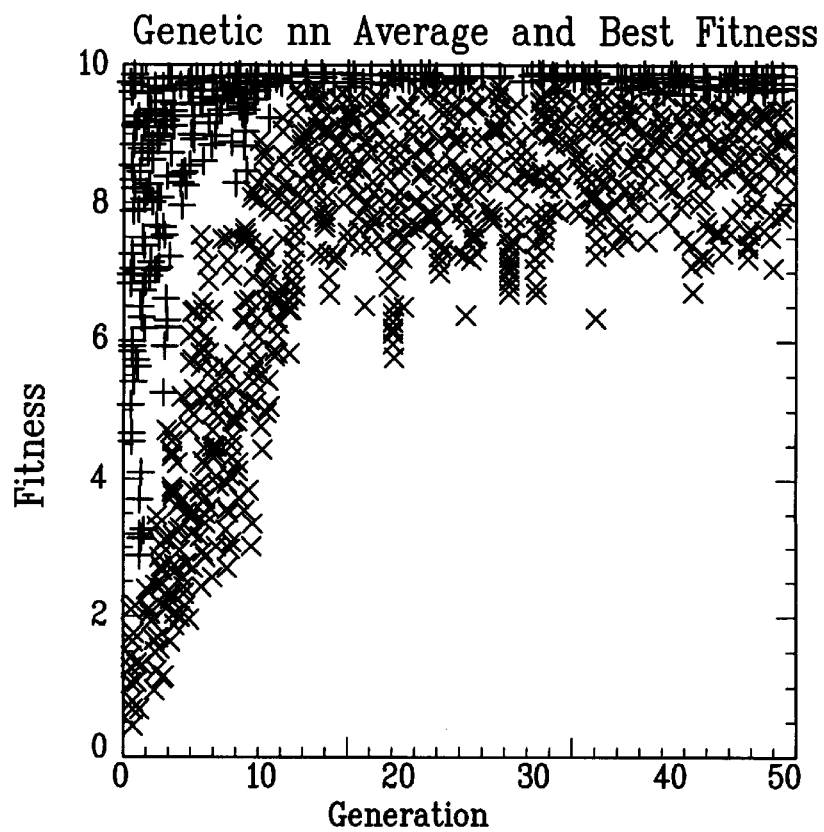
Figure 13C:
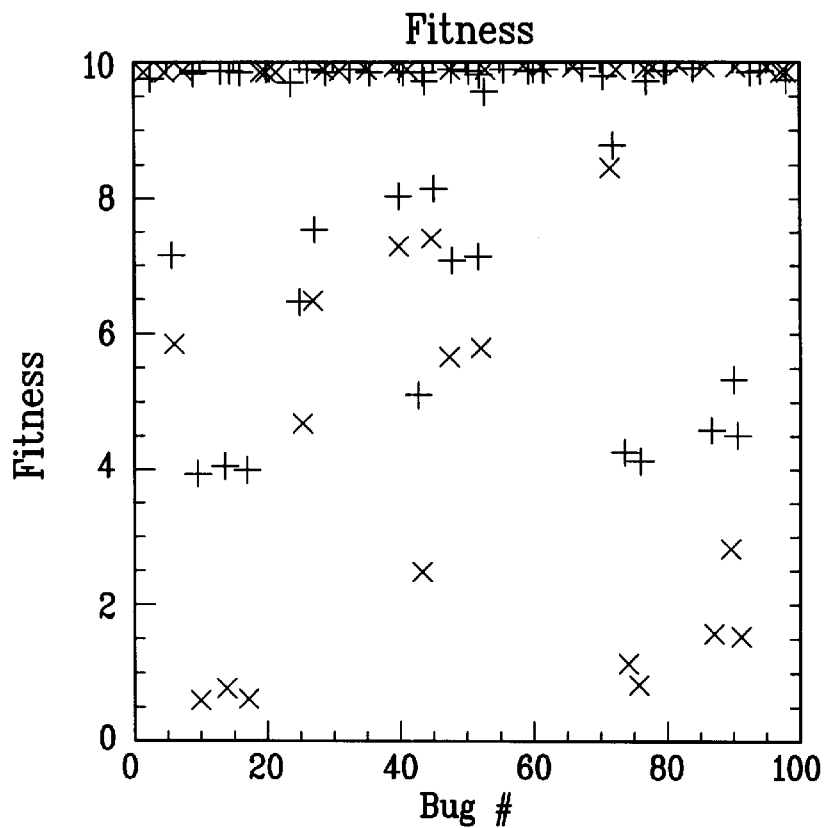
Figure 13D:
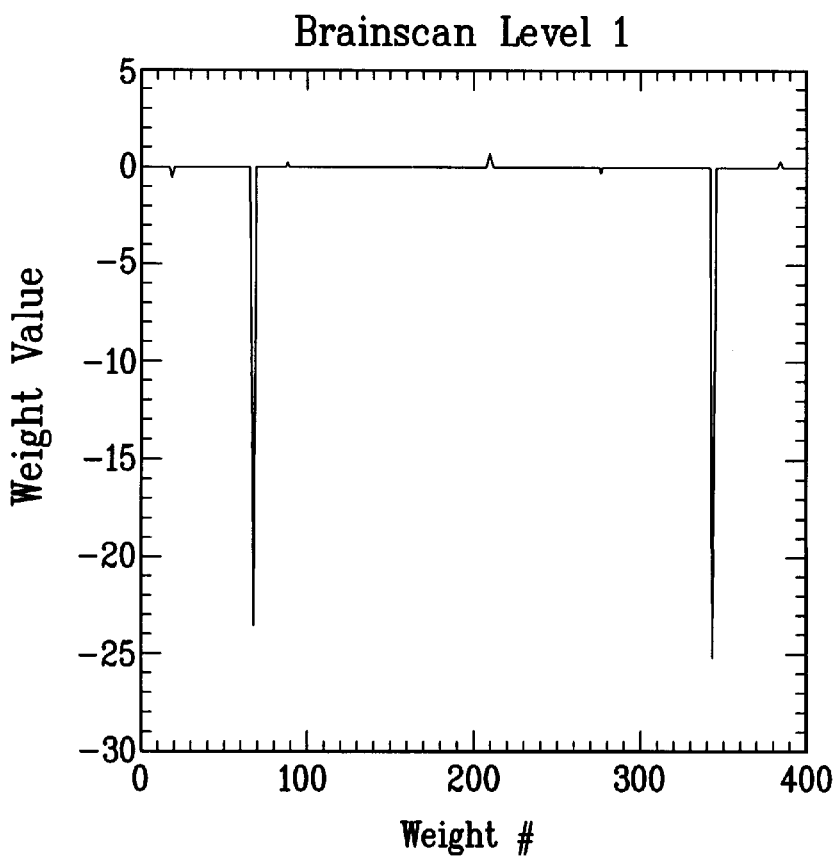
Figure 13E:
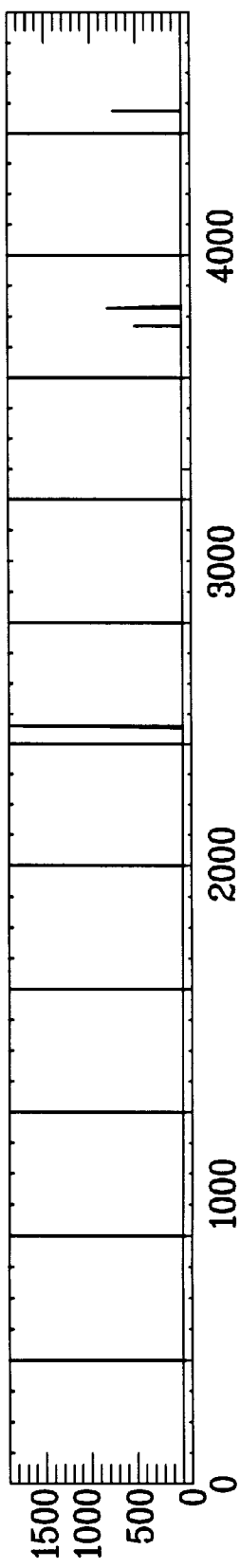
Figure 13F:
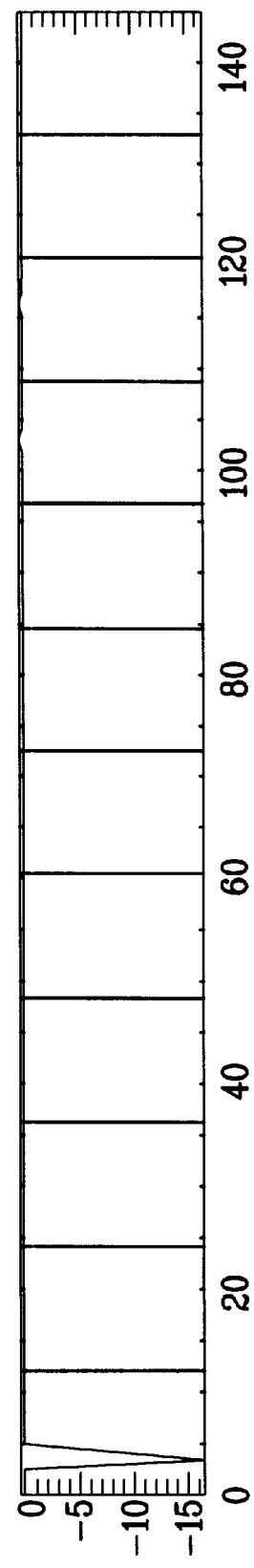

In FIGS. 12A, 12B, 12C, 12D, 12E and 12F, a 4 layer neural net is training on three gaussian-shaped chemicals along the diagonal, similar to the test case displayed in the earlier FIGS. 6A, 6B, 6C, 6D and 6E. The upper left panel, FIG. 12A, is a snapshot of the training set used during generation 50. The training set is recomputed every generation, using a different set of concentrations for each of the three chemicals, chosen randomly between 0.0, and 1.0. The second panel, FIG. 12B, on the top row is a history of the raw fitness throughout the first fifty generations. The lower curve is the average fitness of all the 100 nets that are competing in each generation, while the top points are the fitness of the superbug at each generation. The gap between the superbugs and the average population is an indication that the general population has a lot of learning to do. The good performance of a superbug compared to the average on these early training sets indicates that it is too overspecialized for a particular special case. The next panel, FIG. 12C, is a snapshot of the raw and scaled fitness at generation 50. The right most panel, FIG. 12D, is a plot of the weights on all 400 neurons in the topmost layer. The weights are initially random, and are not showing much structure this early in the training session. The middle panel, FIG. 12E, plots the 400 weights of each of the 12 neurons in the second layer for a total of 4800 weights. The bottom panel, FIG. 12F, plots the 12 weights of each of the 12 neurons in the bottom layer for a total of 144 weights. The bottom 4th layer is not plotted; its output is the nets concentration estimates and is used to compute the fitness.

FIGS. 13A, 13B, 13C, 13D, 13E and 13F show the same net after 3000 generations. The fitness of both the superbugs and the overall population are achieving fitnesses over 8, which is very good. The population is still learning at this point, and its ultimate capability can improve still further. Notice the plots of the weights now exhibit considerable structure; the information in certain pixels being amplified and differentiated by the net, while other pixels are multiplied by zero and are effectively discarded.

Figure 17:
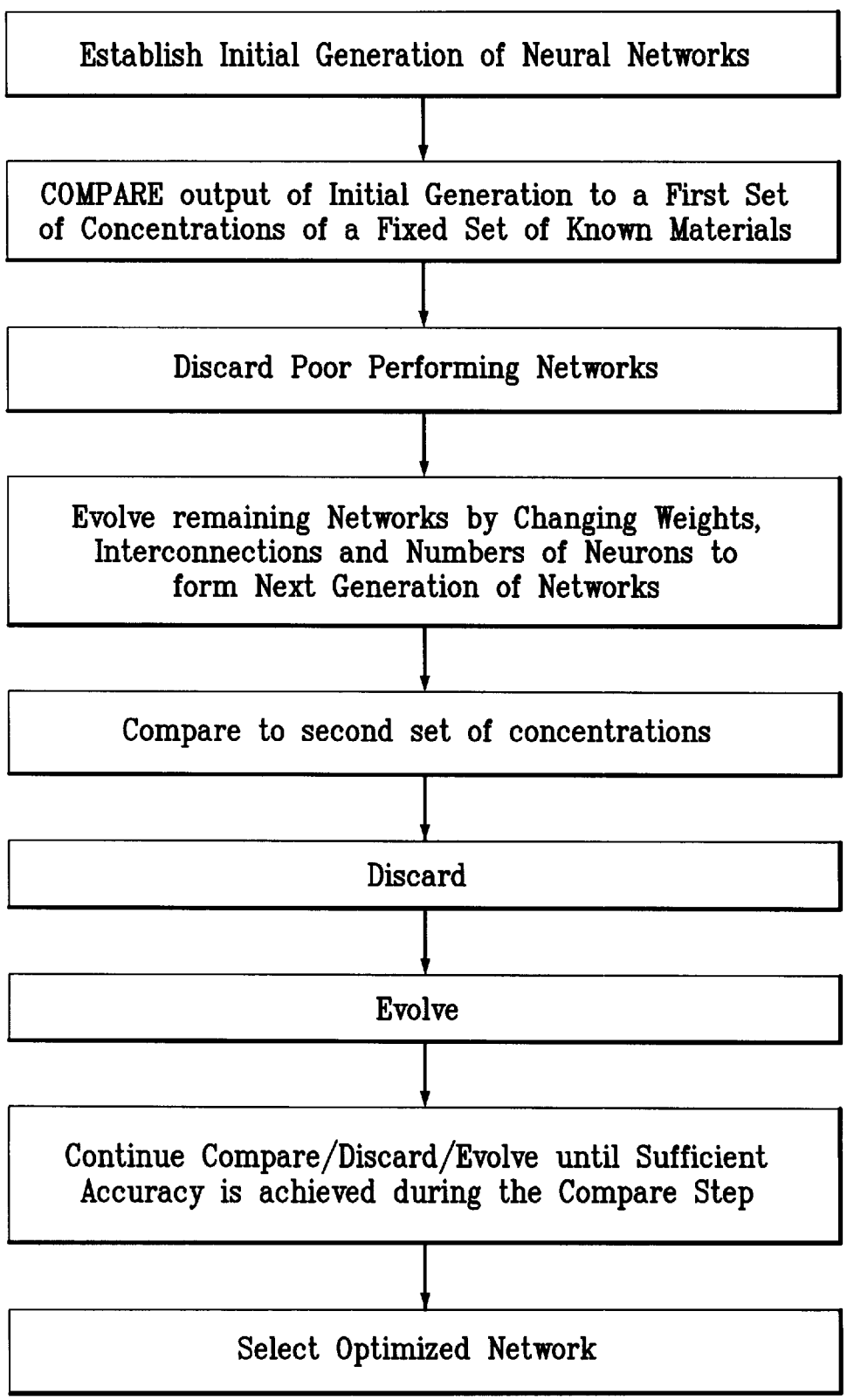
FIG. 17 is a flow chart showing the steps by which the optimized neural network is created by the evolutionary algorithm.

The evolutionary algorithm as applied to the neural net is also somewhat of a departure from the standard practice. This evolutionary algorithm has the capability to alter the number of neurons in a layer and also the interconnects between layers by "pruning" out those interconnection with zero weight multipliers. It also has the capability to mutate the neural net by adding in neurons and interconnections with initially random weights. While the neural network is initially assigned a structure with a given number of layers and neurons, the evolutionary algorithm takes control over its structure once it starts running. The net is trained by supplying a different training set (the same combination of known samples but at different concentrations) to the net at each generation and evolving the weights and interconnections of the net on the basis of the fitness of the various bugs in each generation in much the same fashion as for the patch technique discussed above. The process by which the optimized neural network is created is illustrated by FIG. 17.

Figure 14:
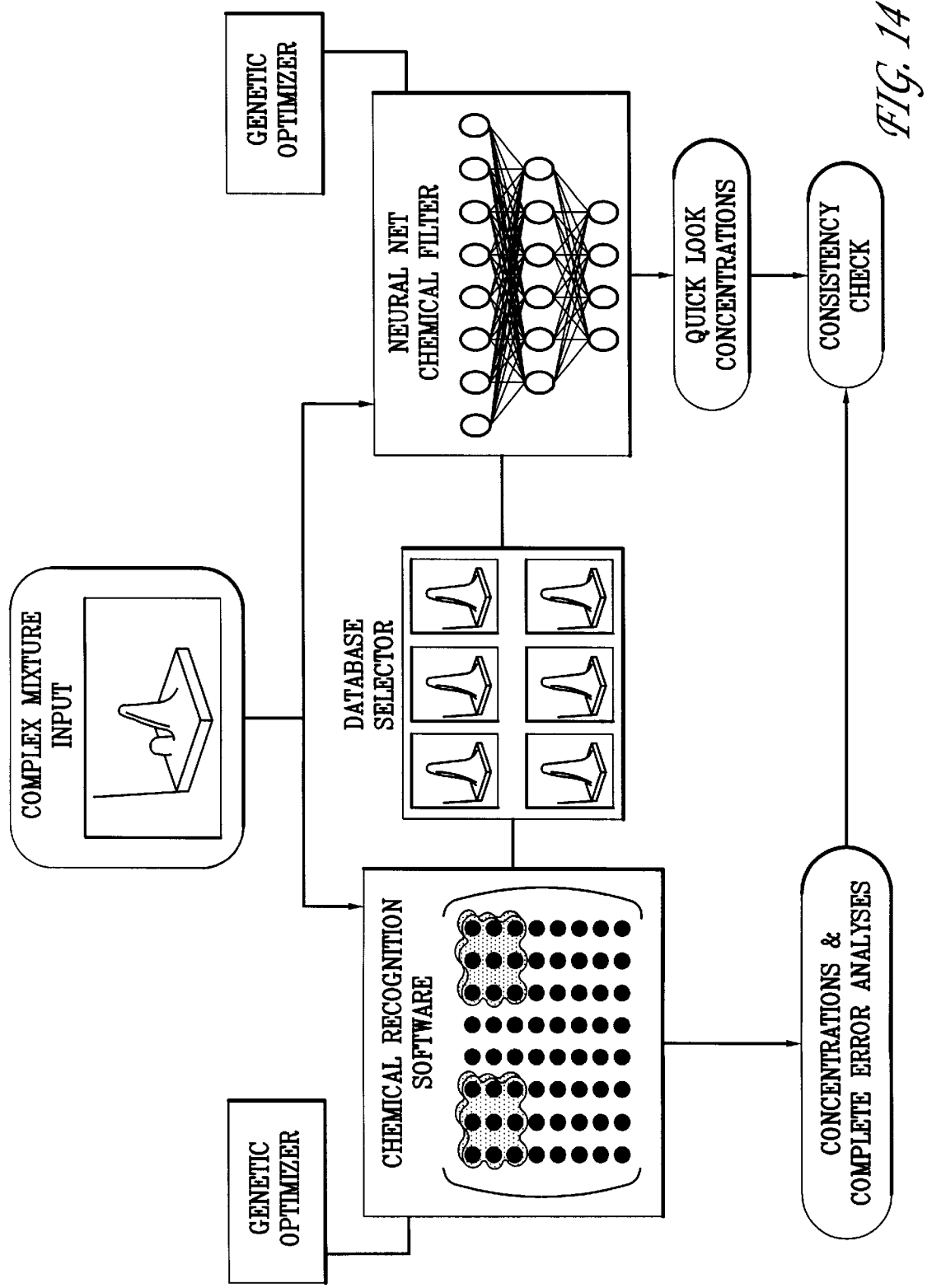
FIG. 14 is a flow chart showing the composition and operation of the elements of an expert system incorporating the multivariate patch algorithms and neural networks trained by the evolutionary algorithm.

The genetically trained multivariate analysis patch technique can be combined with the genetically trained neural net to form a powerful expert system organized as in FIG. 14. The data received from the sensors would be fed initially into the neural net which will quickly identify the most important constituents in the mixture and estimate their concentrations. The net would hand off the candidate list from the chemical database to the multivariate processor which then utilizes this list in addition to any user-specified chemicals for analysis and uncertainty estimates. The pre-screen by the neural net cuts down the workload for the multivariate analysis data processing significantly. Also a comparison of the concentration estimates from the neural net with the output of the multivariate processing is a very useful consistency check.

Other Applications of the Invention

The technique of the first preferred embodiment has also been applied to the problem of recognition of microorganisms in a biologic sample. As with the example above, uv laser induced fluorescence spectra were analyzed for *E. coli* bacteria in a bovine serum albumen mixture. The system was able to recognize the *E. coli* bacteria spectral signature and estimate the concentration. This has immediate applications for detection of food contamination and also for diagnostic use by medical personnel for the presence of pathogens in or on a patient. A suitably packaged system could be used to diagnose a streptococcus infection in a patient's throat. It could also be used to search for biologic contamination in hospital operating rooms and on sterile equipment. Indeed a suitably trained database could recognize subtle genetic variations between samples of DNA or could provide an early detection method for cancerous or otherwise abnormal cells on the basis of any characteristic of the subject cells that can be distinguished on the basis of the interaction of the radiation with those cells.

Other uses of the techniques disclosed herein will find use in a variety of areas. Petrochemical industries have a particular need to continuously monitor the composition of materials in pipelines and feedstocks. As agriculture refines its usage of fertilizers and pesticides further, the invention could be used as a real time monitor of the fertilizer/pesticide content of a field in the pathway of an application vehicle and to direct a system on the vehicle to apply the fertilizer/pesticide onto only those portions of the field that need it.

Figure 16:
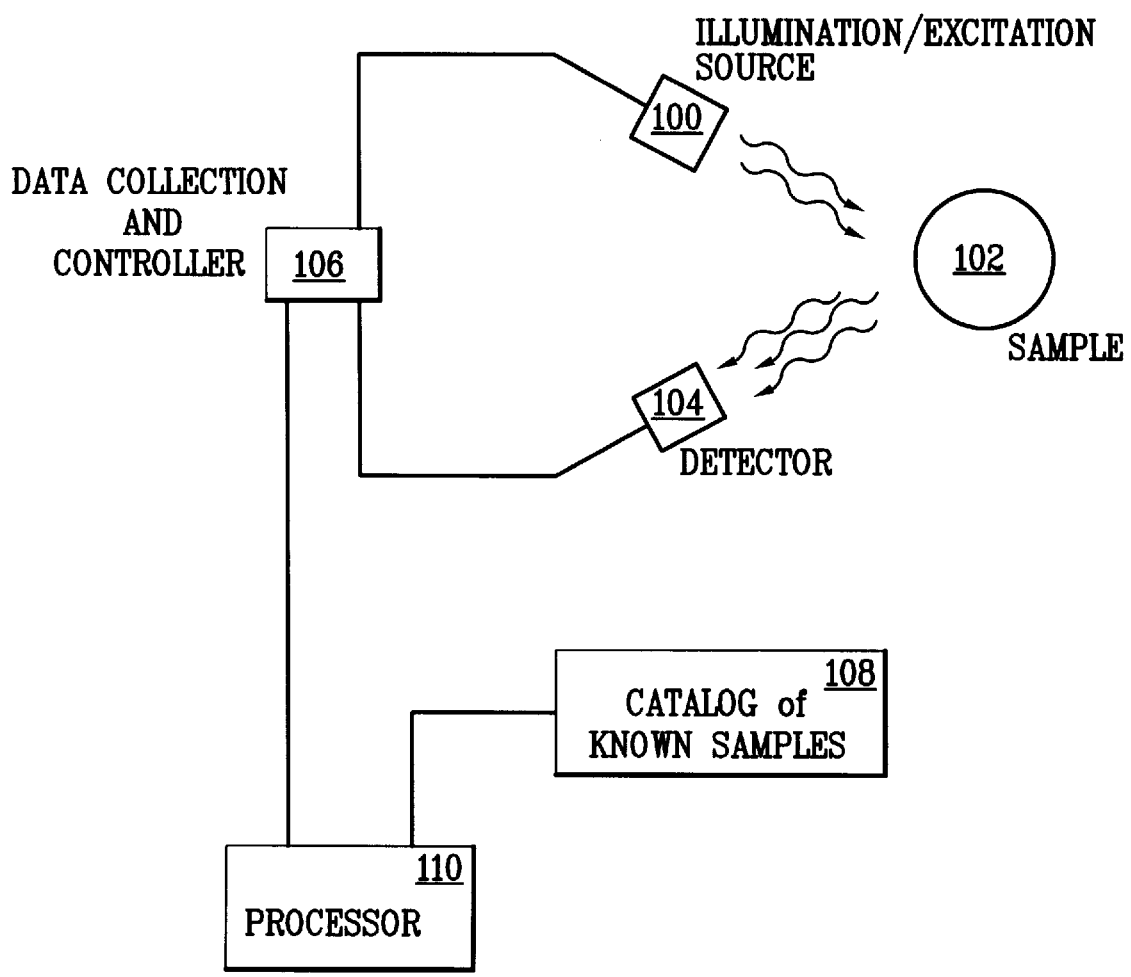
FIG. 16 is a schematic diagram of the hardware layout of the system.

Returning to the hardware and the physics of the invention, the first preferred embodiment utilized uv fluorescence spectroscopy to analyze the mixtures. This inelastic process is useful only with relatively complicated molecules. As was discussed above, this technique will work with any radiative interaction with a material that provides a return that somehow serves to distinguish the material of interest. Both elastic and inelastic interactions can be measured and used herein. Elastic interactions occur with all materials when irradiated with electromagnetic waves. However, these effects are often more subtle than the inelastic measurements and are sometimes nothing more distinct than a small shift in the lifetime of the return pulse at various return wavelengths as the difference between two materials. More robust effects are absorption, changes in polarization, and resonance Raman spectroscopy. For the uv spectroscopy, two different types of sources can be used. A flash lamp with various bandpass filters can be used as a low resolution source. A tunable laser operating between 200 and 400 nm is a good high resolution source. It is not necessary to use the very same source for the creation of the chemical database and for the actual measurement of the unknown mixture so long as the electromagnetic waves are provided at the same frequencies. As was mentioned above, very careful attention must be paid to calibrating all of the data generation equipment. The hardware used in the system is shown schematically in FIG. 16. An illumination/excitation source 100 is used to irradiate the sample 102. The energy coming out of the sample is collected by a detector 104. The source and detector are controlled by and the data are collected by the data collection and controller 106. The collected data are sent to the processor 110. If the known samples are being run for the first time, the catalog of their optimized responses are stored in the catalog of known samples 108 as a product of the processors operations on the data. However, if this step has already been done, the catalog of known samples is referred to by the processor when determinations about an unknown sample are being made.

The remainder of this discussion is devoted to the mathematics underlying the invention.

1.0 Algorithm 1.1 'Traditional' 1-D Chemometrics

In this section we develope a formalism for a algorithm to estimate chemical concentrations contained in a complex mixture. We assume that each chemical sample has a unique 1-D spectral signature, and we have a set of these spectral signatures saved in a reference database set. We assume the mixture, or unknown is made up of a linear combination of the chemicals in the database. The purpose of this section is to solve the problem in a conventional way for comparison to the more sophisticated methods in 1-D, 2-D, and 3-D developed in subsequent sections. For now we assume the mixture, or unknown, is a 1-D linear array of values which represent a measurement.

Figure 15:
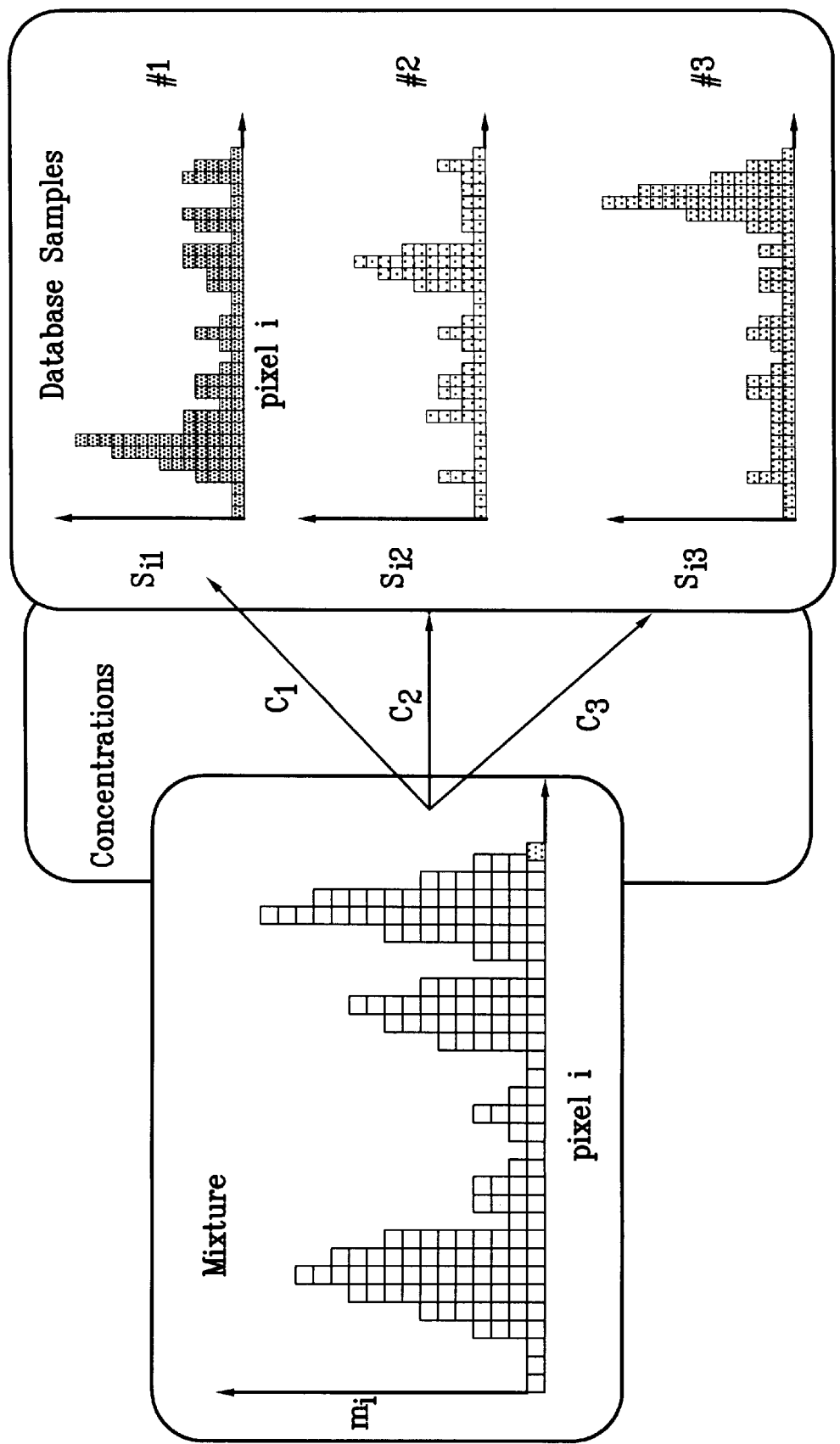
FIG. 15 is a diagram illustrating how the concentrations of the various constituents add to form the mixture returns in a one-dimensional pixel array.

FIG. 15 represents how the magnitudes associated with the pixels for each sample in the database multiplied by their concentrations add up to the measurements from what is shown here as a mixture of the three samples with no noise.

In our application the measurement will be a UV fluorescence intensity taken at a variety of emission wavelengths, but the general approach described here is valid for any measurement curve that is a mixture of other curves.

For convenience we will frequently refer to the elements of the mixture and sample arrays as pixels. Each pixel has a value or intensity. The 1-D mixture array M with n pixels $m_1\ m_2\ m_3\ \ldots\ m_n$ will be represented by a matrix with one row, $$[M]=[m_1\ m_2\ m_3\ \ldots\ m_n]. \quad (1.1\text{-}1)$$

Each chemical sample $S_1$ with n pixels $s_{1l}\ s_{2l}\ s_{3l}\ \ldots\ s_{nl}$ will also be represented by a matrix with one row, as in $$[S_l]=[s_{1l}\ s_{2l}\ s_{3l}\ \ldots\ s_{nl}]. \quad (1.1\text{-}2)$$

The second subscript l (l=0,1,2, . . . , $N_s$) is the chemical identifier. There are a total of $N_s$ chemicals in the database.

Since [M] is assumed to be made up of a linear combinations of the samples, [M] can be written schematically as:

$$[M]=C_1[S_1]+C_2[S_2]+C_3[S_3]+\ldots+C_{N_l}[S_{N_l}]+\text{residuals.} \quad (1.1\text{-}3)$$

The residuals can be considered a combination of measurement uncertainties such as calibration uncertainties, signal and instrument effects, noise, filtering, and the presence of chemicals in the mixture which are not in the database. Writing out equation 1.1-3 fully results in the equation, $$[m_1\ m_2\ m_3\ \ldots\ m_n]=C_1[s_{1l}\ s_{2l}\ s_{3l}\ \ldots\ s_{nl}]+C_2[s_{12}\ s_{22}\ s_{32}\ \ldots\ s_{n2}]+\ldots+\text{residuals.} \quad (1.1\text{-}4)$$

Now to solve for the concentrations $C_1, C_2, C_3 \ldots C_l \ldots C_{N_l}$ we will use a least squares minimization approach. We define $$\delta_i^2 = \left(\frac{m_i - C_1 s_{i1} - C_2 s_{i2} - C_3 s_{i3} - \ldots - C_{N_s} s_{iN_s}}{\sigma_i}\right)^2, \quad (1.1\text{-}5)$$

where $\delta_i^2$ is the weighted squared residual for pixel i. The weight $\sigma_i$ can be interpreted in many ways. For our applications the weights $\sigma_i$ will frequently be the uncertainty estimates for mixture measurements of each pixel, i.e.

$$\sigma_i \approx \delta m_i \approx \frac{1}{\sqrt{n_i}}$$

$n_i$=# measurements of $m_i$. Another interpretation of $\sigma_i$ has to do with the 'value' of that pixel. We will explore the use of this interpretation in follow on reports dealing with the genetic algorithm optimizations. In many cases for simpler problems, and for interesting limiting cases, the weights can be simply set to one and ignored, with excellent results.

Now to solve for the concentrations, we minimize the sum of the squared weighted residuals, $$\chi^2 = \sum_{i=1,n} \delta_i^2 \quad (1.1\text{-}6)$$

$$= \sum_{i=1,n} \left(\frac{m_i - C_1 s_{i1} - C_2 s_{i2} - C_3 s_{i3} - \ldots - C_{N_s} s_{iN_s}}{\sigma_i}\right)^2.$$

It is worth noting here the choice of this functions to minimize is arbitrary, and many other choices exist. We will explore this more later in this report. In the literature minimizing the sum of the squares is the classical least squares method, while minimizing the sum of the absolute values results in a 'robust estimation' method that is less sensitive to out lying points, but the robust method is frequently solvable only by iterative means. There are many other interesting modifications to the minimization function "Numerical Recipes: The Art of Scientific Computing", W. H. Press et al., Cambridge University Press, 1986.

To minimize $\chi^2$, equation 1.1-6 is differentiated with respect to each of the concentrations;

$$\frac{\partial}{\partial C^1}\chi^2 \to 0 \Rightarrow \quad (1.1\text{-}7a)$$

$$\sum_{i=1,n} \left[2\left(\frac{m_i - C_1 s_{i1} - C_2 s_{i2} - C_3 s_{i3} - \ldots - C_{N_s} s_{iN_s}}{\sigma_i}\right)\left(\frac{-s_{i1}}{\sigma_i}\right)\right] = 0,$$

$$\frac{\partial}{\partial C^2}\chi^2 \to 0 \Rightarrow \quad (1.1\text{-}7b)$$

$$\sum_{i=1,n} \left[2\left(\frac{m_i - C_1 s_{i1} - C_2 s_{i2} - C_3 s_{i3} - \ldots - C_{N_s} s_{iN_s}}{\sigma_i}\right)\left(\frac{-s_{i2}}{\sigma_i}\right)\right] = 0,$$

$$\frac{\partial}{\partial C^3}\chi^2 \to 0 \Rightarrow \quad (1.1\text{-}7c)$$

$$\sum_{i=1,n} \left[2\left(\frac{m_i - C_1 s_{i1}^1 - C_2 s_{i2} - C_3 s_{i3} - \ldots - C_{N_s} s_{iN_s}}{\sigma_i}\right)\left(\frac{-s_{i3}}{\sigma_i}\right)\right] = 0,$$

$$\ldots, \quad (1.1\text{-}7d)$$

$$\frac{\partial}{\partial C^{N_s}}\chi^2 \to 0 \Rightarrow \sum_{i=1,n} \left[2\left(\frac{\begin{array}{c}m_i - C_1 s_{i1} - C_2 s_{i2} - \\ C_3 s_{i3} - \ldots - C_{N_s} s_{iN_s}\end{array}}{\sigma_i}\right)\left(\frac{-s_{iN_s}}{\sigma_i}\right)\right] = 0. \quad (1.1\text{-}7e)$$

Equations 1.1-7a to 1.1-7e can be rewritten as (with the factor 2 divided out), $$\sum_{i=1,n} \frac{m_i s_{i1}}{\sigma_i^2} - C_1 \sum_{i=1,n} \frac{s_{i1} s_{i1}}{\sigma_i^2} - C_2 \sum_{i=1,n} \frac{s_{i2} s_{i1}}{\sigma_i^2} - \quad (1.1\text{-}8a)$$

$$C_3 \sum_{i=1,n} \frac{s_{i3} s_{i1}}{\sigma_i^2} - \ldots C_{N_s} \sum_{i=1,n} \frac{s_{iN_s} s_{i1}}{\sigma_i^2} = 0,$$

$$\sum_{i=1,n} \frac{m_i s_{i2}}{\sigma_i^2} - C_1 \sum_{i=1,n} \frac{s_{i1} s_{i2}}{\sigma_i^2} - C_2 \sum_{i=1,n} \frac{s_{i2} s_{i2}}{\sigma_i^2} - \quad (1.1\text{-}8b)$$

$$C_3 \sum_{i=1,n} \frac{s_{i3} s_{i2}}{\sigma_i^2} - \ldots C_{N_s} \sum_{i=1,n} \frac{s_{iN_s} s_{i2}}{\sigma_i^2} = 0,$$

$$\sum_{i=1,n} \frac{m_i s_{i3}}{\sigma_i^2} - C_1 \sum_{i=1,n} \frac{s_{i1} s_{i3}}{\sigma_i^2} - C_2 \sum_{i=1,n} \frac{s_{i2} s_{i3}}{\sigma_i^2} - \quad (1.1\text{-}8c)$$

$$C_3 \sum_{i=1,n} \frac{s_{i3} s_{i3}}{\sigma_i^2} - \ldots C_{N_s} \sum_{i=1,n} \frac{s_{iN_s} s_{i3}}{\sigma_i^2} = 0,$$

$$\ldots, \quad (1.1\text{-}8d)$$

$$\sum_{i=1,n} \frac{m_i s_{iN_s}}{\sigma_i^2} - C_1 \sum_{i=1,n} \frac{s_{i1} s_{iN_s}}{\sigma_i^2} - C_2 \sum_{i=1,n} \frac{s_{i2} s_{iN_s}}{\sigma_i^2} - \quad (1.1\text{-}8e)$$

$$C_3 \sum_{i=1,n} \frac{s_{i3} s_{iN_s}}{\sigma_i^2} - \ldots C_{N_3} \sum_{i=1,n} \frac{s_{iN_s} s_{iN_s}}{\sigma_i^2} = 0.$$

Now equations 1.1-8a to 1.1-8e can be rewritten to facilitate a matrix solution, $$C_1 \sum_{i=1,n} \frac{s_{i1} s_{i1}}{\sigma_i^2} + C_2 \sum_{i=1,n} \frac{s_{i2} s_{i1}}{\sigma_i^2} + \quad (1.1\text{-}9a)$$

$$C_3 \sum_{i=1,n} \frac{s_{i3} s_{i1}}{\sigma_i^2} + \ldots C_{N_s} \sum_{i=1,n} \frac{s_{iN_s} s_{i1}}{\sigma_i^2} = \sum_{i=1,n} \frac{m_i s_{i1}}{\sigma_i^2},$$

$$C_1 \sum_{i=1,n} \frac{s_{i1} s_{i2}}{\sigma_i^2} + C_2 \sum_{i=1,n} \frac{s_{i2} s_{i2}}{\sigma_i^2} + \quad (1.1\text{-}9b)$$

$$C_3 \sum_{i=1,n} \frac{s_{i3} s_{i2}}{\sigma_i^2} + \ldots C_{N_s} \sum_{i=1,n} \frac{s_{iN_s} s_{i2}}{\sigma_i^2} = \sum_{i=1,n} \frac{m_i s_{i2}}{\sigma_i^2},$$

$$C_1 \sum_{i=1,n} \frac{s_{i1} s_{i3}}{\sigma_i^2} + C_2 \sum_{i=1,n} \frac{s_{i2} s_{i3}}{\sigma_i^2} + \quad (1.1\text{-}9c)$$

$$C_3 \sum_{i=1,n} \frac{s_{i3} s_{i3}}{\sigma_i^2} + \ldots C_{N_s} \sum_{i=1,n} \frac{s_{iN_s} s_{i3}}{\sigma_i^2} = \sum_{i=1,n} \frac{m_i s_{i3}}{\sigma_i^2},$$

$$\ldots, \quad (1.1\text{-}9d)$$

$$C_1 \sum_{i=1,n} \frac{s_{i1} s_{iN_s}}{\sigma_i^2} + C_2 \sum_{i=1,n} \frac{s_{i2} s_{iN_s}}{\sigma_i^2} + \quad (1.1\text{-}9e)$$

$$C_3 \sum_{i=1,n} \frac{s_{i3} s_{iN_s}}{\sigma_i^2} + \ldots C_{N_s} \sum_{i=1,n} \frac{s_{iN_s} s_{iN_s}}{\sigma_i^2} = \sum_{i=1,n} \frac{m_i s_{iN_s}}{\sigma_i^2}.$$

Now equations 1.1-9a to 1.1-9e become the matix equation, $$\begin{bmatrix} \sum_i \frac{s_{i1}s_{i1}}{\sigma_i^2} & \sum_i \frac{s_{i2}s_{i1}}{\sigma_i^2} & \sum_i \frac{s_{i3}s_{i1}}{\sigma_i^2} & \cdots & \sum_i \frac{s_{iN_s}s_{i1}}{\sigma_i^2} \\ \sum_i \frac{s_{i1}s_{i2}}{\sigma_i^2} & \sum_i \frac{s_{i2}s_{i2}}{\sigma_i^2} & \sum_i \frac{s_{i3}s_{i2}}{\sigma_i^2} & \cdots & \sum_i \frac{s_{iN_s}s_{i2}}{\sigma_i^2} \\ \sum_i \frac{s_{i1}s_{i3}}{\sigma_i^2} & \sum_i \frac{s_{i2}s_{i3}}{\sigma_i^2} & \sum_i \frac{s_{i3}s_{i3}}{\sigma_i^2} & \cdots & \sum_i \frac{s_{iN_s}s_{i3}}{\sigma_i^2} \\ \cdots & \cdots & \cdots & \cdots & \cdots \\ \sum_i \frac{s_{i1}s_{iN_s}}{\sigma_i^2} & \sum_i \frac{s_{i2}s_{iN_s}}{\sigma_i^2} & \sum_i \frac{s_{i3}s_{iN_s}}{\sigma_i^2} & \cdots & \sum_i \frac{s_{iN_s}s_{iN_s}}{\sigma_i^2} \end{bmatrix} \begin{bmatrix} C_1 \\ C_2 \\ C_3 \\ \cdots \\ C_{N_s} \end{bmatrix} = \begin{bmatrix} \sum_i \frac{m_i s_{i1}}{\sigma_i^2} \\ \sum_i \frac{m_i s_{i2}}{\sigma_i^2} \\ \sum_i \frac{m_i s_{i3}}{\sigma_i^2} \\ \cdots \\ \sum_i \frac{m_i s_{iN_s}}{\sigma_i^2} \end{bmatrix} \quad (1.1\text{-}10)$$

Now if we define $$[\alpha] = \begin{bmatrix} \sum_i \frac{s_{i1}s_{i1}}{\sigma_i^2} & \sum_i \frac{s_{i2}s_{i1}}{\sigma_i^2} & \sum_i \frac{s_{i3}s_{i1}}{\sigma_i^2} & \cdots & \sum_i \frac{s_{iN_s}s_{i1}}{\sigma_i^2} \\ \sum_i \frac{s_{i1}s_{i2}}{\sigma_i^2} & \sum_i \frac{s_{i2}s_{i2}}{\sigma_i^2} & \sum_i \frac{s_{i3}s_{i2}}{\sigma_i^2} & \cdots & \sum_i \frac{s_{iN_s}s_{i2}}{\sigma_i^2} \\ \sum_i \frac{s_{i1}s_{i3}}{\sigma_i^2} & \sum_i \frac{s_{i2}s_{i3}}{\sigma_i^2} & \sum_i \frac{s_{i3}s_{i3}}{\sigma_i^2} & \cdots & \sum_i \frac{s_{iN_s}s_{i3}}{\sigma_i^2} \\ \cdots & \cdots & \cdots & \cdots & \cdots \\ \sum_i \frac{s_{i1}s_{iN_s}}{\sigma_i^2} & \sum_i \frac{s_{i2}s_{iN_s}}{\sigma_i^2} & \sum_i \frac{s_{i3}s_{iN_s}}{\sigma_i^2} & \cdots & \sum_i \frac{s_{iN_s}s_{iN_s}}{\sigma_i^2} \end{bmatrix}, \quad (1.1\text{-}11)$$

$$[C] = \begin{bmatrix} C_1 \\ C_2 \\ C_3 \\ \cdots \\ C_{N_s} \end{bmatrix}, \quad (1.1\text{-}12)$$

$$[\beta] = \begin{bmatrix} \sum_i \frac{m_i s_{i1}}{\sigma_i^2} \\ \sum_i \frac{m_i s_{i2}}{\sigma_i^2} \\ \sum_i \frac{m_i s_{i3}}{\sigma_i^2} \\ \cdots \\ \sum_i \frac{m_i s_{iN_s}}{\sigma_i^2} \end{bmatrix}, \quad (1.1\text{-}13)$$

Finally equation 1.1-10 can be written in the very simple form, $$[\alpha][C] = [\beta] \quad (1.1\text{-}14)$$

Or explicitly, $$\sum_{n=1,N_s} \alpha_{mn} C_n = \beta_m, \; \forall \, m = 1, N_s. \quad (1.1\text{-}15)$$

Or even using the 'repeated subscript implies summation' convention, $$\alpha_{mn} C_n = \beta_m \quad (1.1\text{-}16)$$

We are not quite done yet. The concentrations must be solved for. In this exsection the matrix $\alpha_{mn}$ is square with size $N_s$ by $N_s$. Given the typical restrictions, such as a nonzero determinant an inverse to $[\alpha]$, namely $[\alpha]^{-1}$ exits with the property $[\alpha][\alpha]^{-1} = 1$.

$[\alpha]^{-1}$ can be found in several ways. To maintain consistency with later sections of this report, SVD (Singular Value Decomposition) methods are used as follows. $[\alpha]$ can be written as the product of three special matrices, $$[\alpha] = [U] \cdot \begin{bmatrix} w_1 & & & & \\ & w_2 & & & \\ & & w_3 & & \\ & & & \cdots & \\ & & & & w_N \end{bmatrix} \cdot [V^T], \quad (1.1\text{-}17)$$

Where [U] and [V] have inverses that are their transposes. SVD algorithms are readily available see Press, et al., supra, and they provide the right hand side of 1.1-17 given $[\alpha]$. The advantages of using SVD methods are very important and have broad relevance to this problem which go beyond just providing the inverse. This will be discussed more later. Hence we get, $$[\alpha]^{-1} = [V] \cdot \begin{bmatrix} 1/w_1 & & & & \\ & 1/w_2 & & & \\ & & 1/w_3 & & \\ & & & \cdots & \\ & & & & 1/w_N \end{bmatrix} \cdot [U^T] \quad (1.1\text{-}18)$$

So that $$[C] = [V] \cdot \begin{bmatrix} 1/w_1 & & & & \\ & 1/w_2 & & & \\ & & 1/w_3 & & \\ & & & \cdots & \\ & & & & 1/w_N \end{bmatrix} \cdot [U^T] \cdot [\beta] \quad (1.1\text{-}19)$$

which is of the form, $$[C] = [V] \cdot [1/w] \cdot [U^T] \cdot [\beta] \quad (1.1\text{-}20)$$

This is the solution. The concentrations are found. Note that in many real applications, only $[\beta]$ changes with new mixtures. Therefore the inverse of $\alpha$ needs to be computed only once for a given set of sample in the edatabase. This makes repetitive estimates of concentrations extremely efficient, involving only a matrix multiply.

The question of uncertainty in concentration estimation will be deferred until later in this report. A good discussion can be found in Numerical Recipes [Press,1987, pg ?]. Basically, assuming a normal distribution of errors on the mixture the uncertainty in concentration estimates is given by the SVD inverse matrix which can be shown to be the covariance matrix. In cases were there are uncertainties in the database the situation is much more complicated, and will be discussed later.

1.2 Basic 'Patch' Algorithm in 1-D

In the traditional approach outlined above, all pixels were used in an order-insensitive way. The contribution from each pixel in the sums can be added in any order without changing the vale of the sum. this means that the pixels could even be scrambled randomly as long as the mixture and database sample are scrambled identically, without changing the answer. To address this we have developed a new algorithm, described below

1.2.1 Minimization of Residuals for a Single Patch

The sum of the squared differences $\delta_L^2$ between pixels located in common patches in both the mixture and its constituents can be expressed as:

$$\delta_L^2 = \sum_{i \in L} \left( \frac{m_i - C_1 s_{i1} - C_2 s_{i2} - C_3 s_{i3} - \ldots - C_{N_s} s_{iN_s}}{\sigma_i} \right)^2, \quad (1.2.1\text{-}1)$$

or as $$\delta_L^2 = \left[ \sum_{i \in L} \left( \frac{m_i - C_1 s_{i1} - C_2 s_{i2} - C_3 s_{i3} - \ldots - C_{N_s} s_{iN_s}}{\sigma_i} \right) \right]^2. \quad (1.2.1\text{-}2)$$

To minimize $\delta_L^2$, differentiate with respect to each of the concentrations and get:

$$\frac{\partial}{\partial C_1} \delta_L^2 \rightarrow 0 \Rightarrow \quad (1.2.1\text{-}3)$$

$$\sum_{i \in L} \left[ 2 \left( \frac{m_i - C_1 s_{i1} - C_2 s_{i2} - C_3 s_{i3} - \ldots - C_{N_s} s_{iN_s}}{\sigma_i} \right) \left( \frac{-s_{i1}}{\sigma_i} \right) \right] = 0$$

$$\frac{\partial}{\partial C_2} \delta_L^2 \rightarrow 0 \Rightarrow \quad (1.2.1\text{-}4)$$

$$\sum_{i \in L} \left[ 2 \left( \frac{m_i - C_1 s_{i1} - C_2 s_{i2} - C_3 s_{i3} - \ldots - C_{N_s} s_{iN_s}}{\sigma_i} \right) \left( \frac{-s_{i2}}{\sigma_i} \right) \right] = 0$$

$$\frac{\partial}{\partial C_3} \delta_L^2 \rightarrow 0 \Rightarrow \quad (1.2.1\text{-}5)$$

$$\sum_{i \in L} \left[ 2 \left( \frac{m_i - C_1 s_{i1} - C_2 s_{i2} - C_3 s_{i3} - \ldots - C_{N_s} s_{iN_s}}{\sigma_i} \right) \left( \frac{-s_{i3}}{\sigma_i} \right) \right] = 0$$

$$\ldots \quad (1.2.1\text{-}6)$$

$$\frac{\partial}{\partial C_{N_3}} \delta_L^2 \rightarrow 0 \Rightarrow \quad (1.2.1\text{-}7)$$

$$\sum_{i \in L} \left[ 2 \left( \frac{m_i - C_1 s_{i1} - C_2 s_{i2} - C_3 s_{i3} - \ldots - C_{N_s} s_{iN_s}}{\sigma_i} \right) \left( \frac{-s_{iN_s}}{\sigma_i} \right) \right] = 0$$

Simplifying, and using the simpler notation $$\sum_{i \in L} m_i = \sum_L m \quad \text{and} \quad \sum_{i \in L} s_{i1} = \sum_L s_1$$

$$\sum_L \frac{m s_1}{\sigma^2} - C_1 \sum_L \frac{s_1 s_1}{\sigma^2} - C_2 \sum_L \frac{s_2 s_1}{\sigma^2} - \quad (1.2.1\text{-}8a)$$

$$C_3 \sum_L \frac{s_3 s_1}{\sigma^2} - \ldots C_{N_s} \sum_L \frac{s_{N_s} s_1}{\sigma^2} = 0$$

$$\sum_L \frac{m s_2}{\sigma^2} - C_1 \sum_L \frac{s_1 s_2}{\sigma^2} - C_2 \sum_L \frac{s_2 s_2}{\sigma^2} - \quad (1.2.1\text{-}8b)$$

$$C_3 \sum_L \frac{s_3 s_2}{\sigma^2} - \ldots C_{N_s} \sum_L \frac{s_{N_s} s_2}{\sigma^2} = 0$$

$$\sum_L \frac{m s_3}{\sigma^2} - C_1 \sum_L \frac{s_1 s_3}{\sigma^2} - C_2 \sum_L \frac{s_2 s_3}{\sigma^2} - \quad (1.2.1\text{-}8c)$$

$$C_3 \sum_L \frac{s_3 s_3}{\sigma^2} - \ldots C_{N_s} \sum_L \frac{s_{N_s} s_3}{\sigma^2} = 0$$

$$\ldots \quad (1.2.1\text{-}8d)$$

$$\sum_L \frac{m s_{N_s}}{\sigma^2} - C_1 \sum_L \frac{s_1 s_{N_s}}{\sigma^2} - C_2 \sum_L \frac{s_2 s_{N_s}}{\sigma^2} - \quad (1.2.1\text{-}8e)$$

$$C_3 \sum_L \frac{s_3 s_{N_s}}{\sigma^2} - \ldots C_{N_s} \sum_L \frac{s_{N_s} s_{N_s}}{\sigma^2} = 0$$

Rearranging, $$C_1 \sum_L \frac{s_1 s_1}{\sigma^2} + C_2 \sum_L \frac{s_1 s_2}{\sigma^2} + \quad (1.2.1\text{-}9a)$$

$$C_3 \sum_L \frac{s_1 s_3}{\sigma^2} + \ldots + C_{N_3} \sum_L \frac{s_1 s_{N_3}}{\sigma^2} = \sum_L \frac{m s_1}{\sigma^2}$$

$$C_1 \sum_L \frac{s_2 s_1}{\sigma^2} + C_2 \sum_L \frac{s_2 s_2}{\sigma^2} + \quad (1.2.1\text{-}9b)$$

$$C_3 \sum_L \frac{s_2 s_3}{\sigma^2} + \ldots + C_{N_3} \sum_L \frac{s_2 s_{N_3}}{\sigma^2} = \sum_L \frac{m s_2}{\sigma^2}$$

$$C_1 \sum_L \frac{s_3 s_1}{\sigma^2} + C_2 \sum_L \frac{s_3 s_2}{\sigma^2} + \quad (1.2.1\text{-}9c)$$

$$C_3 \sum_L \frac{s_3 s_3}{\sigma^2} + \ldots + C_{N_3} \sum_L \frac{s_3 s_{N_3}}{\sigma^2} = \sum_L \frac{m s_3}{\sigma^2}$$

$$\ldots \quad (1.2.1\text{-}9d)$$

$$C_1 \sum_L \frac{s_{N_3} s_1}{\sigma^2} + C_2 \sum_L \frac{s_{N_3} s_2}{\sigma^2} + \quad (1.2.1\text{-}9e)$$

$$C_3 \sum_L \frac{s_{N_3} s_3}{\sigma^2} + \ldots + C_{N_3} \sum_L \frac{s_{N_3} s_{N_3}}{\sigma^2} = \sum_L \frac{m s_{N_3}}{\sigma^2}$$

Which can be written as a matrix equation:

$$\begin{bmatrix} \sum_L \frac{s_1 s_1}{\sigma^2} & \sum_L \frac{s_1 s_2}{\sigma^2} & \sum_L \frac{s_1 s_3}{\sigma^2} & \cdots & \sum_L \frac{s_1 s_{N_3}}{\sigma^2} \\ \sum_L \frac{s_2 s_1}{\sigma^2} & \sum_L \frac{s_2 s_2}{\sigma^2} & \sum_L \frac{s_2 s_3}{\sigma^2} & \cdots & \sum_L \frac{s_2 s_{N_3}}{\sigma^2} \\ \sum_L \frac{s_3 s_1}{\sigma^2} & \sum_L \frac{s_3 s_2}{\sigma^2} & \sum_L \frac{s_3 s_3}{\sigma^2} & \cdots & \sum_L \frac{s_3 s_{N_3}}{\sigma^2} \\ \cdots & \cdots & \cdots & \cdots & \cdots \\ \sum_L \frac{s_{N_3} s_1}{\sigma^2} & \sum_L \frac{s_{N_3} s_2}{\sigma^2} & \sum_L \frac{s_{N_3} s_3}{\sigma^2} & \cdots & \sum_L \frac{s_{N_3} s_{N_3}}{\sigma^2} \end{bmatrix} \begin{bmatrix} C_1 \\ C_2 \\ C_3 \\ \ldots \\ C_{N_3} \end{bmatrix} = \begin{bmatrix} \sum_L \frac{m s_1}{\sigma^2} \\ \sum_L \frac{m s_2}{\sigma^2} \\ \sum_L \frac{m s_3}{\sigma^2} \\ \ldots \\ \sum_L \frac{m s_{N_3}}{\sigma^2} \end{bmatrix} \quad (1.2.1\text{-}10)$$

1.2.2 Multiple Patches in 1-D

Multiple patches are handled by stacking the equations for the patches on top of each other vertically: Simplifying, and using the simpler notation $$\sum_{i\in L} m = \sum_{L} m \text{ and } \sum_{i\in L} s_{il} = \sum_{L} s_l$$

In the previous section the minimization of $\delta_L^2$ for a single patch was demonstrated. In our case we our more interested in the general case of many patches. We want to minimize the sum of all $\delta_L^2$ as given by:

$$x^2 = \sum_{\forall L} \delta_L^2 = \sum_{\forall L} \sum_{i\in L} \left( \frac{m_i - C_1 s_{i1} - C_2 s_{i2} - C_3 s_{i3} - \ldots - C_{N_3} s_{iN_3}}{\sigma_i} \right) \quad (1.2.2\text{-}1)$$

$$\frac{\partial}{\partial C_1} x^2 \to 0 \Rightarrow \sum_{\forall L} \sum_{i\in L} \left[ 2\left( \frac{m_i - C_1 s_{i1} - C_2 s_{i2} - C_3 s_{i3} - \ldots - C_{N_3} s_{iN_3}}{\sigma_i} \right)\left(\frac{-s_{i1}}{\sigma_i}\right) \right] = 0 \quad (1.2.2\text{-}2a)$$

$$\frac{\partial}{\partial C_2} x^2 \to 0 \Rightarrow \sum_{\forall L} \sum_{i\in L} \left[ 2\left( \frac{m_i - C_1 s_{i1} - C_2 s_{i2} - C_3 s_{i3} - \ldots - C_{N_3} s_{iN_3}}{\sigma_i} \right)\left(\frac{-s_{i2}}{\sigma_i}\right) \right] = 0 \quad (1.2.2\text{-}2b)$$

$$\frac{\partial}{\partial C_3} x^2 \to 0 \Rightarrow \sum_{\forall L} \sum_{i\in L} \left[ 2\left( \frac{m_i - C_1 s_{i1} - C_2 s_{i2} - C_3 s_{i3} - \ldots - C_{N_3} s_{iN_3}}{\sigma_i} \right)\left(\frac{-s_{i3}}{\sigma_i}\right) \right] = 0 \quad (1.2.2\text{-}2c)$$

$$\ldots \quad (1.2.2\text{-}2d)$$

$$\frac{\partial}{\partial C_{N_3}} x^2 \to 0 \Rightarrow \sum_{\forall L} \sum_{i\in L} \left[ 2\left( \frac{m_i - C_1 s_{i1} - C_2 s_{i2} - C_3 s_{i3} - \ldots - C_{N_3} s_{iN_3}}{\sigma_i} \right)\left(\frac{-s_{iN_3}}{\sigma_i}\right) \right] = 0 \quad (1.2.2\text{-}2e)$$

$$\begin{bmatrix} \sum_{\forall L}\sum_L \frac{s_1 s_1}{\sigma^2} & \sum_{\forall L}\sum_L \frac{s_1 s_2}{\sigma^2} & \sum_{\forall L}\sum_L \frac{s_1 s_3}{\sigma^2} & \cdots & \sum_{\forall L}\sum_L \frac{s_1 s_{N_3}}{\sigma^2} \\ \sum_{\forall L}\sum_L \frac{s_2 s_1}{\sigma^2} & \sum_{\forall L}\sum_L \frac{s_2 s_2}{\sigma^2} & \sum_{\forall L}\sum_L \frac{s_2 s_3}{\sigma^2} & \cdots & \sum_{\forall L}\sum_L \frac{s_2 s_{N_3}}{\sigma^2} \\ \sum_{\forall L}\sum_L \frac{s_3 s_1}{\sigma^2} & \sum_{\forall L}\sum_L \frac{s_3 s_2}{\sigma^2} & \sum_{\forall L}\sum_L \frac{s_3 s_3}{\sigma^2} & \cdots & \sum_{\forall L}\sum_L \frac{s_3 s_{N_3}}{\sigma^2} \\ \cdots & \cdots & \cdots & \cdots & \cdots \\ \sum_{\forall L}\sum_L \frac{s_{N_3} s_1}{\sigma^2} & \sum_{\forall L}\sum_L \frac{s_{N_3} s_2}{\sigma^2} & \sum_{\forall L}\sum_L \frac{s_{N_3} s_3}{\sigma^2} & \cdots & \sum_{\forall L}\sum_L \frac{s_{N_3} s_{N_3}}{\sigma^2} \end{bmatrix} \begin{bmatrix} C_1 \\ C_2 \\ C_3 \\ \cdots \\ C_{N_3} \end{bmatrix} = \begin{bmatrix} \sum_{\forall L}\sum_L \frac{m s_1}{\sigma^2} \\ \sum_{\forall L}\sum_L \frac{m s_2}{\sigma^2} \\ \sum_{\forall L}\sum_L \frac{m s_3}{\sigma^2} \\ \cdots \\ \sum_{\forall L}\sum_L \frac{m s_{N_3}}{\sigma^2} \end{bmatrix} \quad (1.2.2\text{-}3)$$

Notice there is no requirement for patches to be sized similarly or located in any special place. The sums are for all elements in a patch, which can be any size or shape.

$$\begin{bmatrix} \sum_{L_1} \frac{s_1 s_1}{\sigma^2} & \sum_{L_1} \frac{s_2 s_1}{\sigma^2} & \sum_{L_1} \frac{s_3 s_1}{\sigma^2} & \cdots & \sum_{L_1} \frac{s_{N_3} s_1}{\sigma^2} \\ \sum_{L_1} \frac{s_1 s_2}{\sigma^2} & \sum_{L_1} \frac{s_2 s_2}{\sigma^2} & \sum_{L_1} \frac{s_3 s_2}{\sigma^2} & \cdots & \sum_{L_1} \frac{s_{N_3} s_2}{\sigma^2} \\ \sum_{L_1} \frac{s_1 s_3}{\sigma^2} & \sum_{L_1} \frac{s_2 s_1}{\sigma^2} & \sum_{L_1} \frac{s_2 s_3}{\sigma^2} & \cdots & \sum_{L_1} \frac{s_{N_3} s_3}{\sigma^2} \\ \cdots & \cdots & \cdots & \cdots & \cdots \\ \sum_{L_1} \frac{s_1 s_{N_5}}{\sigma^2} & \sum_{L_1} \frac{s_2 s_{N_3}}{\sigma^2} & \sum_{L_1} \frac{s_2 s_{N_3}}{\sigma^2} & \cdots & \sum_{L_1} \frac{s_{N_3} s_{N_3}}{\sigma^2} \\ \sum_{L_2} \frac{s_1 s_1}{\sigma^2} & \sum_{L_2} \frac{s_2 s_1}{\sigma^2} & \sum_{L_2} \frac{s_3 s_1}{\sigma^2} & \cdots & \sum_{L_2} \frac{s_{N_3} s_1}{\sigma^2} \\ \sum_{L_2} \frac{s_1 s_2}{\sigma^2} & \sum_{L_2} \frac{s_2 s_2}{\sigma^2} & \sum_{L_2} \frac{s_3 s_2}{\sigma^2} & \cdots & \sum_{L_{2_1}} \frac{s_{N_3} s_2}{\sigma^2} \end{bmatrix} \begin{bmatrix} \sum_{L_1} \frac{m s_1}{\sigma^2} \\ \sum_{L_1} \frac{m s_2}{\sigma^2} \\ \sum_{L_1} \frac{m s_3}{\sigma^2} \\ \cdots \\ \sum_{L_1} \frac{m s_{N_3}}{\sigma^2} \\ \sum_{L_2} \frac{m s_1}{\sigma^2} \\ \sum_{L_2} \frac{m s_2}{\sigma^2} \end{bmatrix} \quad (1.2\text{-}3)$$

-continued $$\begin{bmatrix} \sum_{L_2} \frac{s_1 s_3}{\sigma^2} & \sum_{L_2} \frac{s_2 s_3}{\sigma^2} & \sum_{L_2} \frac{s_3 s_3}{\sigma^2} & \cdots & \sum_{L_2} \frac{s_{N_3} s_3}{\sigma^2} \\ \cdots & \cdots & \cdots & \cdots & \cdots \\ \sum_{L_2} \frac{s_1 s_{N_3}}{\sigma^2} & \sum_{L_2} \frac{s_2 s_{N_3}}{\sigma^2} & \sum_{L_2} \frac{s_3 s_{N_3}}{\sigma^2} & \cdots & \sum_{L_2} \frac{s_{N_3} s_{N_3}}{\sigma^2} \\ \sum_{L_3} \frac{s_1 s_1}{\sigma^2} & \sum_{L_3} \frac{s_2 s_1}{\sigma^2} & \sum_{L_3} \frac{s_3 s_1}{\sigma^2} & \cdots & \sum_{L_3} \frac{s_{N_3} s_1}{\sigma^2} \\ \sum_{L_3} \frac{s_1 s_2}{\sigma^2} & \sum_{L_3} \frac{s_2}{\sigma^2} s_2 & \sum_{L_3} \frac{s_3 s_2}{\sigma^2} & \cdots & \sum_{L_3} \frac{s_{N_3} s_2}{\sigma^2} \\ \sum_{L_3} \frac{s_1 s_3}{\sigma^2} & \sum_{L_3} \frac{s_2 s_3}{\sigma^2} & \sum_{L_3} \frac{s_3 s_3}{\sigma^2} & \cdots & \sum_{L_3} \frac{s_{N_3} s_3}{\sigma^2} \\ \cdots & \cdots & \cdots & \cdots & \cdots \\ \sum_{L_3} \frac{s_1 s_{N_3}}{\sigma^2} & \sum_{L_3} \frac{s_2 s_{N_3}}{\sigma^2} & \sum_{L_3} \frac{s_3 s_{N_3}}{\sigma^2} & \cdots & \sum_{L_3} \frac{s_{N_3} s_{N_3}}{\sigma^2} \\ \sum_{L_N} \frac{s_1 s_1}{\sigma^2} & \sum_{L_N} \frac{s_2 s_1}{\sigma^2} & \sum_{L_N} \frac{s_3 s_1}{\sigma^2} & \cdots & \sum_{L_N} \frac{s_{N_3} s_1}{\sigma^2} \\ \sum_{L_N} \frac{s_1 s_2}{\sigma^2} & \sum_{L_N} \frac{s_2 s_2}{\sigma^2} & \sum_{L_N} \frac{s_3 s_2}{\sigma^2} & \cdots & \sum_{L_N} \frac{s_{N_3} s_2}{\sigma^2} \\ \sum_{L_N} \frac{s_1 s_3}{\sigma^2} & \sum_{L_N} \frac{s_2 s_3}{\sigma^2} & \sum_{L_N} \frac{s_3 s_3}{\sigma^2} & \cdots & \sum_{L_N} \frac{s_{N_3} s_3}{\sigma^2} \\ \cdots & \cdots & \cdots & \cdots & \cdots \\ \sum_{L_N} \frac{s_1 s_{N_3}}{\sigma^2} & \sum_{L_N} \frac{s_2 s_{N_3}}{\sigma^2} & \sum_{L_N} \frac{s_3 s_{N_3}}{\sigma^2} & \cdots & \sum_{L_N} \frac{s_{N_3} s_{N_3}}{\sigma^2} \end{bmatrix} \begin{bmatrix} C_1 \\ C_2 \\ C_3 \\ \cdots \\ C_{N_3} \end{bmatrix} = \begin{bmatrix} \sum_{L_2} \frac{m s_3}{\sigma^2} \\ \cdots \\ \sum_{L_2} \frac{m s_{N_3}}{\sigma^2} \\ \sum_{L_3} \frac{m s_1}{\sigma^2} \\ \sum_{L_3} \frac{m s_2}{\sigma^2} \\ \sum_{L_3} \frac{m s_3}{\sigma^2} \\ \cdots \\ \sum_{L_3} \frac{m s_{N_3}}{\sigma^2} \\ \sum_{L_N} \frac{m s_1}{\sigma^2} \\ \sum_{L_N} \frac{m s_2}{\sigma^2} \\ \sum_{L_N} \frac{m s_3}{\sigma^2} \\ \cdots \\ \sum_{L_N} \frac{m s_{N_3}}{\sigma^2} \end{bmatrix}$$

1.3 Basic 'Patch' Algorithm in 2-D

In this section the mathematics for a 2-D image-recognition algorithm is described. The problem to be solved is: given a 2-D 'unknown', what are the concentrations of it's 2-D constituents? The unknown mixture is assumed to be in the form a 2-D array and is assumed to be made up of a linear superposition of many 2-D elemental constituent images. Such 2-D arrays can be from any source, from a set of pixels describing objects in a picture, to the application of primarily interested: 2-D multispectral UV LISAR images. In the LIDAR application multispectral 2-D images of the UV florescence of many chemicals are measured and stored individually in a database. When the algorithm is given an unknown, it estimates the concentrations of the constituents in the database which are present in the unknown.

The arrays need not be square, but for simplicity we assume the image is rectangular. Even though this requirement is not really necessary, it is expedient to limit 2-D images to be rectangular when using some computer languages such as FORTRAN. The unknown mixture will be denoted by [M] with dimensions m×n:

$$[M] = \begin{bmatrix} m_{11} & m_{12} & m_{13} & \cdots & m_{1n} \\ m_{21} & m_{22} & m_{23} & \cdots & m_{2n} \\ m_{31} & m_{32} & m_{33} & \cdots & m_{3n} \\ \cdots & \cdots & \cdots & \cdots & \cdots \\ m_{m1} & m_{m2} & m_{m3} & \cdots & m_{mn} \end{bmatrix}. \quad (1.3\text{-}1)$$

Subscripts are used to designate array elements. It is convenient to think of each $m_{ij}$ as an intensity at pixel location (ij).

Now suppose the mixture [M] is made up of the linear superposition of $N_s$ constituents. [M] may also contain constituents not in the data base, plus some uncertainty or noise. Each constituent, or sample $[S_l]$, (where $1 \leq N_s$) is also a 2-D m×n array. Superscripts are used to identify different samples, $$[S_l] = \begin{bmatrix} s_{11l} & s_{12l} & s_{13l} & \cdots & s_{1nl} \\ s_{21l} & s_{22l} & s_{23l} & \cdots & s_{2nl} \\ s_{31l} & s_{32l} & s_{33l} & \cdots & s_{3nl} \\ \cdots & \cdots & \cdots & \cdots & \cdots \\ s_{m1l} & s_{m2l} & s_{m3l} & \cdots & s_{mnl} \end{bmatrix}. \quad (1.3\text{-}2)$$

Since [M] is assumed to be made up of a linear combinations of the samples, [M] can be written as:

$$[M] = C_1[S_1] + C_2[S_2] + C_3[S_3] + \ldots + C_{N_s}[S_{N_s}] + \text{noise}. \quad (1.3\text{-}3)$$

The problem is to estimate the concentrations $C_l$, $k=1, N_s$ $$\begin{bmatrix} m_{11} & m_{12} & m_{13} & \cdots & m_{1n} \\ m_{21} & m_{22} & m_{23} & \cdots & m_{2n} \\ m_{31} & m_{32} & m_{33} & \cdots & m_{3n} \\ \cdots & \cdots & \cdots & \cdots & \cdots \\ m_{m1} & m_{m2} & m_{m3} & \cdots & m_{mn} \end{bmatrix} = C^1 \begin{bmatrix} s_{111} & s_{121} & s_{131} & \cdots & s_{1n1} \\ s_{211} & s_{221} & s_{231} & \cdots & s_{2n1} \\ s_{311} & s_{321} & s_{331} & \cdots & s_{3n1} \\ \cdots & \cdots & \cdots & \cdots & \cdots \\ s_{m11} & s_{m21} & s_{m31} & \cdots & s_{mn1} \end{bmatrix} +$$

$$C^2 \begin{bmatrix} s_{112} & s_{122} & s_{132} & \cdots & s_{1n2} \\ s_{212} & s_{222} & s_{232} & \cdots & s_{2n2} \\ s_{312} & s_{322} & s_{332} & \cdots & s_{3n2} \\ \cdots & \cdots & \cdots & \cdots & \cdots \\ s_{m12} & s_{m22} & s_{m32} & \cdots & s_{mn2} \end{bmatrix} + \ldots + \text{noise}$$

One method to solve this problem is to minimize the sum of the squared differences between pixels in the unknown and a hypothetical set of sample concentrations. This least-square method is usually well determined and straight forward but does not take advantage of the 2-D feature of the problem. In a pixel-by-pixel minimization, ordering is not important and information can be under utilized. The pixel-by-pixel minimization is a special case of the patch algorithm described next. To take advantage of the 2-D nature of the problem it is possible to minimize the squared error between a group of near-neighbor pixels in both the unknown mixture and its hypothetical constituent makeup. A set of near-neighbor pixels in a group is defined here to be a 'patch' of the array. Different patching strategies are possible, as illustrated in FIG. 5.

Bad data can be ignored while emphasizing regions of strong pixel-to-pixel correlation.

1.3.1 Minimization of Residuals for a Single Patch

The sum of the squared differences $\delta_P^2$ between pixels located in common patches in both the mixture and its constituents can be expressed as:

$$\delta_P^2 = \sum_{(i,j) \in P} \left( \frac{m_{ij} - C_1 s_{ij1} - C_2 s_{ij2} - C_3 s_{ij3} - \ldots - C_{N_3} s_{ijN_3}}{\sigma_i} \right)^2, \quad (1.3.1\text{-}1)$$

or as $$\delta_P^2 = \left[ \sum_{i,j \in P} \left( \frac{m_{ij} - C_1 s_{ij1} - C_2 s_{ij2} - C_3 s_{ij3} - \ldots - C_{N_3} s_{ijN_3}}{\sigma_i} \right) \right]^2. \quad (1.3.1\text{-}2)$$

To minimize $\delta_P^2$, differentiate with respect to each of the concentrations and get:

$$\frac{\partial}{\partial C_1} \delta_P^2 \to 0 \Rightarrow \quad (1.3.1\text{-}3a)$$

$$\sum_{i,j \in P} \left[ 2 \left( \frac{m_{ij} - C_1 s_{ij1} - C_2 s_{ij2} - C_3 s_{ij3} - \ldots - C_{N_3} s_{ijN_3}}{\sigma_i} \right) \left( \frac{-s_{ij1}}{\sigma_i} \right) \right] = 0$$

$$\frac{\partial}{\partial C_2} \delta_P^2 \to 0 \Rightarrow \quad (1.3.1\text{-}3b)$$

$$\sum_{i,j \in P} \left[ 2 \left( \frac{m_{ij} - C_1 s_{ij1} - C_2 s_{ij2} - C_3 s_{ij3} - \ldots - C_{N_3} s_{ijN_3}}{\sigma_i} \right) \left( \frac{-s_{ij2}}{\sigma_i} \right) \right] = 0$$

$$\frac{\partial}{\partial C_3} \delta_P^2 \to 0 \Rightarrow \quad (1.3.1\text{-}3c)$$

$$\sum_{i,j \in P} \left[ 2 \left( \frac{m_{ij} - C_1 s_{ij1} - C_2 s_{ij2} - C_3 s_{ij3} - \ldots - C_{N_3} s_{ijN_3}}{\sigma_i} \right) \left( \frac{-s_{ij3}}{\sigma_i} \right) \right] = 0$$

$$\ldots \quad (1.3.1\text{-}3d)$$

$$\frac{\partial}{\partial C_{N_3}} \delta_P^2 \to 0 \Rightarrow \quad (1.3.1\text{-}3e)$$

$$\sum_{i,j \in P} \left[ 2 \left( \frac{m_{ij} - C_1 s_{ij1} - C_2 s_{ij2} - C_3 s_{ij3} - \ldots - C_{N_3} s_{ijN_3}}{\sigma_i} \right) \left( \frac{-s_{ijN_3}}{\sigma_i} \right) \right] = 0$$

Simplifying, and using the simpler notation $$\sum_{(i,j) \in P} m_{ij} = \sum_P m \quad \text{and} \quad \sum_{(i,j) \in P} s_{ijl} = \sum_P s_l$$

$$\sum_P \frac{m s_1}{\sigma^2} - C_1 \sum_P \frac{s_1 s_1}{\sigma^2} - C_2 \sum_P \frac{s_2 s_1}{\sigma^2} - \quad (1.3.1\text{-}4a)$$
$$C_3 \sum_P \frac{s_3 s_1}{\sigma^2} - \ldots C_{N_3} \sum_P \frac{s_{N_3} s_1}{\sigma^2} = 0$$

$$\sum_P \frac{m s_2}{\sigma^2} - C_1 \sum_P \frac{s_1 s_2}{\sigma^2} - C_2 \sum_P \frac{s_2 s_2}{\sigma^2} - \quad (1.3.1\text{-}4b)$$
$$C_3 \sum_P \frac{s_3 s_2}{\sigma^2} - \ldots C_{N_3} \sum_P \frac{s_{N_3} s_2}{\sigma^2} = 0$$

$$\sum_P \frac{m s_3}{\sigma^2} - C_1 \sum_P \frac{s_1 s_3}{\sigma^2} - C_2 \sum_P \frac{s_2 s_3}{\sigma^2} - \quad (1.3.1\text{-}4c)$$
$$C_3 \sum_P \frac{s_3 s_3}{\sigma^2} - \ldots C_{N_3} \sum_P \frac{s_{N_3} s_3}{\sigma^2} = 0$$

$$\ldots \quad (1.3.1\text{-}4d)$$

$$\sum_P \frac{m s_{N_3}}{\sigma^2} - C_1 \sum_P \frac{s_1 s_{N_3}}{\sigma^2} - C_2 \sum_P \frac{s_2 s_{N_3}}{\sigma^2} - \quad (1.3.1\text{-}4e)$$
$$C_3 \sum_P \frac{s_3 s_{N_3}}{\sigma^2} - \ldots C_{N_3} \sum_P \frac{s_{N_3} s_{N_3}}{\sigma^2} = 0$$

Rearranging, $$C_1 \sum_P \frac{s_1 s_1}{\sigma^2} + C_2 \sum_P \frac{s_2 s_1}{\sigma^2} + \quad (1.3.1\text{-}5a)$$
$$C_3 \sum_P \frac{s_3 s_1}{\sigma^2} + \ldots + C_{N_3} \sum_P \frac{s_{N_3} s_1}{\sigma^2} = \sum_P \frac{m s_1}{\sigma^2}$$

$$C_1 \sum_P \frac{s_1 s_2}{\sigma^2} + C_2 \sum_P \frac{s_2 s_2}{\sigma^2} + \quad (1.3.1\text{-}5b)$$
$$C_3 \sum_P \frac{s_3 s_2}{\sigma^2} + \ldots + C_{N_3} \sum_P \frac{s_{N_3} s_2}{\sigma^2} = \sum_P \frac{m s_2}{\sigma^2}$$

$$C_1 \sum_P \frac{s_1 s_3}{\sigma^2} + C_2 \sum_P \frac{s_2 s_3}{\sigma^2} + \quad (1.3.1\text{-}5c)$$
$$C_3 \sum_P \frac{s_3 s_3}{\sigma^2} + \ldots + C_{N_3} \sum_P \frac{s_{N_3} s_3}{\sigma^2} = \sum_P \frac{m s_3}{\sigma^2}$$

$$\ldots \quad (1.3.1\text{-}5d)$$

$$C_1 \sum_P \frac{s_1 s_{N_3}}{\sigma^2} + C_2 \sum_P \frac{s_2 s_{N_3}}{\sigma^2} + \quad (1.3.1\text{-}5e)$$
$$C_3 \sum_P \frac{s_3 s_{N_3}}{\sigma^2} + \ldots + C_{N_3} \sum_P \frac{s_{N_3} s_{N_3}}{\sigma^2} = \sum_P \frac{m s_{N_3}}{\sigma^2}$$

Which can be written as a matrix equation:

$$\begin{bmatrix} \sum_P \frac{s_1 s_1}{\sigma^2} & \sum_P \frac{s_2 s_1}{\sigma^2} & \sum_P \frac{s_3 s_1}{\sigma^2} & \cdots & \sum_P \frac{s_{N_3} s_1}{\sigma^2} \\ \sum_P \frac{s_1 s_2}{\sigma^2} & \sum_P \frac{s_2 s_2}{\sigma^2} & \sum_P \frac{s_3 s_2}{\sigma^2} & \cdots & \sum_P \frac{s_{N_3} s_2}{\sigma^2} \\ \sum_P \frac{s_1 s_3}{\sigma^2} & \sum_P \frac{s_2 s_3}{\sigma^2} & \sum_P \frac{s_3 s_3}{\sigma^2} & \cdots & \sum_P \frac{s_{N_3} s_3}{\sigma^2} \\ \cdots & \cdots & \cdots & \cdots & \cdots \\ \sum_P \frac{s_1 s_{N_3}}{\sigma^2} & \sum_P \frac{s_2 s_{N_3}}{\sigma^2} & \sum_P \frac{s_3 s_{N_3}}{\sigma^2} & \cdots & \sum_P \frac{s_{N_3} s_{N_3}}{\sigma^2} \end{bmatrix} \begin{bmatrix} C_1 \\ C_2 \\ C_3 \\ \cdots \\ C_{N_3} \end{bmatrix} = \begin{bmatrix} \sum_P \frac{m s_1}{\sigma^2} \\ \sum_P \frac{m s_2}{\sigma^2} \\ \sum_P \frac{m s_3}{\sigma^2} \\ \cdots \\ \sum_P \frac{m s_{N_3}}{\sigma^2} \end{bmatrix} \quad (1.3.1\text{-}6)$$

1.3.2 Multiple Patches in 2-D

Multiple patches are handled by stacking the equations for the patch on top of each other vertically: Simplifying, and using the simpler notations $$\sum_{(i,j) \in P} m = \sum_P m$$

In the previous section the minimization of $\delta_P^2$ for a single patch was demonstrated. In our case we our more interested in the general case of many patches. We want to minimize the sum of all $\delta_P^2$ as given by:

$$\chi^2 = \sum_{\forall P} \delta_P^2 = \sum_{\forall P} \sum_{(i,j) \in P} \left( \frac{m_{ij} - C_1 s_{ij1} - C_2 s_{ij2} - C_3 s_{ij3} - \ldots - C_{N_s} s_{ij N_s}}{\sigma_i} \right) \quad (1.3.2\text{-}1)$$

$$\frac{\partial}{\partial C_1} \chi^2 \to 0 \Rightarrow \sum_{\forall P} \sum_{i,j \in P} \left[ 2 \left( \frac{m_{ij} - C_1 s_{ij1} - C_2 s_{ij2} - C_3 s_{ij3} - \ldots - C_{N_s} s_{ij N_s}}{\sigma_i} \right) \left( \frac{-s_{ij1}}{\sigma_i} \right) \right] = 0 \quad (1.3.2\text{-}2a)$$

$$\frac{\partial}{\partial C_2} \chi^2 \to 0 \Rightarrow \sum_{\forall P} \sum_{i,j \in P} \left[ 2 \left( \frac{m_{ij} - C_1 s_{ij1} - C_2 s_{ij2} - C_3 s_{ij3} - \ldots - C_{N_s} s_{ij N_s}}{\sigma_i} \right) \left( \frac{-s_{ij2}}{\sigma_i} \right) \right] = 0 \quad (1.3.2\text{-}2b)$$

$$\frac{\partial}{\partial C_3} \chi^2 \to 0 \Rightarrow \sum_{\forall P} \sum_{i,j \in P} \left[ 2 \left( \frac{m_{ij} - C_1 s_{ij1} - C_2 s_{ij2} - C_3 s_{ij3} - \ldots - C_{N_s} s_{ij N_s}}{\sigma_i} \right) \left( \frac{-s_{ij3}}{\sigma_i} \right) \right] = 0 \quad (1.3.2\text{-}2c)$$

$$\ldots \quad (1.3.2\text{-}2d)$$

$$\frac{\partial}{\partial C_{N_s}} \chi^2 \to 0 \Rightarrow \sum_{\forall P} \sum_{i,j \in P} \left[ 2 \left( \frac{m_{ij} - C_1 s_{ij1} - C_2 s_{ij2} - C_3 s_{ij3} - \ldots - C_{N_s} s_{ij N_s}}{\sigma_i} \right) \left( \frac{-s_{ij N_s}}{\sigma_i} \right) \right] = 0 \quad (1.3.2\text{-}2e)$$

$$\begin{bmatrix} \sum_{\forall P} \sum_P \frac{s_1 s_1}{\sigma^2} & \sum_{\forall P} \sum_P \frac{s_1 s_2}{\sigma^2} & \sum_{\forall P} \sum_P \frac{s_1 s_3}{\sigma^2} & \cdots & \sum_{\forall P} \sum_P \frac{s_1 s_{N_s}}{\sigma^2} \\ \sum_{\forall P} \sum_P \frac{s_2 s_1}{\sigma^2} & \sum_{\forall P} \sum_P \frac{s_2 s_2}{\sigma^2} & \sum_{\forall P} \sum_P \frac{s_2 s_3}{\sigma^2} & \cdots & \sum_{\forall P} \sum_P \frac{s_2 s_{N_s}}{\sigma^2} \\ \sum_{\forall P} \sum_P \frac{s_3 s_1}{\sigma^2} & \sum_{\forall P} \sum_P \frac{s_3 s_2}{\sigma^2} & \sum_{\forall P} \sum_P \frac{s_3 s_3}{\sigma^2} & \cdots & \sum_{\forall P} \sum_P \frac{s_3 s_{N_s}}{\sigma^2} \\ \cdots & \cdots & \cdots & \cdots & \cdots \\ \sum_{\forall P} \sum_P \frac{s_{N_s} s_1}{\sigma^2} & \sum_{\forall P} \sum_P \frac{s_{N_s} s_2}{\sigma^2} & \sum_{\forall P} \sum_P \frac{s_{N_s} s_3}{\sigma^2} & \cdots & \sum_{\forall P} \sum_P \frac{s_{N_s} s_{N_s}}{\sigma^2} \end{bmatrix} \begin{bmatrix} C_1 \\ C_2 \\ C_3 \\ \cdots \\ C_{N_s} \end{bmatrix} = \begin{bmatrix} \sum_{\forall P} \sum_P \frac{m s_1}{\sigma^2} \\ \sum_{\forall P} \sum_P \frac{m s_2}{\sigma^2} \\ \sum_{\forall P} \sum_P \frac{m s_3}{\sigma^2} \\ \cdots \\ \sum_{\forall P} \sum_P \frac{m s_{N_s}}{\sigma^2} \end{bmatrix} \quad (1.3.2\text{-}3)$$

Notice there is no requirement for patches to be sized similarly to located in any special place. The sums are for all elements in a patch, which can be any size or shape.

$$\begin{bmatrix} \sum_{P_1} \frac{s_1 s_1}{\sigma^2} & \sum_{P_1} \frac{s_2 s_1}{\sigma^2} & \sum_{P_1} \frac{s_3 s_1}{\sigma^2} & \cdots & \sum_{P_1} \frac{s_{N_s} s_1}{\sigma^2} \\ \sum_{P_1} \frac{s_1 s_2}{\sigma^2} & \sum_{P_1} \frac{s_2 s_2}{\sigma^2} & \sum_{P_1} \frac{s_3 s_2}{\sigma^2} & \cdots & \sum_{P_1} \frac{s_{N_s} s_2}{\sigma^2} \\ \sum_{P_1} \frac{s_1 s_3}{\sigma^2} & \sum_{P_1} \frac{s_2 s_3}{\sigma^2} & \sum_{P_1} \frac{s_2 s_3}{\sigma^2} & \cdots & \sum_{P_1} \frac{s_{N_s} s_3}{\sigma^2} \\ \cdots & \cdots & \cdots & \cdots & \cdots \\ \sum_{P_1} \frac{s_1 s_{N_s}}{\sigma^2} & \sum_{P_1} \frac{s_2 s_{N_s}}{\sigma^2} & \sum_{P_1} \frac{s_2 s_{N_s}}{\sigma^2} & \cdots & \sum_{P_1} \frac{s_{N_s} s_{N_s}}{\sigma^2} \\ \sum_{P_2} \frac{s_1 s_1}{\sigma^2} & \sum_{P_2} \frac{s_2 s_1}{\sigma^2} & \sum_{P_2} \frac{s_3 s_1}{\sigma^2} & \cdots & \sum_{P_2} \frac{s_{N_s} s_1}{\sigma^2} \\ \sum_{P_2} \frac{s_1 s_2}{\sigma^2} & \sum_{P_2} \frac{s_2 s_2}{\sigma^2} & \sum_{P_2} \frac{s_3 s_2}{\sigma^2} & \cdots & \sum_{P_2} \frac{s_{N_s} s_2}{\sigma^2} \\ \sum_{P_2} \frac{s_1 s_3}{\sigma^2} & \sum_{P_2} \frac{s_2 s_3}{\sigma^2} & \sum_{P_2} \frac{s_3 s_3}{\sigma^2} & \cdots & \sum_{P_2} \frac{s_{N_s} s_3}{\sigma^2} \\ \cdots & \cdots & \cdots & \cdots & \cdots \\ \sum_{P_2} \frac{s_1 s_{N_s}}{\sigma^2} & \sum_{P_2} \frac{s_2 s_{N_s}}{\sigma^2} & \sum_{P_2} \frac{s_3 s_{N_s}}{\sigma^2} & \cdots & \sum_{P_2} \frac{s_{N_s} s_{N_s}}{\sigma^2} \\ \sum_{P_3} \frac{s_1 s_1}{\sigma^2} & \sum_{P_3} \frac{s_2 s_1}{\sigma^2} & \sum_{P_3} \frac{s_3 s_1}{\sigma^2} & \cdots & \sum_{P_3} \frac{s_{N_s} s_1}{\sigma^2} \\ \sum_{P_3} \frac{s_1 s_2}{\sigma^2} & \sum_{P_3} \frac{s_2}{\sigma^2} s_2 & \sum_{P_3} \frac{s_3 s_2}{\sigma^2} & \cdots & \sum_{P_3} \frac{s_{N_s} s_2}{\sigma^2} \\ \sum_{P_3} \frac{s_1 s_3}{\sigma^2} & \sum_{P_3} \frac{s_2 s_3}{\sigma^2} & \sum_{P_3} \frac{s_3 s_3}{\sigma^2} & \cdots & \sum_{P_3} \frac{s_{N_s} s_3}{\sigma^2} \\ \cdots & \cdots & \cdots & \cdots & \cdots \\ \sum_{P_3} \frac{s_1 s_{N_s}}{\sigma^2} & \sum_{P_3} \frac{s_2 s_{N_s}}{\sigma^2} & \sum_{P_3} \frac{s_3 s_{N_s}}{\sigma^2} & \cdots & \sum_{P_3} \frac{s_{N_s} s_{N_s}}{\sigma^2} \\ \cdots & \cdots & \cdots & \cdots & \cdots \\ \sum_{P_N} \frac{s_1 s_1}{\sigma^2} & \sum_{P_N} \frac{s_2 s_1}{\sigma^2} & \sum_{P_N} \frac{s_3 s_1}{\sigma^2} & \cdots & \sum_{P_N} \frac{s_{N_s} s_1}{\sigma^2} \\ \sum_{P_N} \frac{s_1 s_2}{\sigma^2} & \sum_{P_N} \frac{s_2 s_2}{\sigma^2} & \sum_{P_N} \frac{s_3 s_2}{\sigma^2} & \cdots & \sum_{P_N} \frac{s_{N_s} s_2}{\sigma^2} \\ \sum_{P_N} \frac{s_1 s_3}{\sigma^2} & \sum_{P_N} \frac{s_2 s_3}{\sigma^2} & \sum_{P_N} \frac{s_3 s_3}{\sigma^2} & \cdots & \sum_{P_N} \frac{s_{N_s} s_3}{\sigma^2} \\ \cdots & \cdots & \cdots & \cdots & \cdots \\ \sum_{P_N} \frac{s_1 s_{N_s}}{\sigma^2} & \sum_{P_N} \frac{s_2 s_{N_s}}{\sigma^2} & \sum_{P_N} \frac{s_3 s_{N_s}}{\sigma^2} & \cdots & \sum_{P_N} \frac{s_{N_s} s_{N_s}}{\sigma^2} \end{bmatrix} \begin{bmatrix} C_1 \\ C_2 \\ C_3 \\ \cdots \\ C_{N_s} \end{bmatrix} = \begin{bmatrix} \sum_{P_1} \frac{m s_1}{\sigma^2} \\ \sum_{P_1} \frac{m s_2}{\sigma^2} \\ \sum_{P_1} \frac{m s_3}{\sigma^2} \\ \cdots \\ \sum_{P_1} \frac{m s_{N_s}}{\sigma^2} \\ \sum_{P_2} \frac{m s_1}{\sigma^2} \\ \sum_{P_2} \frac{m s_2}{\sigma^2} \\ \sum_{P_2} \frac{m s_3}{\sigma^2} \\ \cdots \\ \sum_{P_2} \frac{m s_{N_s}}{\sigma^2} \\ \sum_{P_3} \frac{m s_1}{\sigma^2} \\ \sum_{P_3} \frac{m s_2}{\sigma^2} \\ \sum_{P_3} \frac{m s_3}{\sigma^2} \\ \cdots \\ \sum_{P_3} \frac{m s_{N_s}}{\sigma^2} \\ \cdots \\ \sum_{P_N} \frac{m s_1}{\sigma^2} \\ \sum_{P_N} \frac{m s_2}{\sigma^2} \\ \sum_{P_N} \frac{m s_3}{\sigma^2} \\ \cdots \\ \sum_{P_N} \frac{m s_{N_s}}{\sigma^2} \end{bmatrix} \quad (1.3\text{-}3)$$

1.4 Basic 'Patch' Algorithm in 3-D

1.4.1 Minimization of Residuals for a Single Patch

The sum of the squared differences $\delta_P^2$ between pixels located in common patches in both the mixture and its constituents can be expressed as:

$$\delta_v^2 = \sum_{(i,j,k) \in V} \left( \frac{m_{ijk} - C_1 s_{ijk1} - C_2 s_{ijk2} - C_3 s_{ijk3} - \ldots - C_{N_s} s_{ijkN_s}}{\sigma_i} \right)^2, \quad (1.4.1\text{-}1)$$

or as $$\delta_v^2 = \left[ \sum_{i,j,k \in V} \left( \frac{m_{ijk} - C_1 s_{ijk1} - C_2 s_{ijk2} - C_3 s_{ijk3} - \ldots - C_{N_s} s_{ijkN_s}}{\sigma_i} \right) \right]^2. \quad (1.4.1\text{-}2)$$

To minimize $\delta_P^2$, differentiate with respect to each of the concentrations and get:

$$\frac{\partial}{\partial C_1} \delta_V^2 \to 0 \Rightarrow \quad (1.4.1\text{-}3a)$$

$$\sum_{i,j \in V} \left[ 2 \left( \frac{m_{ijk} - C_1 s_{ijk1} - C_2 s_{ijk2} - C_3 s_{ijk3} - \ldots}{\sigma_i} \right) \left( \frac{-s_{ijk1}}{\sigma_i} \right) \right] = 0$$

$$\frac{\partial}{\partial C_2} \delta_V^2 \to 0 \Rightarrow \quad (1.4.1\text{-}3b)$$

$$\sum_{i,j \in V} \left[ 2 \left( \frac{m_{ijk} - C_1 s_{ijk1} - C_2 s_{ijk2} - C_3 s_{ijk3} - \ldots}{\sigma_i} \right) \left( \frac{-s_{ijk2}}{\sigma_i} \right) \right] = 0$$

-continued $$\frac{\partial}{\partial C_3}\delta_V^2 \to 0 \Rightarrow \quad (1.4.1\text{-}3c)$$

$$\sum_{i,j\in V}\left[2\left(\frac{m_{ijk} - C_1 s_{ijk1} - C_2 s_{ijk2} - C_3 s_{ijk3} - \ldots}{\sigma_i}\right)\left(\frac{-s_{ijk3}}{\sigma_i}\right)\right] = 0$$

... (1.4.1-3d)

$$\frac{\partial}{\partial C_{N_S}}\delta_V^2 \to 0 \Rightarrow \sum_{i,j\in V}\Bigg[ \quad (1.4.1\text{-}3e)$$

$$2\left(\frac{m_{ijk} - C_1 s_{ijk1} - C_2 s_{ijk2} - C_3 s_{ijk3} - \ldots}{\sigma_i}\right)\left(\frac{-s_{ijkN_S}}{\sigma_i}\right)\Bigg] = 0$$

Simplifying, and using the simpler notation $$\sum_{(i,j,k)\in V} m = \sum_V m \text{ and } \sum_{(i,j,k)\in V} s_{ijk1} = \sum_V s_1$$

$$\sum_V \frac{ms_1}{\sigma^2} - C_1\sum_V \frac{s_1 s_1}{\sigma^2} - C_2\sum_V \frac{s_2 s_1}{\sigma^2} - \quad (1.4.1\text{-}4a)$$
$$C_3\sum_V \frac{s_3 s_1}{\sigma^2} - \ldots C_{N_S}\sum_V \frac{s_{N_S} s_1}{\sigma^2} = 0$$

$$\sum_V \frac{ms_2}{\sigma^2} - C_1\sum_V \frac{s_1 s_3}{\sigma^2} - C_2\sum_V \frac{s_2 s_2}{\sigma^2} - \quad (1.4.1\text{-}4b)$$
$$C_3\sum_V \frac{s_3 s_2}{\sigma^2} - \ldots C_{N_S}\sum_V \frac{s_{N_S} s_2}{\sigma^2} = 0$$

$$\sum_V \frac{ms_3}{\sigma^2} - C_1\sum_V \frac{s_1 s_3}{\sigma^2} - C_2\sum_V \frac{s_2 s_3}{\sigma^2} - \quad (1.4.1\text{-}4c)$$
$$C_3\sum_V \frac{s_3 s_3}{\sigma^2} - \ldots C_{N_S}\sum_V \frac{s_{N_S} s_3}{\sigma^2} = 0$$

... (1.4.1-4d)

$$\sum_V \frac{ms_{N_S}}{\sigma^2} - C_1\sum_V \frac{s_1 s_{N_S}}{\sigma^2} - C_2\sum_V \frac{s_2 s_{N_S}}{\sigma^2} - \quad (1.4.1\text{-}4e)$$
$$C_3\sum_V \frac{s_3 s_{N_S}}{\sigma^2} - \ldots C_{N_S}\sum_V \frac{s_{N_S} s_{N_S}}{\sigma^2} = 0$$

Rearranging, $$C_1\sum_V \frac{s_1 s_1}{\sigma^2} + C_2\sum_V \frac{s_2 s_1}{\sigma^2} + \quad (1.4.1\text{-}5a)$$
$$C_3\sum_V \frac{s_3 s_1}{\sigma^2} + \ldots + C_{N_S}\sum_V \frac{s_{N_S} s_1}{\sigma^2} = \sum_V \frac{ms_1}{\sigma^2}$$

$$C_1\sum_V \frac{s_1 s_2}{\sigma^2} + C_2\sum_V \frac{s_2 s_2}{\sigma^2} + \quad (1.4.1\text{-}5b)$$
$$C_3\sum_V \frac{s_3 s_2}{\sigma^2} + \ldots + C_{N_S}\sum_V \frac{s_{N_S} s_2}{\sigma^2} = \sum_V \frac{ms_2}{\sigma^2}$$

$$C_1\sum_V \frac{s_1 s_3}{\sigma^2} + C_2\sum_V \frac{s_2 s_3}{\sigma^2} + \quad (1.4.1\text{-}5c)$$
$$C_3\sum_V \frac{s_3 s_3}{\sigma^2} + \ldots + C_{N_S}\sum_V \frac{s_{N_S} s_3}{\sigma^2} = \sum_V \frac{ms_3}{\sigma^2}$$

... (1.4.1-5d)

$$C_1\sum_V \frac{s_1 s_{N_S}}{\sigma^2} + C_2\sum_V \frac{s_2 s_{N_S}}{\sigma^2} + \quad (1.4.1\text{-}5e)$$
$$C_3\sum_V \frac{s_3 s_{N_S}}{\sigma^2} \ldots + C_{N_S}\sum_V \frac{s_{N_S} s_{N_S}}{\sigma^2} = \sum_V \frac{ms_{N_S}}{\sigma^2}$$

Which can be written as a matix equation:

$$\begin{bmatrix} \sum_V \frac{s_1 s_1}{\sigma^2} & \sum_V \frac{s_2 s_1}{\sigma^2} & \sum_V \frac{s_3 s_1}{\sigma^2} & \cdots & \sum_V \frac{s_{N_S} s_1}{\sigma^2} \\ \sum_V \frac{s_1 s_2}{\sigma^2} & \sum_V \frac{s_2 s_2}{\sigma^2} & \sum_V \frac{s_3 s_2}{\sigma^2} & \cdots & \sum_V \frac{s_{N_S} s_2}{\sigma^2} \\ \sum_V \frac{s_1 s_3}{\sigma^2} & \sum_V \frac{s_2 s_3}{\sigma^2} & \sum_V \frac{s_3 s_3}{\sigma^2} & \cdots & \sum_V \frac{s_{N_S} s_3}{\sigma^2} \\ \cdots & \cdots & \cdots & \cdots & \cdots \\ \sum_V \frac{s_1 s_{N_S}}{\sigma^2} & \sum_V \frac{s_2 s_{N_S}}{\sigma^2} & \sum_V \frac{s_3 s_{N_S}}{\sigma^2} & \cdots & \sum_V \frac{s_{N_S} s_{N_S}}{\sigma^2} \end{bmatrix} \quad (1.4.1\text{-}6)$$

$$\begin{bmatrix} C_1 \\ C_2 \\ C_3 \\ \cdots \\ C_{N_S} \end{bmatrix} = \begin{bmatrix} \sum_V \frac{ms_1}{\sigma^2} \\ \sum_V \frac{ms_2}{\sigma^2} \\ \sum_V \frac{ms_3}{\sigma^2} \\ \cdots \\ \sum_V \frac{ms_{N_S}}{\sigma^2} \end{bmatrix} \quad (1.4.1\text{-}7)$$

1.4.2 Multiple Patches in 3-D

Multiple patches are handled by stacking the equations for the patches on top of each other vertically: Simplifying, and using the simpler notation $$\sum_{(i,j,k)\in V} m = \sum_V m$$

In the previous section the minimization of $\delta_V^2$ for a single patch was demonstrated. In our case we our more interested in the general case of many patches. We want to minimize the sum of all $\delta_V^2$ as given by:

$$\chi^2 = \sum_{\forall V}\delta_V^2 = \sum_{\forall V}\sum_{(i,j,k)\in V}\left(\frac{m_{ijk} - C_1 s_{ijk1} - C_2 s_{ijk2} - C_3 s_{ijk3} - \ldots - C_{N_S} s_{ijkN_S}}{\sigma_i}\right) \quad (1.4.2\text{-}1)$$

-continued $$\frac{\partial}{\partial C_1}\chi^2 \to 0 \Rightarrow \sum_{\forall V} \sum_{i,j,k \in V} \left[2\left(\frac{(m_{ijk} - C_1 s_{ijk1} - C_2 s_{ijk2} - C_3 s_{ijk3} - \cdots)}{(\sigma_i)}\right)\left(\frac{-s_{ijk1}}{\sigma_i}\right)\right] = 0 \quad (1.4.2\text{-}2a)$$

$$\frac{\partial}{\partial C_2}\chi^2 \to 0 \Rightarrow \sum_{\forall V} \sum_{i,j,k \in V} \left[2\left(\frac{(m_{ijk} - C_1 s_{ijk1} - C_2 s_{ijk2} - C_3 s_{ijk3} - \cdots)}{(\sigma_i)}\right)\left(\frac{-s_{ijk2}}{\sigma_i}\right)\right] = 0 \quad (1.4.2\text{-}2b)$$

$$\frac{\partial}{\partial C_3}\chi^2 \to 0 \Rightarrow \sum_{\forall V} \sum_{i,j,k \in V} \left[2\left(\frac{(m_{ijk} - C_1 s_{ijk1} - C_2 s_{ijk2} - C_3 s_{ijk3} - \cdots)}{(\sigma_i)}\right)\left(\frac{-s_{ijk3}}{\sigma_i}\right)\right] = 0 \quad (1.4.2\text{-}2c)$$

$$\ldots \quad (1.4.2\text{-}2d)$$

$$\frac{\partial}{\partial C_{N_s}}\chi^2 \to 0 \Rightarrow \sum_{\forall V} \sum_{i,j,k \in V} \left[2\left(\frac{(m_{ijk} - C_1 s_{ijk1} - C_2 s_{ijk2} - C_3 s_{ijk3} - \cdots)}{(\sigma_i)}\right)\left(\frac{-s_{ijkN_s}}{\sigma_i}\right)\right] = 0 \quad (1.4.2\text{-}2e)$$

$$\begin{bmatrix} \sum_{\forall V}\sum_V \frac{s_1 s_1}{\sigma^2} & \sum_{\forall V}\sum_V \frac{s_2 s_1}{\sigma^2} & \sum_{\forall V}\sum_V \frac{s_3 s_1}{\sigma^2} & \cdots & \sum_{\forall V}\sum_V \frac{s_{N_s} s_1}{\sigma^2} \\ \sum_{\forall V}\sum_V \frac{s_1 s_2}{\sigma^2} & \sum_{\forall V}\sum_V \frac{s_2 s_2}{\sigma^2} & \sum_{\forall V}\sum_V \frac{s_3 s_2}{\sigma^2} & \cdots & \sum_{\forall V}\sum_V \frac{s_{N_s} s_2}{\sigma^2} \\ \sum_{\forall V}\sum_V \frac{s_1 s_3}{\sigma^2} & \sum_{\forall V}\sum_V \frac{s_2 s_3}{\sigma^2} & \sum_{\forall V}\sum_V \frac{s_3 s_3}{\sigma^2} & \cdots & \sum_{\forall V}\sum_V \frac{s_{N_s} s_3}{\sigma^2} \\ \cdots & \cdots & \cdots & \cdots & \cdots \\ \sum_{\forall V}\sum_V \frac{s_1 s_{N_s}}{\sigma^2} & \sum_{\forall V}\sum_V \frac{s_2 s_{N_s}}{\sigma^2} & \sum_{\forall V}\sum_V \frac{s_1 s_{N_s}}{\sigma^2} & \cdots & \sum_{\forall V}\sum_V \frac{s_{N_s} s_{N_s}}{\sigma^2} \end{bmatrix} \begin{bmatrix} C_1 \\ C_2 \\ C_3 \\ \cdots \\ C_{N_s} \end{bmatrix} = \begin{bmatrix} \sum_{\forall V}\sum_V \frac{m s_1}{\sigma^2} \\ \sum_{\forall V}\sum_V \frac{m s_2}{\sigma^2} \\ \sum_{\forall V}\sum_V \frac{m s_3}{\sigma^2} \\ \cdots \\ \sum_{\forall V}\sum_V \frac{m s_{N_s}}{\sigma^2} \end{bmatrix} \quad (1.4.2\text{-}3)$$

Notice there is no requirement for patches to be sized similarly or located in any special place. The sums are for all elements in a patch, which can be any size or shape.

$$\begin{bmatrix} \sum_{V_1} \frac{s_1 s_1}{\sigma^2} & \sum_{V_1} \frac{s_2 s_1}{\sigma^2} & \sum_{V_1} \frac{s_3 s_1}{\sigma^2} & \cdots & \sum_{V_1} \frac{s_{N_s} s_1}{\sigma^2} \\ \sum_{V_1} \frac{s_1 s_2}{\sigma^2} & \sum_{V_1} \frac{s_2 s_2}{\sigma^2} & \sum_{V_1} \frac{s_3 s_2}{\sigma^2} & \cdots & \sum_{V_1} \frac{s_{N_s} s_2}{\sigma^2} \\ \sum_{V_1} \frac{s_1 s_3}{\sigma^2} & \sum_{V_1} \frac{s_2 s_3}{\sigma^2} & \sum_{V_1} \frac{s_2 s_3}{\sigma^2} & \cdots & \sum_{V_1} \frac{s_{N_s} s_3}{\sigma^2} \\ \cdots & \cdots & \cdots & \cdots & \cdots \\ \sum_{V_1} \frac{s_1 s_{N_s}}{\sigma^2} & \sum_{V_1} \frac{s_2 s_{N_s}}{\sigma^2} & \sum_{V_1} \frac{s_2 s_{N_s}}{\sigma^2} & \cdots & \sum_{V_1} \frac{s_{N_s} s_{N_s}}{\sigma^2} \\ \sum_{V_2} \frac{s_1 s_1}{\sigma^2} & \sum_{V_2} \frac{s_2 s_1}{\sigma^2} & \sum_{V_2} \frac{s_3 s_1}{\sigma^2} & \cdots & \sum_{V_2} \frac{s_{N_s} s_1}{\sigma^2} \\ \sum_{V_2} \frac{s_1 s_2}{\sigma^2} & \sum_{V_2} \frac{s_2 s_2}{\sigma^2} & \sum_{V_2} \frac{s_3 s_2}{\sigma^2} & \cdots & \sum_{V_2} \frac{s_{N_s} s_2}{\sigma^2} \\ \sum_{V_2} \frac{s_1 s_3}{\sigma^2} & \sum_{V_2} \frac{s_2 s_3}{\sigma^2} & \sum_{V_2} \frac{s_3 s_3}{\sigma^2} & \cdots & \sum_{V_2} \frac{s_{N_s} s_3}{\sigma^2} \\ \cdots & \cdots & \cdots & \cdots & \cdots \\ \sum_{V_2} \frac{s_1 s_{N_s}}{\sigma^2} & \sum_{V_2} \frac{s_2 s_{N_s}}{\sigma^2} & \sum_{V_2} \frac{s_3 s_{N_s}}{\sigma^2} & \cdots & \sum_{V_2} \frac{s_{N_s} s_{N_s}}{\sigma^2} \\ \sum_{V_3} \frac{s_1 s_1}{\sigma^2} & \sum_{V_3} \frac{s_2 s_1}{\sigma^2} & \sum_{V_3} \frac{s_3 s_1}{\sigma^2} & \cdots & \sum_{V_3} \frac{s_{N_s} s_1}{\sigma^2} \\ \sum_{V_3} \frac{s_1 s_2}{\sigma^2} & \sum_{V_3} \frac{s_2}{\sigma^2} s_2 & \sum_{V_3} \frac{s_3 s_2}{\sigma^2} & \cdots & \sum_{V_3} \frac{s_{N_s} s_2}{\sigma^2} \\ \sum_{V_3} \frac{s_1 s_3}{\sigma^2} & \sum_{V_3} \frac{s_2 s_3}{\sigma^2} & \sum_{V_3} \frac{s_3 s_3}{\sigma^2} & \cdots & \sum_{V_3} \frac{s_{N_s} s_3}{\sigma^2} \\ \cdots & \cdots & \cdots & \cdots & \cdots \end{bmatrix} \begin{bmatrix} C_1 \\ C_2 \\ C_3 \\ \cdots \\ C_{N_s} \end{bmatrix} = \begin{bmatrix} \sum_{V_1} \frac{m s_1}{\sigma^2} \\ \sum_{V_1} \frac{m s_2}{\sigma^2} \\ \sum_{V_1} \frac{m s_3}{\sigma^2} \\ \cdots \\ \sum_{V_1} \frac{m s_{N_s}}{\sigma^2} \\ \sum_{V_2} \frac{m s_1}{\sigma^2} \\ \sum_{V_2} \frac{m s_2}{\sigma^2} \\ \sum_{V_2} \frac{m s_3}{\sigma^2} \\ \cdots \\ \sum_{V_2} \frac{m s_{N_s}}{\sigma^2} \\ \sum_{V_3} \frac{m s_1}{\sigma^2} \\ \sum_{V_3} \frac{m s_2}{\sigma^2} \\ \sum_{V_3} \frac{m s_3}{\sigma^2} \\ \cdots \end{bmatrix} \quad (1.4.3\text{-}1)$$

-continued $$\begin{bmatrix} \sum_{V_3} \frac{s_1 s_{N_s}}{\sigma^2} & \sum_{V_3} \frac{s_2 s_{N_s}}{\sigma^2} & \sum_{V_3} \frac{s_3 s_{N_s}}{\sigma^2} & \cdots & \sum_{V_3} \frac{s_{N_s} s_{N_s}}{\sigma^2} \\ \cdots & \cdots & \cdots & \cdots & \cdots \\ \sum_{V_N} \frac{s_1 s_1}{\sigma^2} & \sum_{V_N} \frac{s_2 s_1}{\sigma^2} & \sum_{V_N} \frac{s_3 s_1}{\sigma^2} & \cdots & \sum_{V_N} \frac{s_{N_s} s_1}{\sigma^2} \\ \sum_{V_N} \frac{s_1 s_2}{\sigma^2} & \sum_{V_N} \frac{s_2 s_2}{\sigma^2} & \sum_{V_N} \frac{s_3 s_2}{\sigma^2} & \cdots & \sum_{V_N} \frac{s_{N_s} s_2}{\sigma^2} \\ \sum_{V_N} \frac{s_1 s_3}{\sigma^2} & \sum_{V_N} \frac{s_2 s_3}{\sigma^2} & \sum_{V_N} \frac{s_3 s_3}{\sigma^2} & \cdots & \sum_{V_N} \frac{s_{N_s} s_3}{\sigma^2} \\ \cdots & \cdots & \cdots & \cdots & \cdots \\ \sum_{V_N} \frac{s_1 s_{N_s}}{\sigma^2} & \sum_{V_N} \frac{s_2 s_{N_s}}{\sigma^2} & \sum_{V_N} \frac{s_3 s_{N_s}}{\sigma^2} & \cdots & \sum_{V_N} \frac{s_{N_s} s_{N_s}}{\sigma^2} \end{bmatrix} \begin{bmatrix} \sum_{V_3} \frac{m s_{N_s}}{\sigma^2} \\ \cdots \\ \sum_{V_N} \frac{m s_1}{\sigma^2} \\ \sum_{V_N} \frac{m s_2}{\sigma^2} \\ \sum_{V_N} \frac{m s_3}{\sigma^2} \\ \cdots \\ \sum_{V_N} \frac{m s_{N_s}}{\sigma^2} \end{bmatrix}$$

1.5 Error Analysis
1.5.1 'Traditional' 1-D Chemometrics $$[M] = [m_1 \, m_2 \, m_3 \ldots m_n] \qquad (1.5\text{-}1)$$

$$[S_1] = [s_{1l} \, s_{2l} \, s_{3l} \ldots s_{nl}] \qquad (1.5\text{-}2)$$

Since [M] is assumed to be made up of a linear combinations of the samples, [M] can be written as:

$$[M] = C_1[S_1] + C_2[S_2] + C_3[S_s] + \ldots + C_{N_s}[S_{N_s}] + \text{noise.} \qquad (1.5\text{-}3)$$

$$[m_1 m_2 m_3 \ldots m_n] = \qquad (1.5\text{-}4)$$
$$C_1[s_{11} s_{21} s_{31} \ldots s_{n1}] + C_2[s_{12} s_{22} s_{32} \ldots s_{n2}] + \ldots + \text{noise}$$

$$\delta_i^2 = \left( \frac{m_i - C_1 s_{il} - C_2 s_{i2} - C_3 s_{i3} - \ldots - C_{N_s} s_{iN_s}}{\sigma_i} \right)^2, \qquad (1.5\text{-}5)$$

$$\chi^2 = \sum_{i=1,n} \delta_i^2 = \sum_{i=1,n} \left( \frac{m_i - C_1 s_{il} - C_2 s_{i2} - C_3 s_{i3} - \ldots - C_{N_s} s_{iN_s}}{\sigma_i} \right) \qquad (1.5\text{-}6)$$

To minimize $\chi^2$, differentiate with respect to each of the concentrations and get:

$$\frac{\partial}{\partial C^1} \chi^2 \to 0 \Rightarrow \qquad (1.5\text{-}7a)$$
$$\sum_{i=1,n} \left( 2 \left( \frac{m_i - C_1 s_{il} - C_2 s_{i2} - C_3 s_{i3} - \ldots}{\sigma_i} \right) \left( \frac{-s_{il}}{\sigma_i} \right) \right) = 0$$

$$\frac{\partial}{\partial C^2} \chi^2 \to 0 \Rightarrow \qquad (1.5\text{-}7b)$$
$$\sum_{i=1,n} \left( 2 \left( \frac{m_i - C_1 s_{il} - C_2 s_{i2} - C_3 s_{i3} - \ldots}{\sigma_i} \right) \left( \frac{-s_{i2}}{\sigma_i} \right) \right) = 0$$

$$\frac{\partial}{\partial C^3} \chi^2 \to 0 \Rightarrow \qquad (1.5\text{-}7c)$$
$$\sum_{i=1,n} \left( 2 \left( \frac{m_i - C_1 s_{il}^1 - C_2 s_{i2} - C_3 s_{i3} - \ldots}{\sigma_i} \right) \left( \frac{-s_i^3}{\sigma_i} \right) \right) = 0$$

$$\ldots \qquad (1.5\text{-}7d)$$

$$\frac{\partial}{\partial C^{N_s}} \chi^2 \to 0 \Rightarrow \qquad (1.5\text{-}7e)$$
$$\sum_{i=1,n} \left( 2 \left( \frac{m_i - C_1 s_{il} - C_2 s_{i2} - C_3 s_{i3} - \ldots}{\sigma_i} \right) \left( \frac{-s_{iN_s}}{\sigma_i} \right) \right) = 0$$

which is of the form, $$[A] \cdot [C] = [B] \qquad (1.5\text{-}8)$$

If we define $$[\alpha] = \qquad (1.5\text{-}9)$$

$$\begin{bmatrix} \sum_i \frac{s_{il} s_{il}}{\sigma_i^2} & \sum_i \frac{s_{i2} s_{il}}{\sigma_i^2} & \sum_i \frac{s_{i3} s_{il}}{\sigma_i^2} & \cdots & \sum_i \frac{s_{iN_s} s_{il}}{\sigma_i^2} \\ \sum_i \frac{s_{il} s_{i2}}{\sigma_i^2} & \sum_i \frac{s_{i2} s_{i2}}{\sigma_i^2} & \sum_i \frac{s_{i3} s_{i2}}{\sigma_i^2} & \cdots & \sum_i \frac{s_{iN_s} s_{i2}}{\sigma_i^2} \\ \sum_i \frac{s_{il} s_{i3}}{\sigma_i^2} & \sum_i \frac{s_{i2} s_{i3}}{\sigma_i^2} & \sum_i \frac{s_{i3} s_{i3}}{\sigma_i^2} & \cdots & \sum_i \frac{s_{iN_s} s_{i3}}{\sigma_i^2} \\ \cdots & \cdots & \cdots & \cdots & \cdots \\ \sum_i \frac{s_{il} s_{iN_s}}{\sigma_i^2} & \sum_i \frac{s_{i2} s_{iN_s}}{\sigma_i^2} & \sum_i \frac{s_{i3} s_{iN_s}}{\sigma_i^2} & \cdots & \sum_i \frac{s_{iN_s} s_{iN_s}}{\sigma_i^2} \end{bmatrix}$$

$$[C] = \begin{bmatrix} C_1 \\ C_2 \\ C_3 \\ \cdots \\ C_{N_s} \end{bmatrix} \qquad (1.5\text{-}10)$$

$$[\beta] = \begin{bmatrix} \sum_i \frac{m_i s_{il}}{\sigma_i^2} \\ \sum_i \frac{m_i s_{i2}}{\sigma_i^2} \\ \sum_i \frac{m_i s_{i3}}{\sigma_i^2} \\ \cdots \\ \sum_i \frac{m_i s_{iN_s}}{\sigma_i^2} \end{bmatrix} \qquad (1.5\text{-}11)$$

$$\sum_{n=1,N_s} \alpha^{mn} C^n = \beta^m, \quad \forall m = 1, N_s \qquad (1.5\text{-}12)$$

Then using SVD, . . .

$$[\alpha] = [U] \cdot \begin{bmatrix} w_1 & & & & \\ & w_2 & & & \\ & & w_3 & & \\ & & & \cdots & \\ & & & & w_N \end{bmatrix} \cdot [V^T] \qquad (1.5\text{-}13)$$

-continued $$[\alpha]^{-1} = [V] \cdot \begin{bmatrix} 1/w_1 & & & & \\ & 1/w_2 & & & \\ & & 1/w_3 & & \\ & & & \ldots & \\ & & & & 1/w_N \end{bmatrix} \cdot [U^T] \quad (1.5\text{-}14)$$

So that $$[C] = [V] \cdot \begin{bmatrix} 1/w_1 & & & & \\ & 1/w_2 & & & \\ & & 1/w_3 & & \\ & & & \ldots & \\ & & & & 1/w_N \end{bmatrix} \cdot [U^T] \cdot [\beta] \quad (1.5\text{-}15)$$

which is of the form, $$[A] \cdot [C] = [B] \quad (1.5\text{-}16)$$

Now what is the uncertainty of C? three terms $$\sigma^2(C^l) = \sum_i^N \left( \delta m_i^2 \left( \frac{\partial C^l}{\partial m_i} \right)^2 + \delta m_i \delta s_i \partial\, C^l \frac{\partial\, C^l}{\partial m_i \partial\, s_i} + \delta s_i^2 \left( \frac{\partial C^l}{\partial s_i} \right)^2 \right) \quad (1.5\text{-}17)$$

Error analysis derivation based on the assumption that $$\sigma^2(c_l) = \sum_p \left( \sigma^2(m_p) \left( \frac{\partial c_l}{\partial m_p} \right)^2 + \right.$$

$$\sum_k \sigma(m_p)\sigma(s_{pk}) \frac{\partial c_l \partial\, c_l}{\partial m \partial s} +$$

$$\left. \sum_k \sigma^2(s_{pk}) \left( \frac{\partial c_l}{\partial s} \right)^2 \right) \quad (1.5\text{-}18)$$

the first term is commonly found and the others are commonly ignored. This is because it is usually assumed that the fitting functions are exact, or in the case of curve fitting the locations x at which measurements y are taken are known exactly. This leads to the curious result if the uncertainty of all measurements are equal then the variances of the fitted parameters (the intercept and slope in line fitting) depend only the x's and not the y's. In our case this is not true. both the mixture and the database samples have measurement uncertainties associated with them.

Definitions . . .

$m_p \Rightarrow$ mixture element at pixel p $s_{pk} \Rightarrow$ sample k element at pixel p $c_l \Rightarrow$ concentration of sample l $\sigma^2(c_l) \Rightarrow$ variance of the estimated concentration $c_l$ $\sigma^2(m_p) \Rightarrow$ variance of $m_p$ $\sigma^2(s_{pk}) \Rightarrow$ variance of $s_{pk}$ To simplify the derivation, consider the basic equation (repeated subscripts indicate summation)

$$\begin{bmatrix} s_{i1}s_{i1} & s_{i1}s_{i2} & s_{i1}s_{i3} \\ s_{i2}s_{i1} & s_{i2}s_{i2} & s_{i2}s_{i3} \\ s_{i3}s_{i1} & s_{i3}s_{i2} & s_{i3}s_{i3} \end{bmatrix} \begin{bmatrix} c_1 \\ c_2 \\ c_3 \end{bmatrix} = \begin{bmatrix} m_i s_{i1} \\ m_i s_{i2} \\ m_i s_{i3} \end{bmatrix} \quad (1.5\text{-}20)$$

$$\begin{bmatrix} a_{11} & a_{12} & a_{13} \\ a_{21} & a_{22} & a_{23} \\ a_{31} & a_{32} & a_{33} \end{bmatrix} \begin{bmatrix} c_1 \\ c_2 \\ c_3 \end{bmatrix} = \begin{bmatrix} m_i s_{i1} \\ m_i s_{i2} \\ m_i s_{i3} \end{bmatrix} \quad (1.5\text{-}21)$$

in the non-square patch case it will look like $$\begin{bmatrix} (s_{i1}s_{i1})_a & (s_{i1}s_{i2})_a & (s_{i1}s_{i3})_a \\ (s_{i2}s_{i1})_a & (s_{i2}s_{i2})_a & (s_{i2}s_{i3})_a \\ (s_{i3}s_{i1})_a & (s_{i3}s_{i2})_a & (s_{i3}s_{i3})_a \\ (s_{i1}s_{i1})_b & (s_{i1}s_{i2})_b & (s_{i1}s_{i3})_b \\ (s_{i2}s_{i1})_b & (s_{i2}s_{i2})_b & (s_{i2}s_{i3})_b \\ (s_{i3}s_{i1})_b & (s_{i3}s_{i2})_b & (s_{i3}s_{i3})_b \end{bmatrix} \begin{bmatrix} c_1 \\ c_2 \\ c_3 \end{bmatrix} = \quad (1.5\text{-}22)$$

$$\begin{bmatrix} a_{11} & a_{12} & a_{13} \\ a_{21} & a_{22} & a_{23} \\ a_{31} & a_{32} & a_{33} \\ a_{41} & a_{42} & a_{43} \\ a_{51} & a_{52} & a_{53} \\ a_{61} & a_{62} & a_{63} \end{bmatrix} \begin{bmatrix} c_1 \\ c_2 \\ c_3 \end{bmatrix} = \begin{bmatrix} (ms_1)_a \\ (ms_2)_a \\ (ms_3)_a \\ (ms_1)_b \\ (ms_2)_b \\ (ms_3)_b \end{bmatrix}$$

for patch a and b . . .

Note the matrix on the left does not need to be square, . . . it will have a pseudo-inverse as long as the problem is well posed. Then the concentrations can be solved for, by computing $[\alpha]$, the pseudo inverse of $[a]$. Here we define a pseudo inverse to be the non-square matrix $[\alpha]$ which has the property $$[\alpha][a] = \begin{bmatrix} 1 & 0 & 0 \\ 0 & \ldots & 0 \\ 0 & 0 & 1 \end{bmatrix}$$

(a square matrix with zero's everywhere except 1's on the diagonals).

$$\begin{bmatrix} s_{i1}s_{i1} & s_{i1}s_{i2} & s_{i1}s_{i3} \\ s_{i2}s_{i1} & s_{i2}s_{i2} & s_{i2}s_{i3} \\ s_{i3}s_{i1} & s_{i3}s_{i2} & s_{i3}s_{i3} \end{bmatrix} = \begin{bmatrix} a_{11} & a_{12} & a_{13} \\ a_{21} & a_{22} & a_{23} \\ a_{31} & a_{32} & a_{33} \end{bmatrix} \quad (1.5\text{-}23)$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix} \begin{bmatrix} a_{11} & a_{12} & a_{13} \\ a_{21} & a_{22} & a_{23} \\ a_{31} & a_{32} & a_{33} \end{bmatrix} = \begin{bmatrix} 1 & 0 & 0 \\ 0 & 1 & 0 \\ 0 & 0 & 1 \end{bmatrix} \quad (1.5\text{-}24)$$

$$\begin{bmatrix} c_1 \\ c_2 \\ c_3 \end{bmatrix} = \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix} \begin{bmatrix} m_i s_{i1} \\ m_i s_{i2} \\ m_i s_{i3} \end{bmatrix} \quad (1.5\text{-}25)$$

For the purpose of this derivation we assume the pseudo inverse can computed at will. In practice we will use singular value decomposition, which not only provides the inverse, but does so in a form that is particularly useful and remarkably free from numerical problems.

Now to compute the derivative terms . . .

$$\frac{\partial}{\partial s_{pc}} \begin{bmatrix} c_1 \\ c_2 \\ c_3 \end{bmatrix} = \frac{\partial}{\partial s_{pc}} \left( \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix} \begin{bmatrix} m_i s_{i1} \\ m_i s_{i2} \\ m_i s_{i3} \end{bmatrix} \right) \quad (1.5\text{-}26)$$

$$\frac{\partial}{\partial s_{pc}}\begin{bmatrix} c_1 \\ c_2 \\ c_3 \end{bmatrix} = -\left(\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix} \frac{\partial}{\partial s_{pc}}\left(\begin{bmatrix} s_{i1}s_{i1} & s_{i2}s_{i1} & s_{i3}s_{i1} \\ s_{i1}s_{i2} & s_{i2}s_{i2} & s_{i3}s_{i2} \\ s_{i1}s_{i3} & s_{i2}s_{i3} & s_{i3}s_{i3} \end{bmatrix}\right)\right) \quad (1.5\text{-}27)$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_1s_{11}+m_2s_{21}+m_3s_{31} \\ m_1s_{12}+m_2s_{22}+m_3s_{32} \\ m_1s_{13}+m_2s_{23}+m_3s_{33} \end{bmatrix}\right) +$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\frac{\partial}{\partial s_{pc}}[$$

Note the rule (a and $\alpha$ are pseudo inverses of each other)

$$\frac{\partial}{\partial s}a\alpha = \frac{\partial a}{\partial s}\alpha + a\frac{\partial \alpha}{\partial s} = \frac{\partial}{\partial s}\begin{bmatrix} 1 & 0 & 0 \\ 0 & 1 & 0 \\ 0 & 0 & 1 \end{bmatrix} = [0] \quad (1.5\text{-}28)$$

with the result $$\frac{\partial \alpha}{\partial s} = -\alpha \frac{\partial a}{\partial s}\alpha \quad (1.5\text{-}29)$$

this enables us to take the derivative functionally $$\frac{\partial}{\partial s_{p1}}\begin{bmatrix} c_1 \\ c_2 \\ c_3 \end{bmatrix} = -\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} 2s_{p1} & s_{p2} & s_{p3} \\ s_{p2} & 0 & 0 \\ s_{p3} & 0 & 0 \end{bmatrix} \quad (1.5\text{-}30)$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_1s_{11}+m_2s_{21}+m_3s_{31} \\ m_1s_{12}+m_2s_{22}+m_3s_{32} \\ m_1s_{13}+m_2s_{23}+m_3s_{33} \end{bmatrix} +$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_p \\ 0 \\ 0 \end{bmatrix}$$

$c = 1$ $$\frac{\partial}{\partial s_{p2}}\begin{bmatrix} c_1 \\ c_2 \\ c_3 \end{bmatrix} = -\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} 0 & s_{p1} & 0 \\ s_{p1} & 2s_{p2} & s_{p3} \\ 0 & s_{p3} & 0 \end{bmatrix} \quad (1.5\text{-}31)$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_1s_{11}+m_2s_{21}+m_3s_{31} \\ m_1s_{12}+m_2s_{22}+m_3s_{32} \\ m_1s_{13}+m_2s_{23}+m_3s_{33} \end{bmatrix} +$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} 0 \\ m_p \\ 0 \end{bmatrix}$$

$c = 2$ $$\frac{\partial}{\partial s_{p3}}\begin{bmatrix} c_1 \\ c_2 \\ c_3 \end{bmatrix} = -\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} 0 & 0 & s_{p1} \\ 0 & 0 & s_{p2} \\ s_{p1} & s_{p2} & 2s_{p3} \end{bmatrix} \quad (1.5\text{-}32)$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_1s_{11}+m_2s_{21}+m_3s_{31} \\ m_1s_{12}+m_2s_{22}+m_3s_{32} \\ m_1s_{13}+m_2s_{23}+m_3s_{33} \end{bmatrix} +$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} 0 \\ 0 \\ m_p \end{bmatrix}$$

$c = 3$ recognizing that the product of the two central matrixes is just the concentration matrix, and bringing the right hand term into the product, $$\frac{\partial}{\partial s_{p1}}\begin{bmatrix} c_1 \\ c_2 \\ c_3 \end{bmatrix} = -\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} 2s_{p1} & s_{p2} & s_{p3} \\ s_{p2} & 0 & 0 \\ s_{p3} & 0 & 0 \end{bmatrix} \quad (1.5\text{-}33)$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_1s_{11}+m_2s_{21}+m_3s_{31} \\ m_1s_{12}+m_2s_{22}+m_3s_{32} \\ m_1s_{13}+m_2s_{23}+m_3s_{33} \end{bmatrix} +$$

$$\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_p \\ 0 \\ 0 \end{bmatrix}$$

$$\frac{\partial}{\partial s_{p1}}\begin{bmatrix} c_1 \\ c_2 \\ c_3 \end{bmatrix} = \left(\begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\right) \quad (1.5\text{-}34)$$

$$\left(-\begin{bmatrix} 2s_{p1} & s_{p2} & s_{p3} \\ s_{p2} & 0 & 0 \\ s_{p3} & 0 & 0 \end{bmatrix}\begin{bmatrix} c_1 \\ c_2 \\ c_3 \end{bmatrix} + \begin{bmatrix} m_p \\ 0 \\ 0 \end{bmatrix}\right)$$

Simplifying, $$\frac{\partial}{\partial s_{p1}}\begin{bmatrix} c_1 \\ c_2 \\ c_3 \end{bmatrix} = \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} m_p - 2c_1 s_{p1} - c_2 s_{p2} - c_3 s_{p3} \\ -c_1 s_{p2} \\ -c_1 s_{p3} \end{bmatrix} \quad (1.5\text{-}35)$$

$$\frac{\partial}{\partial s_{p2}}\begin{bmatrix} c_1 \\ c_2 \\ c_3 \end{bmatrix} = \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} -c_2 s_{p1} \\ m_p - c_1 s_{p1} - 2c_2 s_{p2} - c_3 s_{p3} \\ -c_2 s_{p3} \end{bmatrix} \quad (1.5\text{-}36)$$

$$\frac{\partial}{\partial s_{p3}}\begin{bmatrix} c_1 \\ c_2 \\ c_3 \end{bmatrix} = \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} -c_3 s_{p1} \\ -c_3 s_{p2} \\ m_p - c_1 s_{p1} - c_2 s_{p2} - 2c_3 s_{p3} \end{bmatrix} \quad (1.5\text{-}37)$$

Now generalize a little bit, so we don't have to repaint three equations over and over, explicitly writing out the sum on j for now. The kronecker delta is used.

$$\frac{\partial}{\partial s_{pl}}\begin{bmatrix} c_1 \\ c_2 \\ c_3 \end{bmatrix} = \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} -c_l s_{p1} \\ -c_l s_{p2} \\ -c_l s_{p3} - \delta_{l3}\left(-m_p + \sum_j s_{pj}c_j\right) \end{bmatrix} \quad (1.5\text{-}38)$$

$$\frac{\partial}{\partial s_{pl}}\begin{bmatrix} c_1 \\ c_2 \\ c_3 \end{bmatrix} = \begin{bmatrix} \alpha_{11} & \alpha_{12} & \alpha_{13} \\ \alpha_{21} & \alpha_{22} & \alpha_{23} \\ \alpha_{31} & \alpha_{32} & \alpha_{33} \end{bmatrix}\begin{bmatrix} -c_l s_{p1} - \delta_{1l}\left(-m_p + \sum_j s_{pj}c_j\right) \\ -c_l s_{p2} - \delta_{2l}\left(-m_p + \sum_j s_{pj}c_j\right) \\ -c_l s_{p3} - \delta_{3l}\left(-m_p + \sum_j s_{pj}c_j\right) \end{bmatrix} \quad (1.5\text{-}39)$$

$$\frac{\partial}{\partial s_{pl}}\begin{bmatrix}c_1\\c_2\\c_3\end{bmatrix} = \quad (1.5\text{-}40)$$

$$\left(\frac{-1}{c_l}\right)\left\{\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}s_{p1}\\s_{p2}\\s_{p3}\end{bmatrix} + \begin{bmatrix}c_l\delta_{1l}\left(-m_p+\sum_j s_{pj}c_j\right)\\ c_l\delta_{2l}\left(-m_p+\sum_j s_{pj}c_j\right)\\ c_l\delta_{3l}\left(-m_p+\sum_j s_{pj}c_j\right)\end{bmatrix}\right\}$$

$$\frac{\partial}{\partial s_{pl}}\begin{bmatrix}c_1\\c_2\\c_3\end{bmatrix} = \left(\frac{-1}{c_l}\right)\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}s_{p1}\\s_{p2}\\s_{p3}\end{bmatrix} + \quad (1.5\text{-}41)$$

$$\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}\delta_{1l}(-m_p+\sum s_{pj}c_j)\\ \delta_{2l}(-m_p+\sum s_{pj}c_j)\\ \delta_{3l}(-m_p+\sum s_{pj}c_j)\end{bmatrix}$$

Consider the product, for l=1

$$\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}-m_p+\sum s_{pj}c_j\\ 0\\ 0\end{bmatrix} = \begin{bmatrix}\alpha_{11}-m_p+\sum s_{pj}c_j\\ \alpha_{21}-m_p+\sum s_{pj}c_j\\ \alpha_{31}-m_p+\sum s_{pj}c_j\end{bmatrix} \quad (1.5\text{-}42)$$

and for l=2

$$\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}0\\ -m_p+\sum s_{pj}c_j\\ 0\end{bmatrix} = \begin{bmatrix}\alpha_{12}-m_p+\sum s_{pj}c_j\\ \alpha_{22}-m_p+\sum s_{pj}c_j\\ \alpha_{32}-m_p+\sum s_{pj}c_j\end{bmatrix} \quad (1.5\text{-}43)$$

so that in general $$\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}\delta_{1l}(-m_p+\sum s_{pj}c_j)\\ \delta_{2l}(-m_p+\sum s_{pj}c_j)\\ \delta_{3l}(-m_p+\sum s_{pj}c_j)\end{bmatrix} = \quad (1.5\text{-}44)$$

$$\begin{bmatrix}\alpha_{1l}-m_p+\sum s_{pj}c_j\\ \alpha_{2l}-m_p+\sum s_{pj}c_j\\ \alpha_{3l}-m_p+\sum s_{pj}c_j\end{bmatrix}$$

and therefore $$\frac{\partial}{\partial s_{pl}}\begin{bmatrix}c_1\\c_2\\c_3\end{bmatrix} = \left(\frac{-1}{c_l}\right)\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}s_{p1}\\s_{p2}\\s_{p3}\end{bmatrix} + \quad (1.5\text{-}45)$$

$$\begin{bmatrix}\alpha_{1l}-m_p+\sum s_{pj}c_j\\ \alpha_{2l}-m_p+\sum s_{pj}c_j\\ \alpha_{3l}-m_p+\sum s_{pj}c_j\end{bmatrix}$$

now note the presence of the residual r $$\frac{\partial}{\partial s_{pl}}\begin{bmatrix}c_1\\c_2\\c_3\end{bmatrix} = \left(\frac{-1}{c_l}\right)\begin{bmatrix}\alpha_{11} & \alpha_{12} & \alpha_{13}\\ \alpha_{21} & \alpha_{22} & \alpha_{23}\\ \alpha_{31} & \alpha_{32} & \alpha_{33}\end{bmatrix}\begin{bmatrix}s_{p1}\\s_{p2}\\s_{p3}\end{bmatrix} + \begin{bmatrix}\alpha_{1l}-r\\ \alpha_{2l}-r\\ \alpha_{3l}-r\end{bmatrix} \quad (1.5\text{-}46)$$

or for a particular concentration $$\frac{\partial c_1}{\partial s_{pl}} = \left(\frac{-1}{c_l}\right)(\alpha_{11}s_{p1}+\alpha_{12}s_{p2}+\alpha_{13}s_{p3})+\alpha_{1l}-r \quad (1.5\text{-}47)$$

now to compute the squared value, $$\left(\frac{\partial c_1}{\partial s_{pl}}\right)^2 = \left(\left(\frac{-1}{c_l}\right)(\alpha_{11}s_{p1}+\alpha_{12}s_{p2}+\alpha_{13}s_{p3})+\alpha_{1l}-r\right) \quad (1.5\text{-}48)$$

$$\left(\left(\frac{-1}{c_l}\right)(\alpha_{11}s_{p1}+\alpha_{12}s_{p2}+\alpha_{13}s_{p3})+\alpha_{1l}-r\right)$$

$$\left(\frac{\partial c_1}{\partial s_{pl}}\right)^2 = \left(\frac{-1}{c_l}\right)^2(\alpha_{11}s_{p1}+\alpha_{12}s_{p2}+\alpha_{13}s_{p3})^2 + \quad (1.5\text{-}49)$$

$$\left(\frac{-2}{c_l}\right)(\alpha_{11}s_{p1}+\alpha_{12}s_{p2}+\alpha_{13}s_{p3})(\alpha_{1l}-r)+(\alpha_{1l}-r)^2$$

in summation notation . . .

$$\left(\frac{\partial c_1}{\partial s_{pl}}\right)^2 = \left(\frac{1}{c_l}\right)^2(\alpha_{1i}\alpha_{1j}s_{pi}s_{pj})+ \quad (1.5\text{-}50)$$

$$\left(\frac{-2}{c_l}\right)(\alpha_{1i}s_{pi})(\alpha_{1l}-r)+(\alpha_{1l}-r)^2$$

summing over all pixels . . .

$$\sum_p\left(\frac{\partial c_1}{\partial s_{pl}}\right)^2 = \sum_p\left(\left(\frac{1}{c_l}\right)^2(\alpha_{1i}\alpha_{1j}s_{pi}s_{pj})+ \right. \quad (1.5\text{-}51)$$

$$\left. \left(\frac{-2}{c_l}\right)(\alpha_{1i}s_{pi})(\alpha_{1l}-r)+(\alpha_{1l}-r)^2\right)$$

$$\begin{bmatrix}\alpha_{1j}s_{pj}s_{p1} & \alpha_{1j}s_{pj}s_{p2} & \alpha_{1j}s_{pj}s_{p3}\\ \alpha_{2j}s_{pj}s_{p1} & \alpha_{2j}s_{pj}s_{p2} & \alpha_{2j}s_{pj}s_{p3}\\ \alpha_{3j}s_{pj}s_{p1} & \alpha_{3j}s_{pj}s_{p2} & \alpha_{3j}s_{pj}s_{p3}\end{bmatrix} = \begin{bmatrix}1 & 0 & 0\\ 0 & 1 & 0\\ 0 & 0 & 1\end{bmatrix} \quad (1.5\text{-}52)$$

$$\sum_p\left(\frac{\partial c_1}{\partial s_{pl}}\right)^2 = \quad (1.5\text{-}53)$$

$$\left(\frac{1}{c_l}\right)^2(\alpha_{11}) + \left(\frac{-2}{c_l}\right)\left(\sum_p\alpha_{1i}s_{pi}\right)(\alpha_{1l}-r) + \sum_p(\alpha_{1l}-r)^2$$

$$\sum_p \left(\frac{\partial c_1}{\partial s_{pl}}\right)^2 = \qquad (1.5\text{-}54)$$

$$\left(\frac{1}{c_l}\right)^2 (\alpha_{11}) + \sum_p \left(\left(\frac{-2}{c_l}\right)(\alpha_{1i}s_{pi})(\alpha_{1l} - r) + (\alpha_{1l} - r)^2\right)$$

$$\sum_p \left(\frac{\partial c_1}{\partial s_{pl}}\right)^2 = \qquad (1.5\text{-}55)$$

$$\left(\frac{1}{c_l}\right)^2 (\alpha_{11}) + \frac{-2}{c_l}\sum_p (\alpha_{1i}s_{pi}(\alpha_{1l} - r)) + \sum_p (\alpha_{1l} - r)^2$$

The first term is rather remarkable, it is just $1/c^2$ times the classical result. for the first time we see the variance getting bigger as the concentration gets smaller. Also note the scaling for as the residual grows the variance grows rapidly. This will be a great indication that chemical are missing from the database.

this equation can now be plugged into the first equation in this chapter.

For completeness, . . .

$$r_p = m_p - s_{pj}c_j \qquad (1.5\text{-}56)$$

summation implied . . .

$$\sum_p \left(\frac{\partial c_1}{\partial s_{pl}}\right)^2 = \qquad (1.5\text{-}57)$$

$$\left(\frac{1}{c_l}\right)^2 (\alpha_{11}) + \frac{-2}{c_l}\sum_p (\alpha_{1i}s_{pi}\alpha_{1l} - \alpha_{1i}s_{pi}m_p + \alpha_{1i}s_{pi}s_{pj}c_j) +$$

$$\sum_p (\alpha_{1l} - m_p + s_{pj}c_j)^2$$

Now to compute the 'classical result' . . . the Rate of change of concentration estimate with respect to mixture pixel variance.

Using a double subscript i to indicate a sum over pixels different from p . . .

$$\frac{\partial}{\partial m_p}\begin{bmatrix}c_1\\c_2\\c_3\end{bmatrix} = \frac{\partial}{\partial m_p}\left(\begin{bmatrix}\alpha_{11}&\alpha_{12}&\alpha_{13}\\\alpha_{21}&\alpha_{22}&\alpha_{23}\\\alpha_{31}&\alpha_{32}&\alpha_{33}\end{bmatrix}\begin{bmatrix}m_is_{i1}\\m_is_{i2}\\m_is_{i3}\end{bmatrix}\right) \qquad (1.5\text{-}58)$$

$$\frac{\partial}{\partial m_p}\begin{bmatrix}c_1\\c_2\\c_3\end{bmatrix} = \begin{bmatrix}\alpha_{11}&\alpha_{12}&\alpha_{13}\\\alpha_{21}&\alpha_{22}&\alpha_{23}\\\alpha_{31}&\alpha_{32}&\alpha_{33}\end{bmatrix}\begin{bmatrix}\frac{\partial}{\partial m_p}m_is_{i1}\\\frac{\partial}{\partial m_p}m_is_{i2}\\\frac{\partial}{\partial m_p}m_is_{i3}\end{bmatrix} \qquad (1.5\text{-}59)$$

Noting $$\begin{bmatrix}\frac{\partial}{\partial m_p}m_is_{i1}\\\frac{\partial}{\partial m_p}m_is_{i2}\\\frac{\partial}{\partial m_p}m_is_{i3}\end{bmatrix} = \begin{bmatrix}s_{p1}\\s_{p2}\\s_{p3}\end{bmatrix} \qquad (1.5\text{-}60)$$

Note, $$\begin{bmatrix}\alpha_{11}&\alpha_{12}&\alpha_{13}\\\alpha_{21}&\alpha_{22}&\alpha_{23}\\\alpha_{31}&\alpha_{32}&\alpha_{33}\end{bmatrix}\begin{bmatrix}s_{p1}\\s_{p2}\\s_{p3}\end{bmatrix} = \begin{bmatrix}\alpha_{11}s_{p1}+\alpha_{12}s_{p2}+\alpha_{13}s_{p3}\\\alpha_{21}s_{p1}+\alpha_{22}s_{p2}+\alpha_{23}s_{p3}\\\alpha_{31}s_{p1}+\alpha_{32}s_{p2}+\alpha_{33}s_{p3}\end{bmatrix} \qquad (1.5\text{-}61)$$

using the summation convention on i and j and dropping the subscript p for now . . .

$$\begin{bmatrix}(\alpha_{11}s_{p1}+\alpha_{12}s_{p2}+\alpha_{13}s_{p3})^2\\(\alpha_{21}s_{p1}+\alpha_{22}s_{p2}+\alpha_{23}s_{p3})^2\\(\alpha_{31}s_{p1}+\alpha_{32}s_{p2}+\alpha_{33}s_{p3})^2\end{bmatrix} = \begin{bmatrix}\alpha_{1i}\alpha_{1j}s_js_j\\\alpha_{2i}\alpha_{2j}s_is_j\\\alpha_{3i}\alpha_{3j}s_is_j\end{bmatrix} \qquad (1.5\text{-}62)$$

$$\sum_p \begin{bmatrix}\left(\frac{\partial}{\partial m_p}c_1\right)^2\\\left(\frac{\partial}{\partial m_p}c_2\right)^2\\\left(\frac{\partial}{\partial m_p}c_3\right)^2\end{bmatrix} = \sum_p \begin{bmatrix}(\alpha_{11}s_1+\alpha_{12}s_2+\alpha_{13}s_3)^2\\(\alpha_{21}s_1+\alpha_{22}s_2+\alpha_{23}s_3)^2\\(\alpha_{31}s_1+\alpha_{32}s_2+\alpha_{33}s_3)^2\end{bmatrix} = \qquad (1.5\text{-}63)$$

$$\begin{bmatrix}\alpha_{1i}\alpha_{1j}s_{1i}s_{1j}\\\alpha_{2i}\alpha_{2j}s_{1i}s_{1j}\\\alpha_{3i}\alpha_{3j}s_{1i}s_{1j}\end{bmatrix} + \begin{bmatrix}\alpha_{1i}\alpha_{1j}s_{2i}s_{2j}\\\alpha_{2i}\alpha_{2j}s_{2i}s_{2j}\\\alpha_{3i}\alpha_{3j}s_{2i}s_{2j}\end{bmatrix} + \begin{bmatrix}\alpha_{1i}\alpha_{1j}s_{3i}s_{3j}\\\alpha_{2i}\alpha_{2j}s_{3i}s_{3j}\\\alpha_{3i}\alpha_{3j}s_{3i}s_{3j}\end{bmatrix}$$

using the summation convention . . .

$$\sum_p \begin{bmatrix}\left(\frac{\partial}{\partial m_p}c_1\right)^2\\\left(\frac{\partial}{\partial m_p}c_2\right)^2\\\left(\frac{\partial}{\partial m_p}c_3\right)^2\end{bmatrix} = \begin{bmatrix}\alpha_{1i}\alpha_{1j}s_{pi}s_{pj}\\\alpha_{2i}\alpha_{2j}s_{pi}s_{pj}\\\alpha_{3i}\alpha_{3j}s_{pi}s_{pj}\end{bmatrix} = \begin{bmatrix}\alpha_{11}\\\alpha_{22}\\\alpha_{33}\end{bmatrix} \qquad (1.5\text{-}64)$$

this equation can now be plugged into the first equation in this chapter. due to $$\begin{bmatrix}\alpha_{11}&\alpha_{12}&\alpha_{13}\\\alpha_{21}&\alpha_{22}&\alpha_{23}\\\alpha_{31}&\alpha_{32}&\alpha_{33}\end{bmatrix}\begin{bmatrix}s_{i1}s_{i1}&s_{i1}s_{i2}&s_{i1}s_{i3}\\s_{i2}s_{i1}&s_{i2}s_{i2}&s_{i2}s_{i3}\\s_{i3}s_{i1}&s_{i3}s_{i2}&s_{i3}s_{i3}\end{bmatrix} = \qquad (1.5\text{-}65)$$

$$\begin{bmatrix}\alpha_{1j}s_{ij}s_{i1}&\alpha_{1j}s_{ij}s_{i2}&\alpha_{1j}s_{ij}s_{i3}\\\alpha_{2j}s_{ij}s_{i1}&\alpha_{2j}s_{ij}s_{i2}&\alpha_{2j}s_{ij}s_{i3}\\\alpha_{3j}s_{ij}s_{i1}&\alpha_{3j}s_{ij}s_{i2}&\alpha_{3j}s_{ij}s_{i3}\end{bmatrix} = \begin{bmatrix}1&0&0\\0&1&0\\0&0&1\end{bmatrix}$$

this is the classical result. The variance associated with this term depends on the s's, the samples in the database. You could give the algorithm any mixture and this term doesn't change.

Covariant or terms (for the same pixel p therefore dropping subscript p for now) . . .

$$\frac{\partial}{\partial s_l}\begin{bmatrix} c_1 \\ c_2 \\ c_3 \end{bmatrix} = \left(\frac{-1}{c_l}\right)\left(\begin{bmatrix} (\alpha_{11}s_1 + \alpha_{12}s_2 + \alpha_{13}s_3) + c_l(\alpha_{1l} - r) \\ (\alpha_{21}s_1 + \alpha_{22}s_2 + \alpha_{23}s_3) + c_l(\alpha_{2l} - r) \\ (\alpha_{31}s_1 + \alpha_{32}s_2 + \alpha_{33}s_3) + c_l(\alpha_{3l} - r) \end{bmatrix}\right) \quad (1.5\text{-}66)$$

$$\frac{\partial}{\partial m_p}\begin{bmatrix} c_1 \\ c_2 \\ c_3 \end{bmatrix} = \begin{bmatrix} \alpha_{11}s_1 + \alpha_{12}s_2 + \alpha_{13}s_3 \\ \alpha_{21}s_1 + \alpha_{22}s_2 + \alpha_{23}s_3 \\ \alpha_{31}s_1 + \alpha_{32}s_2 + \alpha_{33}s_3 \end{bmatrix} \quad (1.5\text{-}67)$$

$$\begin{bmatrix} \left(\frac{\partial}{\partial s_l}c_1\right)\left(\frac{\partial}{\partial m_p}c_1\right) \\ \left(\frac{\partial}{\partial s_l}c_2\right)\left(\frac{\partial}{\partial m_p}c_2\right) \\ \left(\frac{\partial}{\partial s_l}c_3\right)\left(\frac{\partial}{\partial m_p}c_3\right) \end{bmatrix} = \left(\frac{-1}{c_l}\right)\begin{bmatrix} (\alpha_{11}s_1 + \alpha_{12}s_2 + \alpha_{13}s_3)((\alpha_{11}s_1 + \alpha_{12}s_2 + \alpha_{13}s_3) + c_l(\alpha_{1l} - r)) \\ (\alpha_{21}s_1 + \alpha_{22}s_2 + \alpha_{23}s_3)((\alpha_{21}s_1 + \alpha_{22}s_2 + \alpha_{23}s_3) + c_l(\alpha_{2l} - r)) \\ (\alpha_{31}s_1 + \alpha_{32}s_2 + \alpha_{33}s_3)((\alpha_{31}s_1 + \alpha_{32}s_2 + \alpha_{33}s_3) + c_l(\alpha_{3l} - r)) \end{bmatrix} \quad (1.5\text{-}68)$$

$$\begin{bmatrix} \left(\frac{\partial}{\partial s_l}c_1\right)\left(\frac{\partial}{\partial m_p}c_1\right) \\ \left(\frac{\partial}{\partial s_l}c_2\right)\left(\frac{\partial}{\partial m_p}c_2\right) \\ \left(\frac{\partial}{\partial s_l}c_3\right)\left(\frac{\partial}{\partial m_p}c_3\right) \end{bmatrix} = \left(\frac{-1}{c_l}\right)\left(\begin{bmatrix} (\alpha_{11}s_1 + \alpha_{12}s_2 + \alpha_{13}s_3)(\alpha_{11}s_1 + \alpha_{12}s_2 + \alpha_{13}s_3) \\ (\alpha_{21}s_1 + \alpha_{22}s_2 + \alpha_{23}s_3)(\alpha_{21}s_1 + \alpha_{22}s_2 + \alpha_{23}s_3) \\ (\alpha_{31}s_1 + \alpha_{32}s_2 + \alpha_{33}s_3)(\alpha_{31}s_1 + \alpha_{32}s_2 + \alpha_{33}s_3) \end{bmatrix} + \begin{bmatrix} c_l(\alpha_{11}s_1 + \alpha_{12}s_2 + \alpha_{13}s_3)(\alpha_{1l} - r) \\ c_l(\alpha_{21}s_1 + \alpha_{22}s_2 + \alpha_{23}s_3)(\alpha_{2l} - r) \\ c_l(\alpha_{31}s_1 + \alpha_{32}s_2 + \alpha_{33}s_3)(\alpha_{3l} - r) \end{bmatrix}\right) \quad (1.5\text{-}69)$$

$$\begin{bmatrix} \left(\frac{\partial}{\partial s_l}c_1\right)\left(\frac{\partial}{\partial m_p}c_1\right) \\ \left(\frac{\partial}{\partial s_l}c_2\right)\left(\frac{\partial}{\partial m_p}c_2\right) \\ \left(\frac{\partial}{\partial s_l}c_3\right)\left(\frac{\partial}{\partial m_p}c_3\right) \end{bmatrix} = \left(\frac{-1}{c_l}\right)\begin{bmatrix} \alpha_{1i}s_i\alpha_{1j}s_j \\ \alpha_{2i}s_i\alpha_{2j}s_j \\ \alpha_{3i}s_i\alpha_{3j}s_j \end{bmatrix} - \begin{bmatrix} (\alpha_{11}s_1 + \alpha_{12}s_2 + \alpha_{13}s_3)(\alpha_{1l} - r) \\ (\alpha_{21}s_1 + \alpha_{22}s_2 + \alpha_{23}s_3)(\alpha_{2l} - r) \\ (\alpha_{31}s_1 + \alpha_{32}s_2 + \alpha_{33}s_3)(\alpha_{3l} - r) \end{bmatrix} \quad (1.1\text{-}1)$$

$$\begin{bmatrix} \left(\frac{\partial}{\partial s_l}c_1\right)\left(\frac{\partial}{\partial m_p}c_1\right) \\ \left(\frac{\partial}{\partial s_l}c_2\right)\left(\frac{\partial}{\partial m_p}c_2\right) \\ \left(\frac{\partial}{\partial s_l}c_3\right)\left(\frac{\partial}{\partial m_p}c_3\right) \end{bmatrix} = \left(\frac{-1}{c_l}\right)\begin{bmatrix} \alpha_{1i}\alpha_{1j}s_is_j \\ \alpha_{2i}\alpha_{2j}s_is_j \\ \alpha_{3i}\alpha_{3j}s_is_j \end{bmatrix} - \begin{bmatrix} (\alpha_{11}s_1 + \alpha_{12}s_2 + \alpha_{13}s_3)(\alpha_{1l} - r) \\ (\alpha_{21}s_1 + \alpha_{22}s_2 + \alpha_{23}s_3)(\alpha_{2l} - r) \\ (\alpha_{31}s_1 + \alpha_{32}s_2 + \alpha_{33}s_3)(\alpha_{3l} - r) \end{bmatrix} \quad (1.1\text{-}2)$$

this equation can now be plugged into the first equation in this chapter. notice that in many cases these terms will be negative. this is good.

We claim:

1. A method for identifying the amount of at least one known constituent contained within an unknown mixture comprising:

(a) irradiating the purest available sample of at least one known constituent with a reference electromagnetic wave excitation source that sequentially emits a plurality of individual bands of wavelengths of radiation, with the energy from the excitation source interacting with the sample at a first set of wavelengths;

(b) recording at least one parameter as a measurement of the response of the sample of the at least one known constituent to the excitation source at a second set of wavelengths to form an n-dimensional array consisting of a multiplicity of elements, where $n \geq 2$;

(c) creating an optimized patch subset in the array by an evolutionary algorithm, the optimized patch subset containing only those array elements which indicate the presence of the sample of the at least one known constituent;

(d) irradiating the unknown mixture at the first set of wavelengths;

(f) recording the at least one parameter as a measurement of the response of the unknown mixture to the excitation source at the second set of wavelengths to form the n-dimensional array of step (b); and (g) determining the amount of the at least one known constituent in the unknown mixture by minimizing a function of the residuals between measurements of the at least one parameter associated with the elements in the optimized patch subset for the sample of the at least one known constituent and the measurements of the at least one parameter associated with the elements in a patch subset from the unknown mixture which corresponds with the optimized patch set.

2. The method of claim 1 wherein the excitation source is a flash lamp equipped with a plurality of filters to provide the first set of wavelengths.

3. The method of claim 1 wherein the excitation source is a laser tuned to the first set of wavelengths.

4. The method of claim 1 wherein the determining of the amount of the at least one known constituent is done by multivariate analysis.

5. The method of claim 1 wherein the at least one known constituent is at least one chemical.

6. The method of claim 1 wherein steps (a)–(c) are conducted separately from and prior to the succeeding steps and the optimized patch subset from step (c) is stored for later use in the determining step (g).

7. The method of claim 1 wherein the at least one parameter is the magnitude of the each of the second set of wavelengths.

8. The method of claim 7 wherein the magnitude measured is of uv fluorescence.

9. The method of claim 1 wherein the at least one known constituent is at least one biologic material.

10. The method of claim 9 wherein the at least one biologic material is at least one material selected from the group consisting of viruses, bacteria, DNA, RNA, and abnormal cells including cancer cells.

11. The method of claim 1 wherein the creating of the optimized patch subset in the array by the evolutionary algorithm is done by a method comprising:
  (a) creating a first generation of unoptimized patch subsets with z members, each patch subset being described by initial patch boundaries as part of a genetic sequence describing each patch subset,
  (b) assigning a fitness level to each member of the first generation as a function of the magnitude of a function of the residuals remaining when the amounts of the at least one known constituent determined from the member of the first generation of patch sets are subtracted from the actual amounts,
  (c) dropping those members of the first generation below a certain fitness level, allowing at least some of the remaining members to reproduce by exchanging corresponding portions of their genetic sequences, and introducing random mutations into some of the sequences of the members to form a next generation of members,
  (d) assigning a fitness level to each member of the next generation of step (c) as a function of the residuals remaining when the amounts of the at least one known constituent determined from the member of the next generation of patch sets of step (c) are subtracted from the actual amounts, and
  (e) repeating steps (c) and (d) until a member of a succeeding generation is identified as having sufficient fitness to qualify as the optimized patch subset.

12. The method of claim 11 wherein the member of a succeeding generation identified as having sufficient fitness is a member representing the average patch subset for that generation.

13. The method of claim 1 wherein the element is a pixel representing one of the second set of wavelengths.

14. The method of claim 13 wherein the pixel is associated with other pixels to form a two dimensional array.

15. The method of claim 14 wherein the optimized patch subset includes only those associated pixels which contain information indicative of the at least one known constituent.

16. A method for identifying the amount of at least one known chemical contained within an unknown mixture comprising:
  (a) irradiating the purest available sample of at least one chemical with a reference electromagnetic wave excitation source that sequentially emits a plurality of individual bands of wavelengths of radiation, with the energy from the excitation source interacting with the sample at a first set of wavelengths;
  (b) recording the uv fluourescence response of the sample of the at least one chemical to the excitation source at a second set of wavelengths to form an two-dimensional array;
  (c) creating an optimized patch subset in the array by an evolutionary algorithm, the optimized patch subset containing only those array elements which indicate the presence of the sample of the at least one chemical;
  (d) irradiating the unknown mixture at the first set of wavelengths;
  (f) recording the at least one parameter as a measurement of the response of the unknown mixture to the excitation source at the second set of wavelengths to form the n-dimensional array of step (b); and
  (g) determining the amount of the at least one known constituent in the unknown mixture by minimizing a function of the residuals between measurements of the at least parameter associated with the elements in the optimized patch subset for the sample of the at least one chemical and the measurements of the at least one parameter associated with the elements in a patch subset from the unknown mixture which corresponds with the optimized patch set.

17. The method of claim 16 wherein the excitation source is a flash lamp equipped with a plurality of filters to provide the first set of wavelengths.

18. The method of claim 16 wherein the excitation source is a laser tuned to the first set of wavelengths.

19. The method of claim 16 wherein the determining of the amount of the at least one known constituent is done by multivariate analysis.

20. The method of claim 16 wherein steps (a)–(c) are conducted separately from and prior to the succeeding steps and the optimized patch subset from step (c) is stored for later use in the determining step (g).

21. A method for identifying the amount of at least one known constituent contained within an unknown mixture comprising:
  (a) irradiating a set of at least one of the purest available samples of the known constituents with a reference excitation source, the excitation source emitting at a first set of wavelengths;
  (b) recording at least one parameter as a measurement of the response of the at least one samples of the constituents to the excitation source at a second set of wavelengths;
  (c) creating, by an evolutionary algorithm, an optimized neural network comprising at least three layers of neurons comprising an input layer, at least one middle layer and an output layer, the input layer including neurons having a single input connection exclusively to an individual band of wavelengths in the second set of wavelengths, the output layer of neurons having a single output connection, and each neuron in a layer being at least initially connected to each of the neurons in the layers above it, the input from each such connection to a neuron from the layer above being multiplied by a weight in each neuron, the optimized neural network being created by a process comprising:
    (i) creating a first generation of a neural network having at least three layers with z members in the generation each member being described by a genetic sequence containing initial weights assigned to the input connections to the neurons in the layers,
    (ii) assigning a fitness level to each member of the first generation as a function of the accuracy of the information provided from the outputs of the output neurons compared against the measurements of step (b),
    (iii) dropping those members of the first generation below a certain fitness level, allowing at least some of the remaining members to reproduce by exchanging corresponding portions of their genetic sequences, and introducing random mutations into some of the sequences of the members to form a next generation of members,
    (iv) assigning a fitness level to each member of the next generation of step (iii) as a function of the accuracy of the information provided from the outputs of the output neurons compared against the measurements of step (b) modified by a change in the relative concentrations of the at least one sample in the set, and (v) repeating steps (iii) and (iv) with repeated changes in the relative concentrations of the samples in the set until a member of a succeeding generation is identified as having sufficient accuracy of output information to qualify as the optimized neural network (d) irradiating the unknown mixture with the excitation source at the first set of wavelengths;

(e) recording the at least one parameter from the unknown mixture at the second set of wavelengths; and (f) identifying the at least one known constituent in the unknown mixture by observing the output of the optimized neural network after it is supplied with the parameters measured at the second set of wavelengths from the unknown mixture at the inputs of the optimized neural network.

22. The method of claim 21 wherein the evolutionary algorithm further removes at least some of the interconnections from the network with zero value weights associated therewith.

23. The method of claim 21 wherein the evolutionary algorithm further removes at least some of the neurons for which the summed inputs to that neuron total zero.

24. The method of claim 21 wherein the evolutionary algorithm introduces random mutations in part by adding new neurons to the network.

25. The method of claim 21 wherein the evolutionary algorithm introduces random mutations in part by adding new interconnections to the neurons in the network.

26. The method of claim 21 wherein the excitation source is a flash lamp equipped with a plurality of filters to provide the first set of wavelengths.

27. The method of claim 21 wherein the excitation source is a laser tuned to the first set of wavelengths.

28. The method of claim 21 wherein the parameter measured is the magnitude of uv fluorescence.

29. The method of claim 21 wherein the at least one known constituent is at least one chemical.

30. The method of claim 21 wherein at least some of the input layer neurons are connected exclusively to inputs providing information about the operational characteristics of the apparatus performing the irradiating and recording.

31. The method of claim 21 wherein the identification includes a determination of concentration.

32. The method of claim 21 wherein steps (a)–(c) are conducted separately from and prior to the succeeding steps and the optimized neural network from step (c) is stored for later use in the identifying step (f).

33. The method of claim 21 wherein the at least one known constituent is at least one biologic material.

34. The method of claim 33 wherein the at least one biologic material is at least one material selected from the group consisting of viruses, bacteria, DNA, RNA, and abnormal cells including cancer cells.

35. A method for identifying the amount of at least one known chemical contained within an unknown mixture comprising:

(a) irradiating a set of at least one purest available sample of the known chemicals with a reference excitation source, the excitation source emitting at a first set of wavelengths;

(b) recording at least one parameter as a measurement of the response of the at least one sample of the chemical to the excitation source at a second set of wavelengths;

(c) creating, by an evolutionary algorithm, an optimized neural network comprising at least three layers of neurons comprising an input layer, at least one middle layer and an output layer, the input layer including neurons having a single input connection exclusively to an individual band of wavelengths in the second set of wavelengths, the output layer of neurons having a single output connection, and each neuron in a layer being at least initially connected to each of the neurons in the layers above it, the input from each such connection to a neuron from the layer above being multiplied by a weight in each neuron, the optimized neural network being created by a process comprising:

(i) creating a first generation of a neural network having at least three layers with z members in the generation each member being described by a genetic sequence containing initial weights assigned to the input connections to the neurons in the layers, (ii) assigning a fitness level to each member of the first generation as a function of the accuracy of the information provided from the outputs of the output neurons compared against the measurements of step (b), (iii) dropping those members of the first generation below a certain fitness level, allowing at least some of the remaining members to reproduce by exchanging corresponding portions of their genetic sequences, and introducing random mutations into some of the sequences of the members to form a next generation of members, (iv) assigning a fitness level to each member of the next generation of step (iii) as a function of the accuracy of the information provided from the outputs of the output neurons compared against the measurements of step (b) modified by a change in the relative concentrations of the at least one sampler in the set, and (v) repeating steps (iii) and (iv) with repeated changes in the relative concentrations of the samples in the set until a member of a succeeding generation is identified as having sufficient accuracy of output information to qualify as the optimized neural network (d) irradiating the unknown mixture at the first set of wavelengths;

(e) recording the at least one parameter from the unknown mixture at the second set of wavelengths; and (f) identifying the at least one known chemical in the unknown mixture by observing the output of the optimized neural network after it is supplied with the parameters measured at the second set of wavelengths from the unknown mixture at the inputs of the optimized neural network.

36. The method of claim 35 wherein the evolutionary algorithm further removes at least some of the interconnections from the network with zero value weights associated therewith.

37. The method of claim 35 wherein the evolutionary algorithm further removes at least some of the neurons for which the summed inputs to that neuron total zero.

38. The method of claim 35 wherein the evolutionary algorithm introduces random mutations in part by adding new neurons to the network.

39. The method of claim 35 wherein the evolutionary algorithm introduces random mutations in part by adding new interconnections to the neurons in the network.

40. The method of claim 35 wherein the identification includes a determination of concentration.

41. The method of claim 35 wherein steps (a)–(c) are conducted separately from and prior to the succeeding steps and the optimized neural network from step (c) is stored for later use in the identifying step (f).

42. A system for identifying the amount of at least one known constituent contained within an unknown mixture comprising:

(a) a reference electromagnetic wave excitation source that sequentially emits a plurality of discrete bands of wavelengths of radiation for irradiating a purest available sample of at least one constituent at a first set of wavelengths;

(b) means for recording at least one parameter as a measurement of the response of the sample of the at least one constituent to the excitation source at a second set of wavelengths to form an n-dimensional array consisting of a multiplicity of elements, where $n \geq 2$;

(c) means for creating an optimized patch subset in the array by an evolutionary algorithm, the optimized patch subset containing only those array elements which indicate the presence of the pure sample of the at least one constituent;

(d) means for irradiating the unknown mixture at the first set of wavelengths;

(f) means for recording the at least one parameter as a measurement of the response of the unknown mixture to the excitation source at the second set of wavelengths to form the n-dimensional array of step (b); and (g) means for determining the amount of the at least one known constituent in the unknown mixture by minimizing a function of the residuals between measurements of the at least parameter associated with the elements in the optimized patch subset for the sample of the at least one constituent and the measurements of the at least one parameter associated with the elements in a patch subset from the unknown mixture which corresponds with the optimized patch set.

43. The system of claim 42 wherein the excitation source is a flash lamp equipped with a plurality of filters to provide the first set of wavelengths.

44. The system of claim 42 wherein the excitation source is a laser tuned to the first set of wavelengths.

45. The system of claim 42 wherein the means for determining of the amount of the at least one known constituent comprises multivariate analysis means.

46. The system of claim 42 wherein the at least one known constituent is at least one chemical.

47. The system of claim 42 wherein the means for creating the optimized patch subset in the array by the evolutionary algorithm comprises:

(a) means for creating a first generation of unoptimized patch subsets with z members in the generation each member being described by initial patch boundaries as part of a genetic sequence describing each, (b) means for assigning a fitness level to each member of the first generation as a function of the magnitude of a function of the residuals remaining when the amounts of the at least one known constituent determined from the member of the first generation of patch sets are subtracted from the actual amounts, (c) means for dropping those members of the first generation below a certain fitness level, allowing at least some of the remaining members to reproduce by exchanging corresponding portions of their genetic sequences, and introducing random mutations into some of the sequences of the members to form a next generation of members, (d) means for assigning a fitness level to each member of the next generation of step (c) as a function of the residuals remaining when the amounts of the at least one known constituent determined from the member of the next generation of patch sets of step (c) are subtracted from the actual amounts, and (e) means for repeating steps (c) and (d) until a member of a succeeding generation is identified as having sufficient fitness to qualify as the optimized patch subset.

48. The system of claim 47 wherein the member of a succeeding generation identified as having sufficient fitness is a member representing the average patch subset for that generation.

49. The system of claim 42 wherein the at least one parameter is the magnitude of the each of the second set of wavelengths.

50. The system of claim 49 wherein the magnitude measured is of uv fluorescence.

51. The system of claim 42 wherein the at least one known constituent is at least one biologic material.

52. The system of claim 51 wherein the at least one biologic material is at least one material selected from the group consisting of viruses, bacteria, DNA, RNA, and abnormal cells including cancer cells.

53. The system of claim 42 wherein the element is a pixel representing one of the second set of wavelengths.

54. The system of claim 53 wherein the pixel is associated with other pixels to form a two dimensional array.

55. The system of claim 54 wherein the optimized patch subset includes only those associated pixels which contain information indicative of the at least one known constituent.

56. A system for identifying the amount of at least one known constituent contained within an unknown mixture comprising:

(a) a reference excitation source for irradiating a set of at least one purest available sample of the known constituents at a first set of wavelengths;

(b) means for recording at least one parameter as a measurement of the response of the at least one sample of the constituent to the excitation source at a second set of wavelengths;

(c) means for creating, by an evolutionary algorithm, an optimized neural network comprising at least three layers of neurons comprising an input layer, at least one middle layer and an output layer, the input layer including neurons having a single input connection exclusively to an individual band of wavelengths in the second set of wavelengths, the output layer of neurons having a single output connection, and each neuron in a layer being at least initially connected to each of the neurons in the layers above it, the input from each such connection to a neuron from the layer above being multiplied by a weight in each neuron, the means for creating the optimized neural network comprising:

(i) means for creating a first generation of a neural network having at least three layers with z members in the generation each having being described by a genetic sequence containing initial weights assigned to the input connections to the neurons in the layers, (ii) means for assigning a fitness level to each member of the first generation as a function of the accuracy of the information provided from the outputs of the output neurons compared against the measurements of step (b), (iii) means for dropping those members of the first generation below a certain fitness level, allowing at least some of the remaining members to reproduce by exchanging corresponding portions of their genetic sequences, and introducing random mutations into some of the sequences of the members to form a next generation of members, (iv) means for assigning a fitness level to each member of the next generation of step (iii) as a function of the accuracy of the information provided from the outputs of the output neurons compared against the measurements of step (b) modified by a change in the relative concentrations of the at least one samples in the set, and (v) means for repeating steps (iii) and (iv) with repeated changes in the relative concentrations of the samples in the set until a member of a succeeding generation is identified as having sufficient accuracy of output information to qualify as the optimized neural network (d) means for irradiating the unknown mixture at the first set of wavelengths;

(e) means for recording the at least one parameter from the unknown mixture at the second set of wavelengths; and (f) means for identifying the at least one known constituent in the unknown mixture by observing the output of the optimized neural network after it is supplied with the parameters measured at the second set of wavelengths from the unknown mixture at the inputs of the optimized neural network.

57. The system of claim 56 wherein the excitation source is a flash lamp equipped with a plurality of filters to provide the first set of wavelengths.

58. The system of claim 56 wherein the excitation source is a laser tuned to the first set of wavelengths.

59. The system of claim 56 wherein the parameter measured is the magnitude of uv fluorescence.

60. The system of claim 56 wherein the at least one known constituent is at least one chemical.

61. The system of claim 56 wherein at least some of the input layer neurons are connected exclusively to inputs providing information about the operational characteristics of the apparatus performing the irradiating and recording.

62. The system of claim 56 wherein the identification includes a determination of concentration.

63. The system of claim 53 wherein the at least one known constituent is at least one biologic material.

64. The system of claim 63 wherein the at least one biologic material is at least one material selected from the group consisting of viruses, bacteria, DNA, RNA, and abnormal cells including cancer cells.

65. A system for identifying the amount of at least one known constituent contained within an unknown mixture comprising:

means for establishing a database containing responses of samples of the known constituents to irradiation at a first set of wavelengths of electromagnetic radiation measured at a second set of wavelengths, the database comprising a plurality of two-dimensional patches of pixels containing information measured at the second set of wavelengths indicative of the known constituents;

means for establishing an optimized neural network comprising an evolutionary algorithm which evolves the structure of an at least three level neural network by training the neural network against a set containing the responses of a plurality of known constituents to the first set of wavelengths which set changes the relative concentrations of its members as each generation of the neural network evolves, said optimized neural network providing the amount of the known constituents when provided with the response of the known constituents at the second set of wavelengths;

means to irradiate the unknown mixture with the first set of wavelengths:

means to record the responses of the unknown mixture at the second set of wavelengths;

means to process the responses with the optimized neural network to ascertain a first value for the amounts of the known constituents in the unknown mixture;

means to select from the database those two-dimensional patches indicative of the known constituents ascertained by the optimized neural network;

means to minimize the residuals by multivariate analysis between the patches selected from the database by the optimized neural network and the corresponding patches in the responses from the unknown mixture, said means providing the amounts of the constituents.

66. The system of claim 65 further comprising means to compare the amounts of the constituents from the optimized neural network and the amounts of the constituents from the means for minimizing the residuals by multivariate analysis.

67. A method for identifying the amount of at least one known constituent contained within an unknown mixture comprising:

establishing a database containing responses of samples of the known constituents to irradiation at a first set of wavelengths of electromagnetic radiation measured at a second set of wavelengths, the database comprising a plurality of two-dimensional patches of pixels containing information measured at the second set of wavelengths indicative of the known constituents;

establishing an optimized neural network comprising an evolutionary algorithm which evolves the structure of an at least three level neural network by training the neural network against a set containing the responses of a plurality of known constituents to the first set of wavelengths which set changes the relative concentrations of its members as each generation of the neural network evolves, said optimized neural network providing the amount of the known constituents when provided with the response of the known constituents at the second set of wavelengths;

irradiating the unknown mixture with the first set of wavelengths:

recording the responses of the unknown mixture at the second set of wavelengths;

processing the responses with the optimized neural network to ascertain a first value for the amounts of the known constituents in the unknown mixture;

selecting from the database those two-dimensional patches indicative of the known constituents ascertained by the optimized neural network;

minimizing the residuals by multivariate analysis between the patches selected from the database by the optimized neural network and the corresponding patches in the responses from the unknown mixture, thereby providing the amounts of the constituents.

68. The method of claim 67 further comprising comparing the amounts of the constituents from the optimized neural network and the amounts of the constituents from the means for minimizing the residuals by multivariate analysis.

* * * * *